(12) United States Patent
Saha et al.

(10) Patent No.: US 7,511,061 B2
(45) Date of Patent: Mar. 31, 2009

(54) TRIAZOLES AS FARNESYL TRANSFERASE INHIBITORS

(75) Inventors: Ashis Kumar Saha, Harleysville, PA (US); David William End, Ambler, PA (US); Bart Lieven Daniel De Corte, Southampton, PA (US); Henry Joseph Breslin, Lansdale, PA (US); Li Liu, Doylestown, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 209 days.

(21) Appl. No.: 11/143,814

(22) Filed: Jun. 2, 2005

(65) Prior Publication Data
US 2005/0234117 A1 Oct. 20, 2005

Related U.S. Application Data

(62) Division of application No. 10/130,322, filed as application No. PCT/EP00/11393 on Nov. 15, 2000.

(60) Provisional application No. 60/165,434, filed on Nov. 15, 1999.

(51) Int. Cl.
*A61K 31/4196* (2006.01)
*A61K 31/47* (2006.01)
*C07D 215/00* (2006.01)
*C07D 249/06* (2006.01)

(52) U.S. Cl. .................... 514/311; 546/112; 546/152; 546/169; 548/262.2; 548/267.6; 514/383

(58) Field of Classification Search ............... 546/112, 546/152, 169; 548/262.2, 267.6; 514/311, 514/383
See application file for complete search history.

(56) References Cited

U.S. PATENT DOCUMENTS

| | | | |
|---|---|---|---|
| 4,243,408 A | 1/1981 | Chan | |
| 5,217,985 A | 6/1993 | Reitz | |
| 5,710,171 A | 1/1998 | Dinsmore | |
| 5,780,488 A | 7/1998 | Bergman | |
| 5,817,678 A | 10/1998 | Kim | |
| 5,854,264 A | 12/1998 | Anthony | |
| 5,854,265 A | 12/1998 | Anthony | |
| 5,869,579 A | 2/1999 | Hodges et al. | |
| 5,872,136 A | 2/1999 | Anthony | |
| 5,874,452 A | 2/1999 | Anthony | |
| 5,880,140 A | 3/1999 | Anthony | |
| 5,883,105 A | 3/1999 | Anthony | |
| 5,891,889 A | 4/1999 | Anthony | |
| 5,932,590 A | 8/1999 | Ciccarone | |
| 5,939,439 A * | 8/1999 | Anthony et al. ............ | 514/333 |
| 5,939,557 A | 8/1999 | Anthony | |
| 7,049,324 B1 * | 5/2006 | Saha et al. ................. | 514/311 |

FOREIGN PATENT DOCUMENTS

WO    WO 9324465 A1    12/1993

| | | |
|---|---|---|
| WO | WO 9727853 A1 | 8/1997 |
| WO | WO 9736585 A1 | 10/1997 |
| WO | WO 9736881 A1 | 10/1997 |
| WO | WO 9736897 A1 | 10/1997 |
| WO | WO 9828980 A1 | 7/1998 |
| WO | WO 9840383 A1 | 9/1998 |
| WO | WO 0136395 A1 | 5/2001 |

OTHER PUBLICATIONS

Kohl et al., Science, vol. 260, 1934-1937, 1993.
Sepp-Lorenzino et al., Cancer Res., vol. 55, 5302-5309, 1995.
Du et al., Molec. Cell Biol., vol. 19, 1831-1840, 1999.

(Continued)

*Primary Examiner*—Golam M Shameem

(57) ABSTRACT

A prodrug, N-oxide, addition salt, quaternary amine or stereochemically isomeric form thereof, wherein $L^1$ and $L^2$ are $R^1$—Y— wherein each ($R^1$—Y)— substituent is defined independently of the other; Y is $C_{1-4}$alkanediyl, $C_{2-4}$alkenediyl, $C_{2-4}$alkynediyl, C(=O), or a direct bond; $R^1$ is hydrogen, cyano, aryl or a substituted or unsubstituted $C_{1-14}$heterocycle; =$Z^1$-$Z^2$=$Z^3$- represents a radical of formula =N—N=CH— (a-1), =N—CH=N— (a-2), =CH—N=N— (a-3); X is $SO_2$, $(CH_2)_n$ wherein n is 1 to 4, C(=O), C(=S), or a direct bond; $R^2$ is aryl, $C_{3-7}$cycloalkyl, $C_{3-7}$cycloalkyl substituted with one or more substituents independently selected from hydroxy, aryl, aryloxy, a substituted or unsubstituted $C_{1-14}$heterocycle, $C_{3-7}$cycloalkyl, hydroxycarbonyl, $C_{1-6}$alkyloxycarbonyl, hydroxy$C_{1-6}$alkyl, hydroxy$C_{1-6}$ alkyloxy, hydroxy$C_{1-6}$alkylthio and aryl$C_{1-6}$ alkylthio, $C_{1-12}$alkyl or $C_{1-12}$alkyl substituted with one or more substituents independently selected from hydroxy, aryl, aryloxy, a substituted or unsubstituted $C_{1-14}$heterocycle, $C_{3-7}$cycloalkyl, hydroxycarbonyl, $C_{1-6}$alkyloxycarbonyl, hydroxy$C_{1-6}$alkyl, hydroxy$C_{1-6}$alkyloxy, hydroxy$C_{1-6}$alkylthio and aryl$C_{1-6}$alkylthio; $R^3$ is aryl, —$NR^5R^6$, a substituted or unsubstituted $C_{1-14}$heterocycle, or $C_{2-4}$alkenediyl substituted with a substituted or unsubstituted $C_{1-14}$heterocycle or aryl; $R^4$ is hydrogen, aryl, $C_{3-7}$cycloalkyl, $C_{1-6}$alkyl or $C_{1-6}$alkyl substituted with $C_{3-7}$cycloalkyl, hydroxycarbonyl, $C_{1-4}$alkyloxycarbonyl or aryl; $R^5$ and $R^6$ are each independently selected from hydrogen, a substituted or unsubstituted $C_{1-14}$heterocycle, aryl, $C_{1-12}$alkyl and $C_{1-12}$alkyl substituted with one or more substituents selected from hydroxy, aryl, aryloxy or a substituted or unsubstituted $C_{1-14}$heterocycle.

(I)

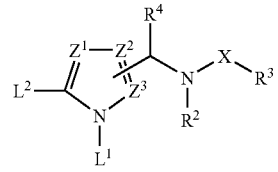

12 Claims, No Drawings

OTHER PUBLICATIONS

Goodman and Gilman, The Pharmacological Basis of Therapeutics, 8th Ed., McGraw Hill, Int. Ed., 1992, "BioTransformation of Drugs", p. 13-15.
Larsen, R., Curr. Opin. Drug Discovery Dev., 1999, 2(6), 651-667.
Kingsbury et al., Curr. Org. Chem. 1999, 3(5), 497-555.
DeLombaert et al., J. Med. Chem., 2000, vol. 43, 488-504.
Owens et al., Bio. Org. Med. Chem. Lett., 1998, vol. 8, 51-56.
Baldwin et al., J. Med. Chem., 1975, vol. 18, 895-900.
Rak et al., Cancer Research, vol. 55, 4575-4580, 1995.
Wyde et al., Antiviral Research, 1998, vol. 38, 31-42.
Baupre et al., J. Clin. Oncol., vol. 17, No. 3, (1999), 1071-1079.
Rowinsky et al., J. Clin. Oncol., Vo. 17, No. 11, (1999), 3631-3652.
International Search Report re: PCT/EP00/11393 dated Apr. 27, 2001.

* cited by examiner

TRIAZOLES AS FARNESYL TRANSFERASE INHIBITORS

CROSS REFERENCE

This application is a division of application Ser. No. 10/130,322, May 13, 2002, which is a 371 of application PCT/EP00/11393, Nov. 15, 2000, which claims priority from U.S. Provisional Patent Application 60/165,434, Nov. 15, 1999. These applications are incorporated herein by reference.

BACKGROUND OF THE INVENTION

The present invention is concerned with triazole derivatives, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a hydroxycarbonyl-terminal tetrapeptide. Therefore, inhibitors of the enzymes that catalyzes this modification, i.e. farnesyl transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Attachment of the $p21^{ras}$ oncoproteins to the plasma membranes can also be the result of geranylgeranyltransferase I (GGTase I) activity. GGTase I attaches the lipid geranylgeranyl to the ras oncoproteins and as such provides a signal for the transformation and uncontrolled growth of malignant tumor cells. Hence, it is generally accepted in the art that geranylgeranyltransferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., Science, vol 260, 1834-1837, 1993), it has been suggested that farnesyl tranferase and/or geranylgeranyltransferase inhibitors can be very useful against these types of cancer.

More recent studies have demonstrated that farnesyl protein transferase inhibitors have antitumor activity which extends beyond tumors having ras mutations (Sepp-Lorenzino et al., Cancer Res. Vol 55, 5302-5309, 1995 ). This additional activity may derive from effects on rhoB farnesylation (Du et al., Molec. Cell. Biol. Vol 19, 1831-1840, 1999) or from inhibition of the function of other farnesylated proteins. Regardless of the mechanism, these agents appear to have therapeutic utility in cancer and other proliferative disorders.

It is, therefore, an object of this invention to provide a novel class of peptidomimetic FPTase inhibitors which are capable to inhibit prenylation of proteins, such as Ras, both at the enzymatic and cellular level.

DETAILED DESCRIPTION

The present invention concerns compounds of formula (I)

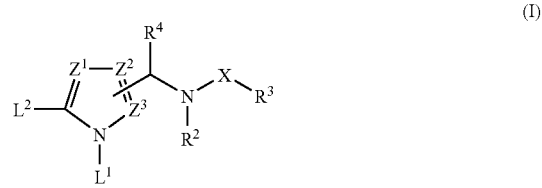

a prodrug, N-oxide, addition salt, quaternary amine or stereochemically isomeric form thereof, wherein $L^1$ and $L^2$ are $R^1$—Y— wherein each ($R^1$—Y)— substituent is defined independently of the other;

Y is $C_{1-4}$alkanediyl, $C_{2-4}$alkenediyl, $C_{2-4}$alkynediyl, C(=O), or a direct bond;

$R^1$ is hydrogen, cyano, aryl or a substituted or unsubstituted $C_{1-4}$heterocycle;

=$Z^1$-$Z^2$=$Z^3$- represents a radical of formula

=N—N=CH—     (a-1)

=N—CH=N—     (a-2)

=CH—N=N—     (a-3)

X is $SO_2$, $(CH_2)_n$ wherein n is 1 to 4, C(=O), C(=S), or a direct bond $R^2$ is aryl, $C_{3-7}$cycloalkyl, $C_{3-7}$cycloalkyl substituted with one or more substituents independently selected from hydroxy, aryl, aryloxy, a substituted or unsubstituted $C_{1-14}$heterocycle, $C_{3-7}$cycloalkyl, hydroxycarbonyl, $C_{1-6}$alkyloxycarbonyl, hydroxy$C_{1-6}$alkyl, hydroxy$C_{1-6}$alkyloxy, hydroxy$C_{1-6}$alkylthio and aryl$C_{1-6}$alkylthio, $C_{1-12}$alkyl or $C_{1-12}$alkyl substituted with one or more substituents independently selected from hydroxy, aryl, aryloxy, a substituted or unsubstituted $C_{1-14}$heterocycle, $C_{3-7}$cycloalkyl, hydroxycarbonyl, $C_{1-6}$alkyloxycarbonyl, hydroxy$C_{1-6}$alkyl, hydroxy$C_{1-6}$alkyloxy, hydroxy$C_{1-6}$alkylthio and aryl$C_{1-6}$alkylthio;

$R^3$ is aryl, —$NR^5R^6$, a substituted or unsubstituted $C_{1-14}$heterocycle, or $C_{2-4}$alkenediyl substituted with a substituted or unsubstituted $C_{1-14}$heterocycle or aryl;

$R^4$ is hydrogen, aryl, $C_{3-7}$cycloalkyl, $C_{1-6}$alkyl or $C_{1-6}$alkyl substituted with $C_{3-7}$cycloalkyl, hydroxycarbonyl, $C_{1-4}$alkyloxycarbonyl or aryl;

$R^5$ and $R^6$ are each independently selected from hydrogen, a substituted or unsubstituted $C_{1-14}$heterocycle, aryl, $C_{1-12}$alkyl and $C_{1-12}$alkyl substituted with one or more substituents selected from hydroxy, aryl, aryloxy or a substituted or unsubstituted $C_{1-14}$heterocycle;

$R^7$ is substituted or unsubstituted phenyl, —$NR^8R^9$ or a substituted or unsubstituted $C_{1-14}$heterocycle;

$R^8$ and $R^9$ are independently selected from hydrogen, substituted or unsubstituted phenyl, $C_{3-6}$cycloalkyl, a substituted or unsubstituted $C_{1-14}$heterocycle, $C_{1-6}$alkyl and $C_{1-6}$alkyl substituted with one or more substituents independently selected from $C_{1-4}$alkyloxycarbonyl, hydroxycarbonyl, substituted or unsubstituted phenyl and a substituted or unsubstituted $C_{1-14}$heterocycle;

aryl, as a group or part of a group, is naphthyl or phenyl each of which may optionally be substituted with one or more substituents selected from trifluoromethyl, trifluoromethyloxy, halo, cyano, nitro, $C_{1-12}$alkyl, $C_{1-12}$alkyloxy, phenyl$C_{1-6}$alkyl, phenyl$C_{1-6}$alkyloxy, phenyloxy, phenylcarbonyl, hydroxycarbonyl, $C_{1-6}$alkylcarbonyl, $C_{1-6}$alkyloxycarbonyl, amino, mono- or di($C_{1-4}$alkyl)amino, mono- or di($C_{1-4}$alkyl)amino wherein said $C_{1-4}$alkyl is substituted with one or more substituted or unsubstituted phenyl, $S(O)_2$—$R^7$, $C_{1-6}$alkylcarbonylamino, substituted or unsubstituted phenyl, and a substituted or unsubstituted $C_{1-14}$heterocycle.

As used in the foregoing definitions and hereinafter, halo is generic to fluoro, chloro, bromo and iodo; $C_{1-4}$alkyl as a group or part of a group defines straight and branched chain saturated hydrocarbon radicals having from 1 to 4 carbon atoms such as, e.g. methyl, ethyl, propyl, butyl, 1-methylethyl, 2-methylpropyl and the like; $C_{1-6}$alkyl as a group or part of a group includes $C_{1-4}$alkyl and the higher homologues thereof having 5 to 6 carbon atoms such as, for example, pentyl, 2-methyl-butyl, hexyl, 2-methylpentyl and the like; $C_{1-12}$alkyl as a group or part of a group includes $C_{1-4}$alkyl, $C_{1-6}$alkyl and the higher homologues thereof having 7 to 12 carbon atoms such as, for example heptyl, octyl, nonyl, decyl, undecyl, dodecyl and the like; $C_{1-4}$alkanediyl as a group or part of a group defines bivalent straight and branched chained saturated hydrocarbon radicals having from 1 to 4 carbon atoms, such as, for example, methylene, 1,2-ethanediyl, 1,3-propanediyl, 1,4-butanediyl and the branched isomers thereof; $C_{2-4}$alkenyl as a group or part of a group defines straight and branched chain hydrocarbon radicals containing one double bond and having from 2 to 4 carbon atoms such as, for example, ethenyl, 2-propenyl, 3-butenyl and the like; $C_{2-4}$alkenediyl as a group or part of a group defines bivalent straight and branched chain hydrocarbon radicals containing one double bond and having from 2 to 4 carbon atoms such as, for example, ethenediyl, 2-propenediyl, 3-butenediyl and the like; $C_{2-4}$alkynyl as a group or part of a group defines straight and branched chain hydrocarbon radicals containing one triple bond and having from 2 to 4 carbon atoms such as, for example, ethynyl, 2-propynyl, 3-butynyl and the like; $C_{2-4}$alkynediyl as a group or part of a group defines bivalent straight and branched chain hydrocarbon radicals containing one triple bond and having from 2 to 4 carbon atoms such as, for example, ethynediyl, 2-propynediyl, 3-butynediyl and the like; $C_{3-7}$cycloalkyl is defined as cyclopropyl, cyclobutyl, cyclopentyl, cyclohexyl and cycloheptyl. The term "C(=O)" refers to a carbonyl and "$SO_2$" to a sulfon.

The term $C_{1-14}$heterocycle defines one or more rings (including 3, 4, 5 or 6 membererd heterocyclic rings) which may be independently saturated, partially saturated, unsaturated, including aromatic, containing 1 to 14 carbon atoms and one or more (for example 1, 2, 3 or 4) heteroatoms selected from N, O and S. Examples of such groups include 1H-pyrazolo[3,4-d]pyrimidinyl, benzimidazolyl, benzodioxolanyl, benzodioxolyl, benzofuranyl, benzopyranyl, benzopyridinyl, benzothiazolyl, benzothienyl, benzoxazolyl, cinnolinyl, dihydrobenzofuranyl, dihydropyrimidinyl, dioxanyl, dioxolanyl, dithianyl, furanyl, imidazo[2,1-b]thiazolyl, imidazolinyl, imidazolyl, indanyl, indolinyl, indolyl, isobenzofuranyl, isobenzothienyl, isoindolyl, isoquinolinyl, isoquinolyl, isothiazolyl, isoxazolyl, morpholinyl, oxadiazolyl, oxazolidinyl, oxazolinyl, oxazolopyridinyl, oxazolyl, phtalazinyl, piperazinyl, piperidinyl, purinyl, pyranyl, pyrazinyl, pyrazolinyl, pyrazolyl, pyridazinyl, pyridinyl, pyrimidinyl, pyrrolidinyl, pyrrolinyl, pyrrolyl, quinazolinyl, quinolinyl, quinoxalinyl, tetrahydrofuranyl, tetrahydropyranyl, tetrahydropyridinyl, tetrazolyl, thiadiazolyl, thiazolinyl, thiazolopyridinyl, thiazolyl, thienyl, thiolanyl, thiomorpholinyl, triazinyl, triazolyl, triazospirodecanyl or trithianyl.

Suitably, $C_{1-14}$heterocycle includes triazolyl, thienyl, quinolinyl, benzothiazolyl, quinoxalinyl, imidazolyl, benzimidazolyl, pyridinyl, pyrimidinyl, pyridazinyl, furanyl, benzofuranyl, furanyl, dihydrobenzofuranyl, benzopyranyl, benzothienyl, pyrrolidinyl, indanyl, benzodioxolanyl, morpholinyl, pyrazinyl and triazinyl.

Said $C_{1-14}$heterocycle may be substituted with one or more substituents selected from substituted or unsubstituted phenyl, trifluoromethyl, trifluoromethyloxy, halo, hydroxy, cyano, nitro, $C_{1-12}$alkyl, $C_{1-12}$alkyloxy, hydroxycarbonyl, $C_{1-6}$alkyloxycarbonyl, amino, aminocarbonyl, furanyl, mono- or di($C_{1-4}$alkyl)amino, thienyl, pyridinyl, mono- or di($C_{1-4}$alkyl)aminocarbonyl, $C_{1-6}$alkylcarbonylamino, substituted or unsubstituted phenylsulfonyl, substituted or unsubstituted phenylcarbonyl and $C_{1-12}$alkyl substituted with one or more substituents selected from substituted or unsubstituted phenyl, pyrazinyl, furanyl and thienyl The term substituted phenyl particularly includes phenyl substituted with one or more substituents selected from trifluoromethyl, trifluoromethyloxy, halo, hydroxy, cyano, nitro, $C_{1-12}$alkyl, $C_{1-12}$alkyloxy, phenyl$C_{1-6}$alkyl, phenyl$C_{1-6}$alkyloxy, phenyloxy, phenylcarbonyl, hydroxycarbonyl, $C_{1-6}$alkyloxycarbonyl, amino, mono- or di($C_{1-4}$alkyl)amino, mono- or di(phenyl)amino, $C_{1-6}$alkylcarbonylamino or phenyl.

In a preferred embodiment of the invention, the group

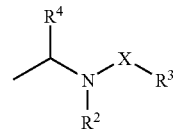

is positioned on the second carbon atom of the triazole ring of formula (I).

As used herein before, the term "one or more" covers the possibility of all the available C-atoms, where appropriate, to be substituted, preferably 1, 2 or 3.

The term prodrug as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, 8$^{th}$ ed., McGraw-Hill, Int. Ed. 1992, "Biotransformation of Drugs", p. 13-15) describing prodrugs generally, is hereby incorporated.

When any variable occurs more than one time in any constituent, each definition is independent.

It will be appreciated that some of the compounds of formula (I) and their prodrugs, N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their prodrugs, N-oxides, addition salts, quaternary amines may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their prodrugs, N-oxides, salts, solvates or quaternary amines substantially free, i.e. associated with less than 10%, preferably less than 5%, in particular less than 2% and most preferably less than 1% of the other isomers. Stereochemically isomeric forms of the compounds of formula (I) are obviously intended to be embraced within the scope of this invention.

References to alkenyl groups, include groups which may be in the E or Z form or a mixture thereof.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to include also the prodrugs, N-oxides, addition salts, quaternary amines and all stereoisomeric forms.

The present invention further includes the compounds of formula (I) wherein one or more of the following restrictions apply:
a) Y is $C_{1-4}$alkanediyl, or a direct bond; or
b) $R^1$ is hydrogen, cyano, aryl or a substituted or unsubstituted $C_{1-4}$heterocycle; or
c) $=Z^1-Z^2=Z^3-$ is a radical of formula (a-1) or (a-2), in particular (a-1); or
d) $R^2$ is aryl, $C_{3-7}$cycloalkyl, $C_{1-12}$alkyl or $C_{1-12}$alkyl substituted with one or more substituents selected from hydroxy, aryl, aryloxy, substituted or unsubstituted $C_{1-14}$heterocycle, hydroxycarbonyl, hydroxy$C_{1-6}$alkyloxy, or aryl$C_{1-6}$alkylthio; or
e) R is aryl; $-NR^5R^6$; substituted or unsubstituted $C_{1-14}$heterocycle or $C_{2-4}$alkenediyl substituted with one or more substituents selected from aryl, and a substituted or unsubstituted $C_{1-14}$heterocycle (in a preferred embodiment said substituted or unsubstituted $C_{1-14}$heterocycle is selected from triazolyl, thienyl, quinolinyl, benzothiazolyl, quinoxalinyl, imidazolyl, benzimidazolyl, pyridinyl, pyrimidinyl, pyridazinyl, furanyl, benzofuranyl, furanyl, dihydrobenzofuranyl, benzopyranyl, benzothienyl, pyrrolidinyl, indanyl, benzodioxolanyl, morpholinyl and triazinyl); or
f) $R^4$ is hydrogen or $C_{1-6}$alkyl; or
g) $R^5$, $R^6$, $R^7$, $R^8$, $R^9$, or X are defined as above.

Another aspect of this invention consists of those compounds of formula (I) wherein one or more of the following restrictions apply:
a) $L^1$ is $R^1-Y-$ wherein $R^1$ is hydrogen, substituted or unsubstituted phenyl (in a preferred embodiment said substituted phenyl is substituted with one or more substituents selected from halo, nitro, cyano, $C_{1-12}$alkyl, $C_{1-12}$alkyloxy, $C_{1-6}$alkyloxycarbonyl, trifluoromethyl, trifluoromethyloxy, and phenyloxy), benzodioxolyl, pyridinyl or pyridinyl substituted with one or more substituents selected from $C_{1-6}$alkyl, hydroxy, halo, cyano, and $C_{1-6}$alkyloxycarbonyl and wherein Y is $C_{1-4}$alkanediyl or a direct bond; or
b) $L^2$ is $R^1-Y-$ wherein $R^1$ is hydrogen, cyano, substituted or unsubstituted phenyl (in a preferred embodiment said substituted phenyl is substituted with one or more substituents selected from halo, nitro, cyano, $C_{1-12}$alkyl, $C_{1-12}$alkyloxy, $C_{1-6}$alkyloxycarbonyl, trifluoromethyl, trifluoromethyloxy, and phenyloxy) and wherein Y is $C_{1-4}$alkanediyl or a direct bond; or
c) $=Z^1-Z^2=Z^3-$ is a radical of formula (a-1);
d) X is $SO_2$, $C(=O)$ or a direct bond; or
e) $R^2$ is aryl or $C_{1-12}$alkyl wherein $C_{1-12}$alkyl may optionally be substituted with one or more substituents selected from aryl and a substituted or unsubstituted $C_{1-14}$heterocycle; or
f) $R^3$ is aryl, a substituted or unsubstituted $C_{1-14}$heterocycle, or a $C_{2-4}$alkenediyl substituted with one or more aryl; or
g) $R^4$ is hydrogen; or
h) $R^5$, $R^6$, $R^7$, $R^8$ or $R^9$ are defined as above.

Another group of compounds of formula (I), are compounds of formula

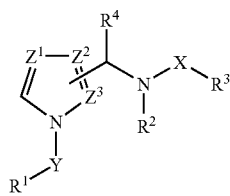

(I-a)

or their prodrugs, N-oxides, addition salts, quaternary amines and stereochemically isomeric forms, wherein X is $SO_2$, $(CH_2)_n$, $C(=O)$ or a direct bond;

Y is $C_{1-4}$alkanediyl, $C_{2-4}$alkenediyl, $C_{2-4}$alkynediyl or $C(=O)$;

$=Z^1-Z^2=Z^3-$ represents a radical of formula

=N—N=CH— (a-1)

=N—CH=N— (a-2) or

=CH—N=N— (a-3);

n is 1 to 4;

$R^1$ is aryl or a substituted or unsubstituted $C_{1-14}$heterocycle;

$R^2$ is aryl, $C_{3-7}$cycloalkyl or $C_{1-12}$alkyl wherein $C_{3-7}$cycloalkyl and $C_{1-12}$alkyl may optionally be substituted with 1 or more substituents selected from hydroxy, aryl, aryloxy, a substituted or unsubstituted $C_{1-14}$heterocycle, $C_{3-7}$cycloalkyl, hydroxycarbonyl, $C_{1-6}$alkyloxycarbonyl, hydroxy$C_{1-6}$alkyl, hydroxy$C_{1-6}$alkyloxy, hydroxy$C_{1-6}$alkylthio or aryl$C_{1-6}$alkylthio;

$R^3$ is aryl or substituted or unsubstituted $C_{1-14}$heterocycle;

$R^4$ is hydrogen, aryl, $C_{3-7}$cycloalkyl or $C_{1-6}$alkyl optionally substituted with $C_{3-7}$cycloalkyl, hydroxycarbonyl, $C_{1-4}$alkyloxycarbonyl or aryl;

aryl is naphthyl or phenyl each of which may optionally be substituted with one or more substituents selected from trifluoromethyl, trifluoromethyloxy, halo, cyano, nitro, $C_{1-12}$alkyl, $C_{1-12}$alkyloxy, phenyl$C_{1-6}$alkyl, phenyl$C_{1-6}$alkyloxy, phenyloxy, phenylcarbonyl, hydroxycarbonyl, $C_{1-6}$alkyloxycarbonyl, amino, mono- or di($C_{1-4}$alkyl)amino, $C_{1-6}$alkylcarbonylamino, substituted or unsubstituted phenyl or a $C_{1-14}$heterocycle.

A group of interesting compounds consists of those compounds of formula (I-a) wherein one or more of the following restrictions apply:

Y is $C_{1-4}$alkanediyl, $C_{1-4}$alkynediyl or C(=O); =$Z^1$-$Z^2$=$Z^3$— is a radical of formula (a-1) or (a-2), in particular (a-1);

$R^1$ is phenyl, benzodioxolyl or pyridinyl wherein said phenyl may optionally be substituted with one or more substituents selected from halo, nitro, cyano, $C_{1-12}$alkyl, $C_{1-12}$alkyloxy, $C_{1-6}$alkyloxycarbonyl, trifluoromethyl; and wherein said pyridinyl may optionally be substituted with one or more substituents selected from $C_{1-6}$alkyl, hydroxy, halo, cyano, $C_{1-6}$alkyloxycarbonyl;

$R^2$ is aryl, $C_{3-7}$cycloalkyl or $C_{1-12}$alkyl wherein $C_{1-12}$alkyl may optionally be substituted with 1 or more substituents selected from hydroxy, aryl, aryloxy, substituted or unsubstituted $C_{1-14}$heterocycle, hydroxycarbonyl, hydroxy$C_{1-6}$alkyloxy, or aryl$C_{1-6}$alkylthio;

$R^3$ is aryl or a substituted or unsubstituted $C_{1-14}$heterocycle selected from triazole, thiophene, quinoline, benzothiazole, quinoxaline, imidazole, benzimidazole, pyridine, pyrimidine and triazine;

$R^4$ is hydrogen.

A particular group of compounds are those compounds of formula (I) wherein $L^1$ is $R^1$—Y— with $R^1$ is hydrogen, phenyl, pyridinyl, phenyl substituted with one or more substituents selected from halo, nitro, cyano, $C_{1-12}$alkyl, and $C_{1-12}$alkyloxy or pyridinyl substituted with one or more substituents selected from $C_{1-6}$alkyl and cyano and wherein Y is $C_{1-4}$alkanediyl; $L^2$ is $R^1$—Y— with R is hydrogen or cyano and wherein Y is $C_{1-4}$alkanediyl or a direct bond; =$Z^1$-$Z^2$=$Z^3$— is a radical of formula (a-1); $R^2$ is aryl, $C_{1-12}$alkyl or $C_{1-12}$alkyl substituted with one or more substituents selected from aryl, and a substituted or unsubstituted $C_{1-14}$heterocycle; $R^3$ is aryl, a substituted or unsubstituted $C_{1-14}$heterocycle selected from quinoline, quinoxaline, benzofuran, furan, dihydrobenzofuran, benzopyran, pyridine, benzothiophene, pyrrolidine, indene, benzodioxolane and thiophene, or a $C_{2-4}$alkenediyl substituted with one or more substituents selected from naphthyl, phenyl and phenyl substituted with one or more substituents selected from halo, cyano, nitro, substituted or unsubstituted phenyl, phenyloxy, trifluoromethyl, methoxy, thienyl, trifluoromethyloxy, morpholinyl and $C_{1-12}$alkyl; $R^4$ is hydrogen.

Particular compounds are those compounds of formula (I) wherein $L^1$ is substituted or unsubstituted benzyl, more in particular, p-cyano-benzyl and $L^2$ is hydrogen.

Other particular compounds are those compounds of formula (I) wherein at least one of the substituents $R^2$ and —X—$R^3$ is p-phenoxy-phenyl or p-(phenylcarbonyl)-phenyl.

Also particular compounds are those compounds of formula (I) wherein —X—$R^3$ is arylsulfonyl.

Further particular compounds are those compounds of formula (I) wherein $R^3$ is $C_{2-4}$alkenediyl substituted with a substituted or unsubstituted $C_{1-14}$heterocycle or wherein $R^3$ is piperidinyl substituted with arylsulfonyl.

Also particular compounds are those compounds of formula (I) wherein —$NR^5R^6$ is arylamino.

Yet another particular group of compounds are those compounds of formula (I) wherein $R^2$ is $C_{1-12}$alkyl substituted with aryl.

A group of particularly interesting compounds of formula (I) are

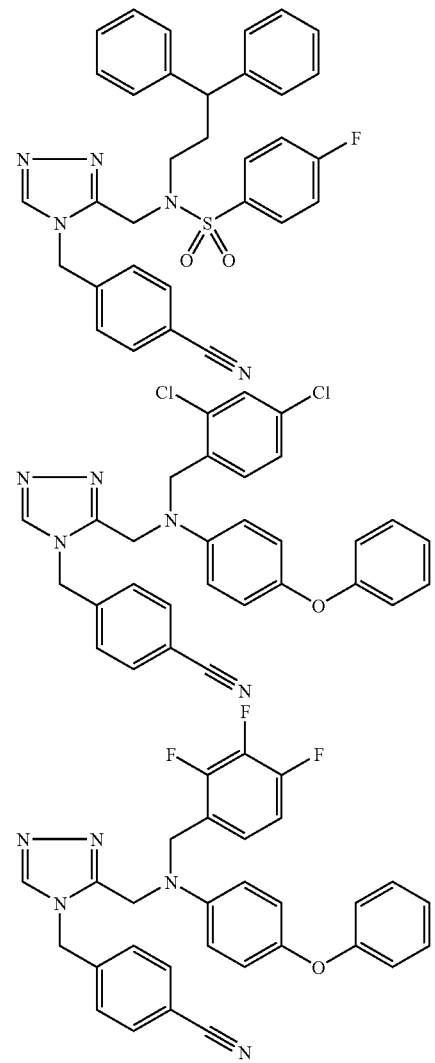

-continued
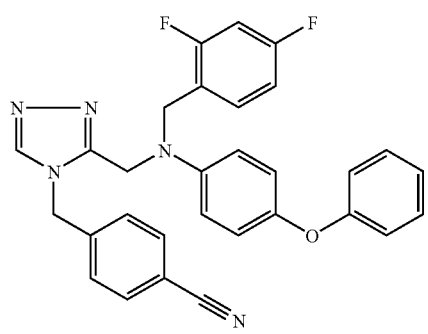
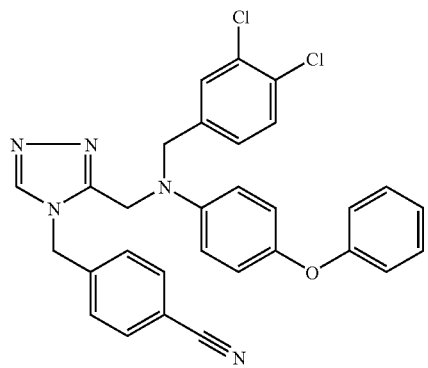
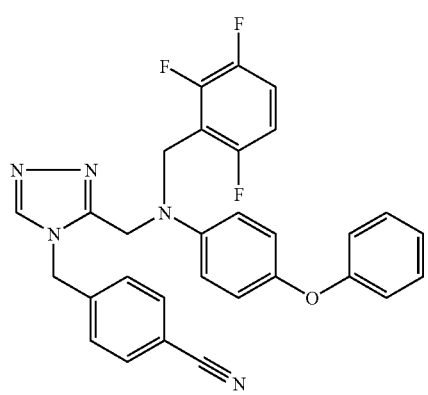
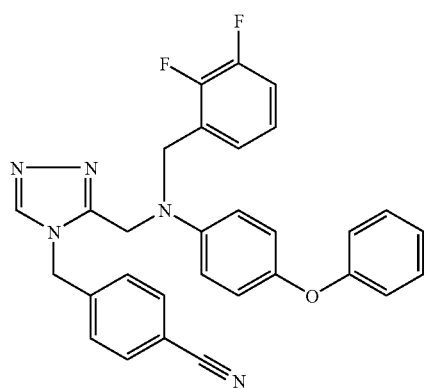
-continued
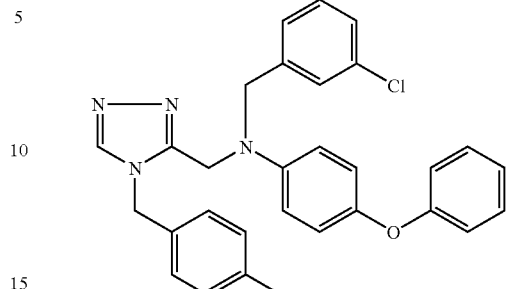
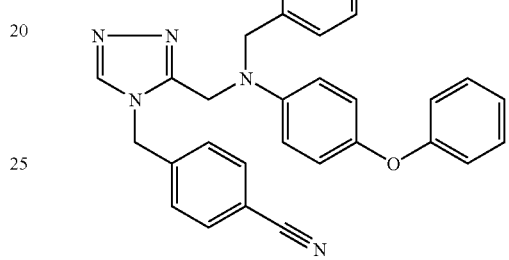
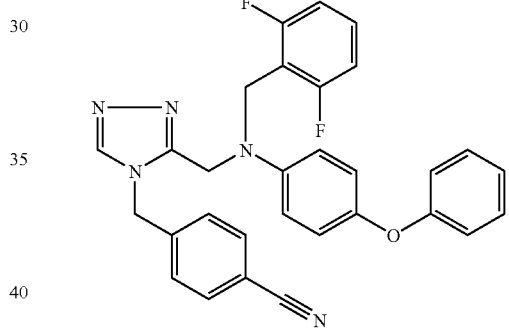
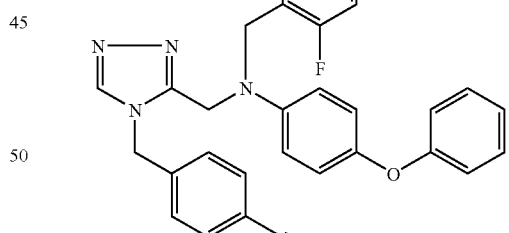
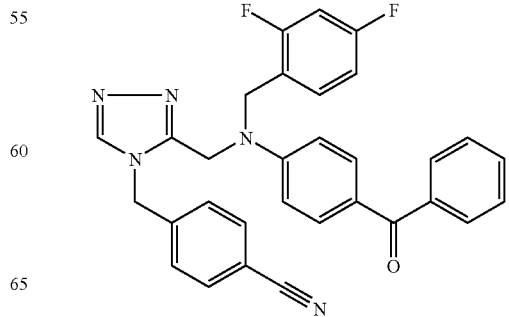

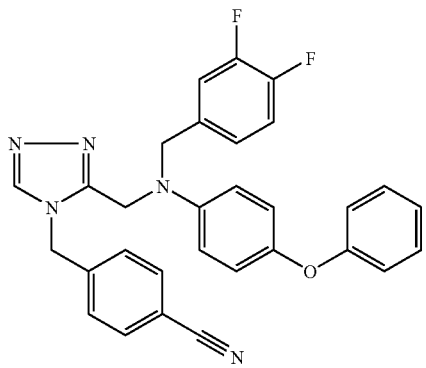
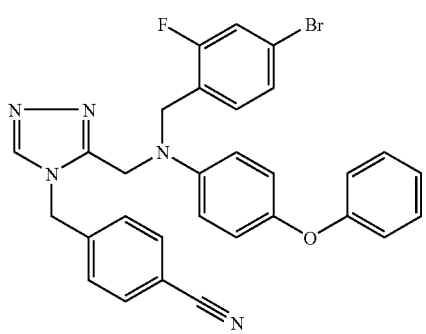
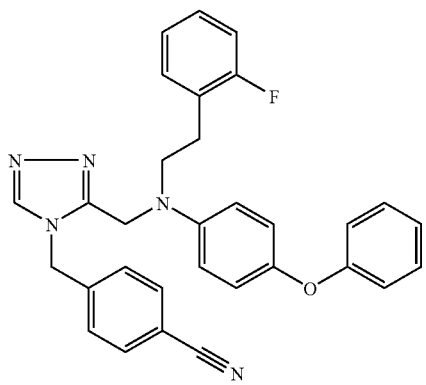
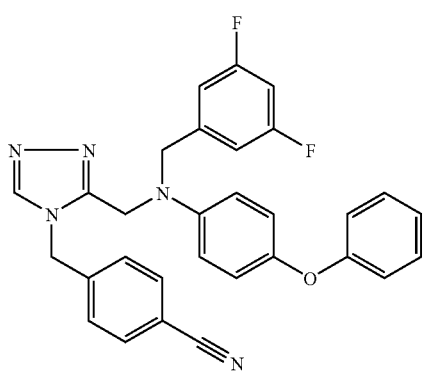
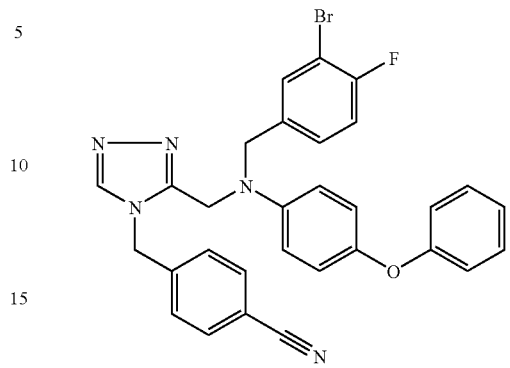
a prodrug, N-oxide, addition salt, quaternary amine or stereochemically isomeric form thereof.
The most preferred compounds of formula (I) are
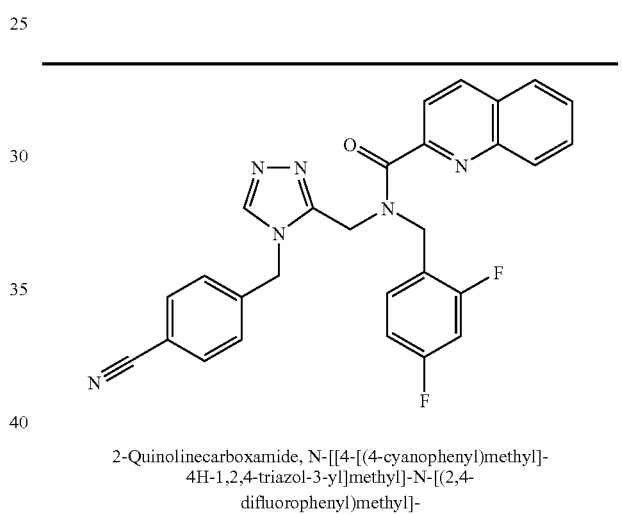
2-Quinolinecarboxamide, N-[[4-[(4-cyanophenyl)methyl]-
4H-1,2,4-triazol-3-yl]methyl]-N-[(2,4-
difluorophenyl)methyl]-
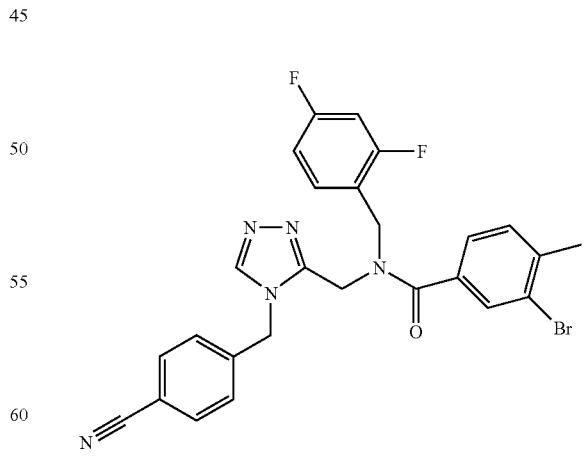
Benzamide, 3-bromo-N-[[4-[(4-cyanophenyl)methyl]-4H-
1,2,4-triazol-3-yl]methyl]-N-[(2,4-difluorophenyl)methyl]-4-
methyl- -continued

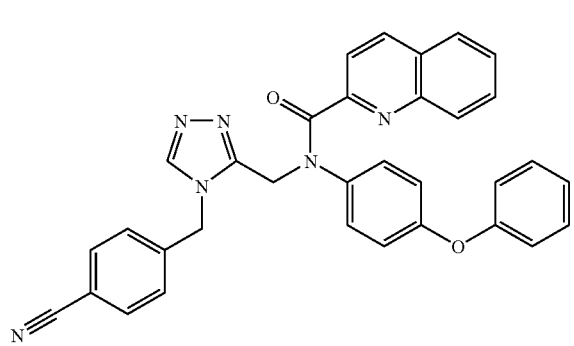

2-Quinolinecarboxamide, N-[[4-[(4-cyanophenyl)methyl]-
4H-1,2,4-triazol-3-yl]methyl]-N-(4-phenoxyphenyl)-

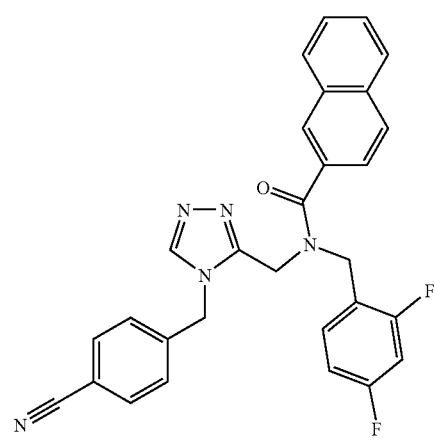

2-Naphthalenecarboxamide, N-[[4-[(4-cyanophenyl)methyl]-
4H-1,2,4-triazol-3-yl]methyl]-N-[(2,4-
difluorophenyl)methyl]

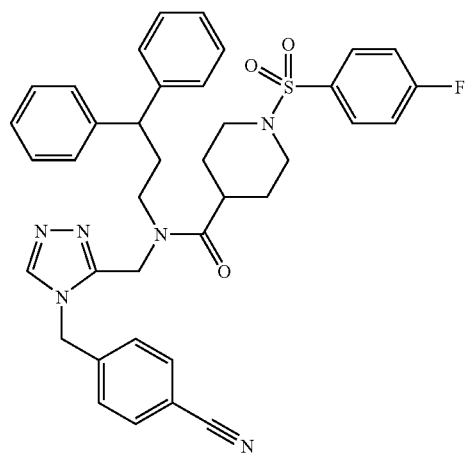

4-Piperidinecarboxamide, N-[[4-[(4-cyanophenyl)methyl]-
4H-1,2,4-triazol-3-yl]methyl]-N-(3,3-diphenylpropyl)-1-
[(4-fluorophenyl)sulfonyl]-

-continued

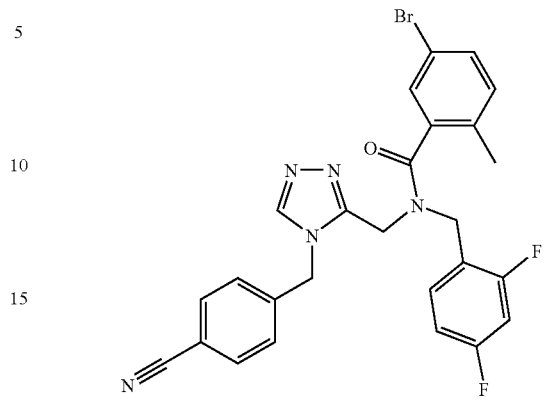

Benzamide, 5-bromo-N-[[4-[(4-cyanophenyl)methyl]-4H-
1,2,4-triazol-3-yl]methyl]-N-[(2,4-difluorophenyl)methyl]-2-
methyl-

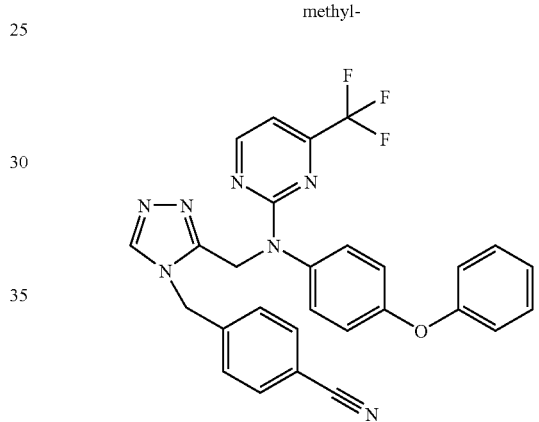

Benzonitrile, 4-[[3-[[[(4-phenoxyphenyl)[4-
(trifluoromethyl)-2-pyrimidinyl]]amino]methyl-4H-
1,2,4-triazol-4-yl]methyl]-

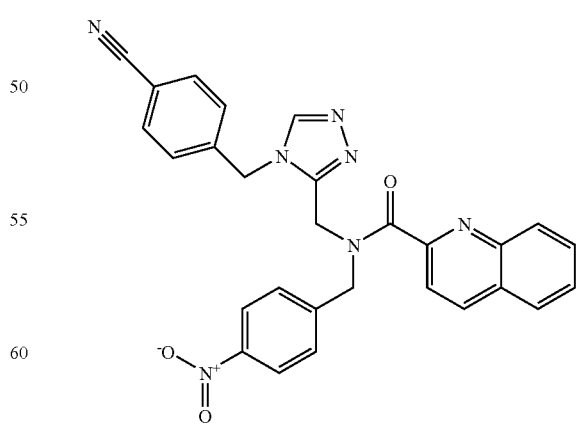

2-Quinolinecarboxamide, N-[[4-[(4-cyanophenyl)methyl]-
4H-1,2,4-triazol-3-yl]methyl]-N-[(4-nitrophenyl)methyl]-

-continued

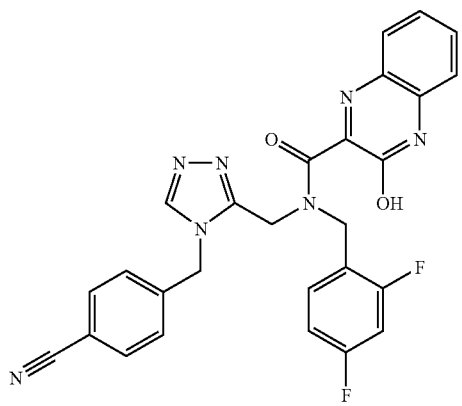

2-Quinoxalinecarboxamide, N-[[4-[(4-cyanophenyl)methyl]-4H-1,2,4-triazol-3-yl]methyl]-N-[(2,4-difluorophenyl)methyl]-3-hydroxy-

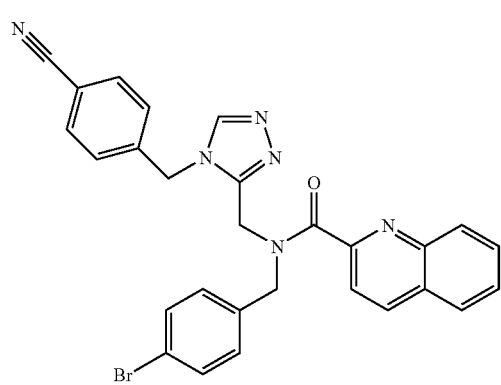

2-Quinolinecarboxamide, N-[(4-bromophenyl)methyl]-N-[[4-[(4-cyanophenyl)methyl]-4H-1,2,4-triazol-3-yl]methyl]-

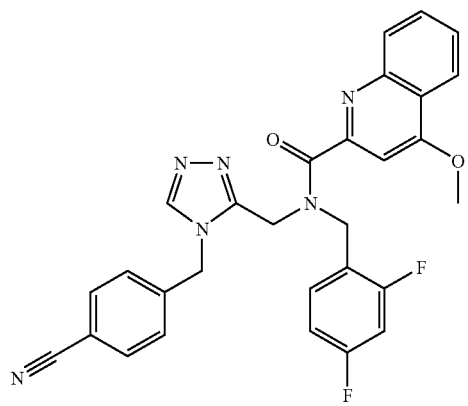

2-Quinolinecarboxamide, N-[[4-[(4-cyanophenyl)methyl]-4H-1,2,4-triazol-3-yl]methyl]-N-[(2,4-difluorophenyl)methyl]-4-methoxy- -continued

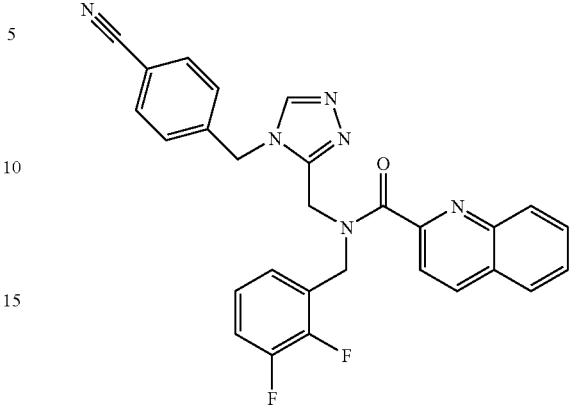

2-Quinolinecarboxamide, N-[[4-[(4-cyanophenyl)methyl]-4H-1,2,4-triazol-3-yl]methyl]-N-[(2,3-difluorophenyl)methyl]-

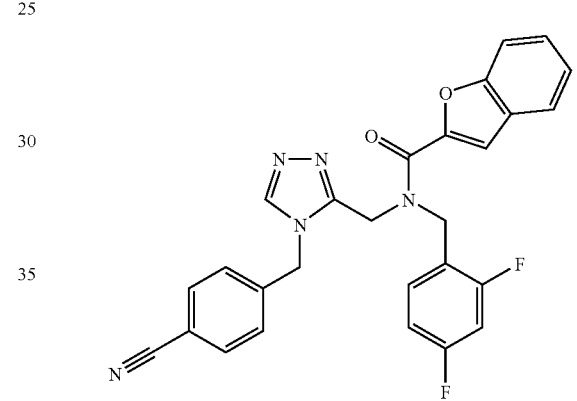

2-Benzofurancarboxamide, N-[[4-[(4-cyanophenyl)methyl]-4H-1,2,4-triazol-3-yl]methyl]-N-[(2,4-difluorophenyl)methyl]-

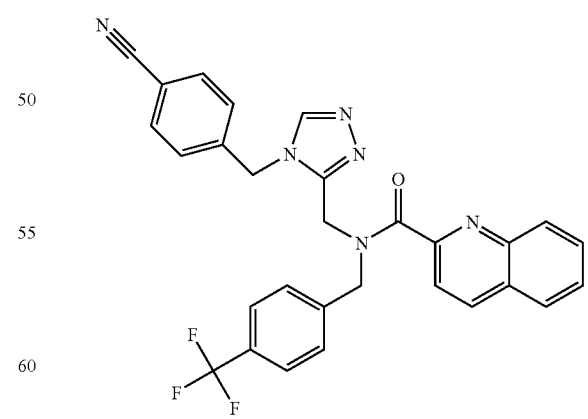

2-Quinolinecarboxamide, N-[[4-[(4-cyanophenyl)methyl]-4H-1,2,4-triazol-3-yl]methyl]-N-[[4-(trifluoromethyl)phenyl]methyl]-

-continued

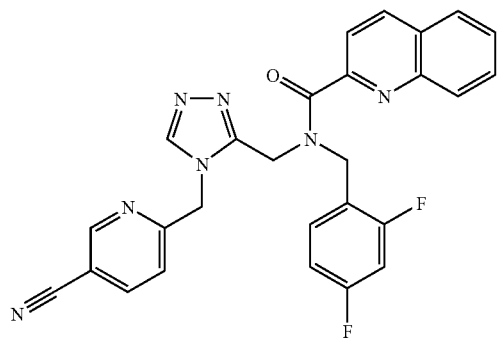

2-Quinolinecarboxamide, N-[[4-[(5-cyano-2-pyridinyl)methyl]-4H-1,2,4-triazol-3-yl]methyl]-N-[(2,4-difluorophenyl)methyl]-

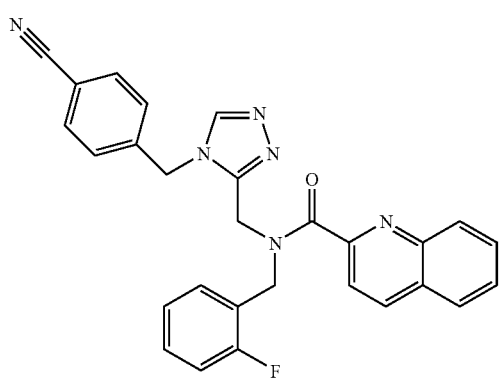

2-Quinolinecarboxamide, N-[[4-[(4-cyanophenyl)methyl]-4H-1,2,4-triazol-3-yl]methyl]-N-[(2-fluorophenyl)methyl]-

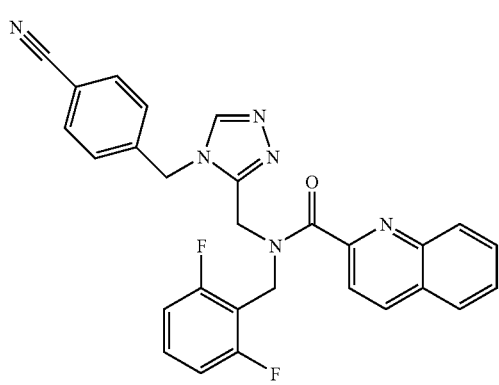

2-Quinolinecarboxamide, N-[[4-[(4-cyanophenyl)methyl]-4H-1,2,4-triazol-3-yl]methyl]-N-[(2,6-difluorophenyl)methyl]-

-continued

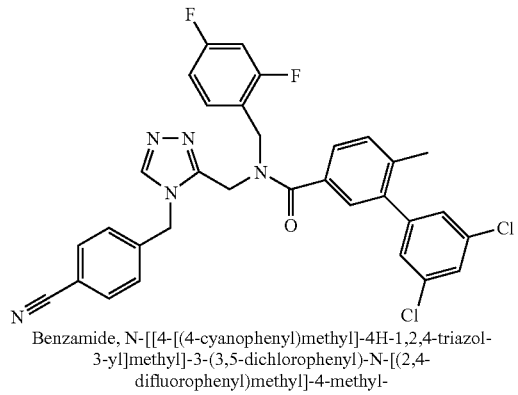

Benzamide, N-[[4-[(4-cyanophenyl)methyl]-4H-1,2,4-triazol-3-yl]methyl]-3-(3,5-dichlorophenyl)-N-[(2,4-difluorophenyl)methyl]-4-methyl-

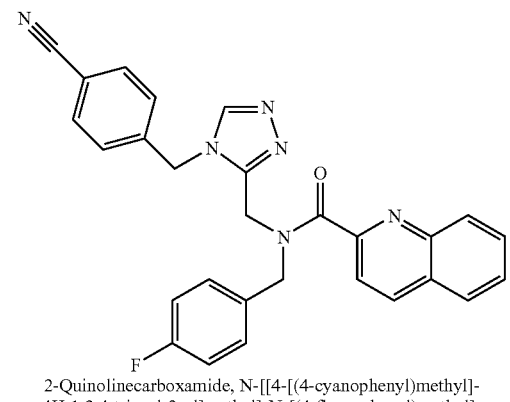

2-Quinolinecarboxamide, N-[[4-[(4-cyanophenyl)methyl]-4H-1,2,4-triazol-3-yl]methyl]-N-[(4-fluorophenyl)methyl]-

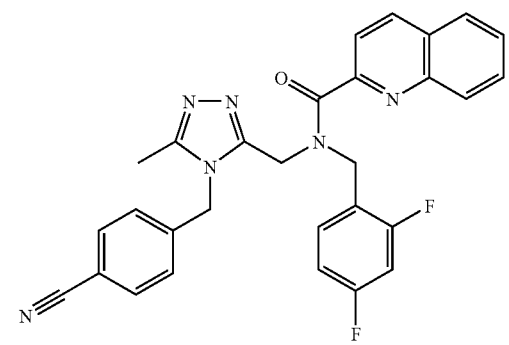

2-Quinolinecarboxamide, N-[[4-[(2-cyanophenyl)methyl]-5-methyl-4H-1,2,4-triazol-3-yl]methyl]-N-[(2,4-difluorophenyl)methyl]-

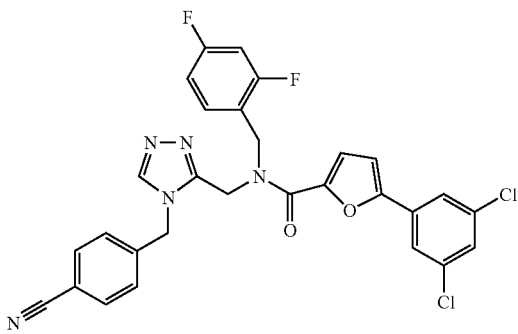

2-Furancarboxamide, N-[[4-[(4-cyanophenyl)methyl]-4H-1,2,4-triazol-3-yl]methyl]-5-(3,5-dichlorophenyl)-N-[(2,4-difluorophenyl)methyl]-

-continued

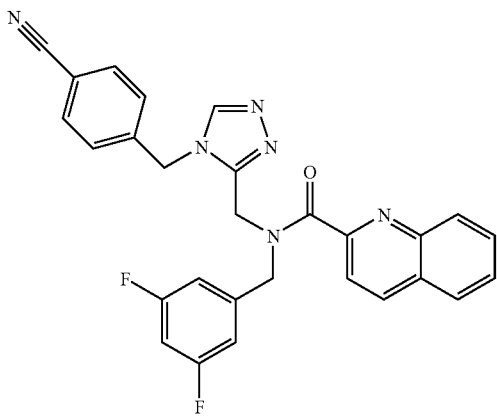

2-Quinolinecarboxamide, N-[[4-[(4-cyanophenyl)methyl]-4H-1,2,4-triazol-3-yl]methyl]-N-[(3,5-difluorophenyl)methyl]- in for example "The Combinatorial Index" (B. Bunin, Academic Press) and Novabiochem's 1999 Catalogue & Peptide Synthesis Handbook (Novabiochem AG, Switzerland) both incorporated herein by reference.

Along with the identification of the appropriate solvent, concentration and temperature, the selection of solid support may influence the course of the reaction. The compounds of the present invention were all prepared using 2-chlorotrityl chloride resin (Novabiochem AG, Switzerland). Hereinafter, said resin will be depicted as

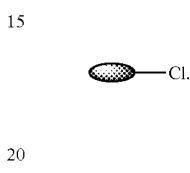

The compounds of the present invention wherein $R^4$ is hydrogen and $=Z^1-Z^2=Z^3-$ is a radical of formula (a-1), said compounds being represented by formula (I-a-1-a) can be prepared according to the following general reaction scheme A.

Scheme A

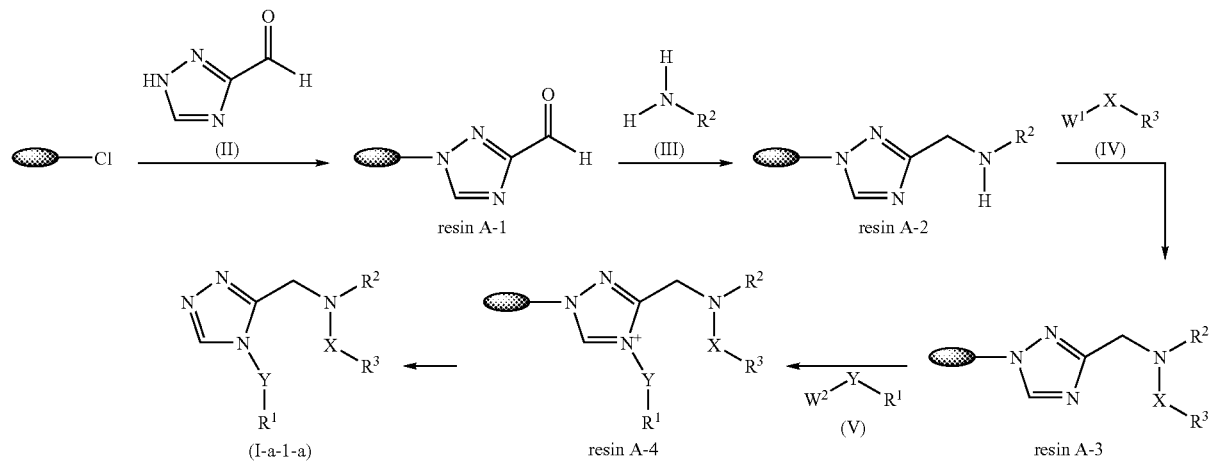

a prodrug, N-oxide, addition salt, quaternary amine or stereochemnically isomeric form thereof.

The compounds of formula (I) can conveniently be prepared using solid phase synthesis techniques. In general, solid phase synthesis involves reacting an intermediate in a synthesis with a polymer support. This polymer supported intermediate can then be carried on through a number of synthetic steps. After each step, impurities are removed by filtering the resin and washing it numerous times with various solvents. At each step the resin can be split up to react with various intermediates in the next step thus allowing for the synthesis of a large number of compounds. After the last step in the procedure the resin is treated with a reagent or process to cleave the resin from the sample. More detailed explanation of the techniques used in solid phase chemistry are described Step 1: The 2-chlorotrityl chloride resin is reacted with 1(H)-1,2,4-triazole-3-carboxaldehyde in a suitable solvent such as, for example, N,N-dimethylformamide, 1,2-dichloroethane, N-ethyl-N-(1-methylethyl)-2-propanamine, dimethylacetamide, triethylamine, dichloromethane or a mixture thereof. Heating, stirring and the use of an inert atmosphere such as a nitrogen atmosphere may enhance the reaction. After reaction, the resulting resin A-1 may be washed, rinsed and dried using conventional techniques. For instance, the resin A-1 may be washed with N,N-dimethylformamide, dimethylacetamide, methanol, tetrahydrofuran or a mixture thereof, rinsed with $CH_2Cl_2$ and dried in vacuo.

Step 2: The resin A-1 is reacted with an amine of formula (III) in a suitable solvent such as, for example, 1,2-dichloroethane or dichloromethane, in the presence of an acid such as, for example, acetic acid or formic acid and in the presence of a reducing agent such as, for example, sodium triacetoxyborohydride or sodium cyanoborohydride. Heating, stirring and/or sonification and the use of an inert atmosphere such as a nitrogen atmosphere may enhance the reaction. After reaction, the resulting resin A-2 may be washed, rinsed and dried using conventional techniques.

Step 3: Resin A-2 is reacted with an intermediate of formula (IV) wherein $W^1$ may be a leaving group and X may be a carbonyl group, a sulfonyl group, a direct bond or in case $R^3$ is to be connected to the nitrogen atom via a methylene group (ie. X is a methylene in resin A-3), $W^1$ may also be a formyl moiety. Suitable leaving groups are for instance a halogen, a hydroxy group, trifluoromethanesulfonate, methoxy, methylthio. In case $W^1$ is a formyl group, resin A-2 may be reductively N-alkylated according to the procedure described in step 2. In case $W^1$ is a leaving group, the reaction may be performed in a suitable solvent such as for example, dioxane, 1,2-dichloroethane, dichloromethane, tetrahydrofuran, N,N-dimethylformamide, dimethylacetamide conveniently in the presence of an appropriate base such as, for example, sodium tert-butoxide, triethylamine, cesium carbonate, N-ethyl-N-(1-methylethyl)-2-propanamine, and also conveniently in the presence of other reagents like coupling agents, reducing agents, Pd-ligands, catalysts such as, for example, tris(dibenzylideneacetone)dipalladium (0), [1,1'-binaphthalene]-2,2'-diylbis[diphenyl]-phosphine, 1-[bis(dimethylamino)methylene]-hexafluorophosphate(1−)-1H-benzotriazolium, 3-oxide, β-methyl-α,α-diphenyl-1-piperidineethanol, tributylphosphine, palladium (II) acetate, tri-o-tolylphosphine, (1-hydroxy-1H-benzotriazolato-O)tri-1-pyrrolidinyl-(T-4)-hexafluorophosphate(1−)-phosphorus(1+), 1-[bis(dimethylamino)-methylene]-hexafluorophosphate(1−)-1H-1,2,3-triazolo[4,5-b]pyridinium 3-oxide, 1-hydroxy-7-azabenzotriazole, diisopropylcarbodiimide. In case X in resin A-3 is an amide or thioamide moiety, W1 may be a carbonyl or thiocarbonyl whereby X is a nitrogen atom connected to W with a double bond (ie. W1-X is an isocyanate or isothiocyanate). Heating, stirring and/or sonification and the use of an inert atmosphere such as a nitrogen atmosphere may enhance the reaction. After reaction, the resulting resin A-3 may be washed, rinsed and dried using conventional techniques.

Step 4: Resin A-3 is reacted with an intermediate of formula (V) wherein $W^2$ is a suitable leaving group such as, for example, hydroxy, halogen, trifluoromethanesulfonate. The reaction may be performed in a suitable solvent such as, for example, $CH_2Cl_2$, 1,2-dichloroethane, conveniently in the presence of other reagents like base, sulfonating agent, catalyst such as, for example, N-ethyl-N-(1-methylethyl)-2-propanamine, trifluoroacetic acid anhydride. It may be necessary to cool the reaction temperature to for example −78° C. Stirring and/or sonification and the use of an inert atmosphere such as a nitrogen atmosphere may enhance the reaction. After reaction, the resin A-4 may be washed with a suitable solvent such as methylene chloride, 1,2-dichloroethane etc. and dried using conventional techniques.

Step 5: The resin in Resin A-4 was cleaved using art-known cleaving techniques such as, for example, using a mixture of trifluoroacetic acid and $CH_2Cl_2$.

The compounds of the present invention wherein $R^4$ is hydrogen and $=Z^1-Z^2=Z^3-$ is a radical of formula (a-2), said compounds being represented by formula (I-a-2-a) can be prepared according to the following general reaction scheme B.

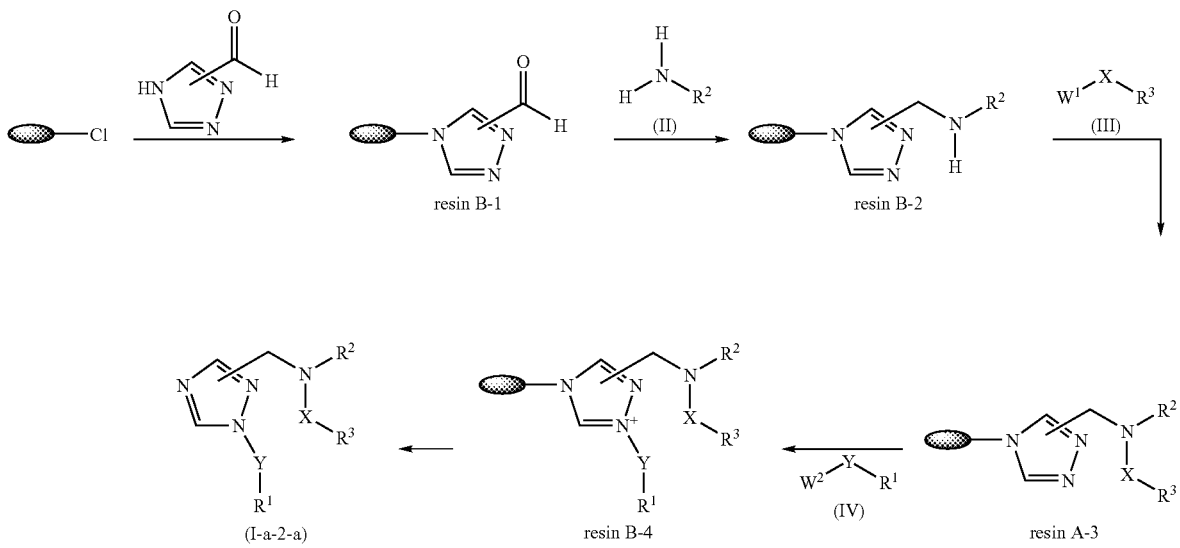

Scheme B resin B-1 resin B-2

(I-a-2-a)

resin B-4 resin A-3

The reaction procedures of the different steps in scheme B are analogous to the reaction steps described for scheme A.

The compounds of the present invention wherein $R^4$ is hydrogen and $=Z^1-Z^2=Z^3-$ is a radical of formula (a-3), said compounds being represented by formula (I-a-3-a) can be prepared according to the following general reaction scheme C.

Scheme C

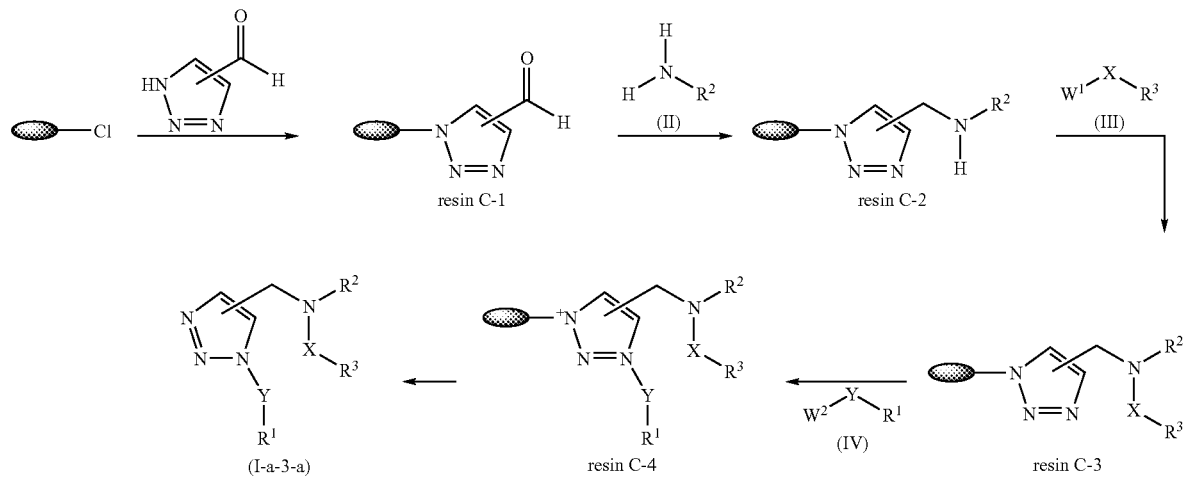

The reaction procedures of the different steps in scheme C are analogous to the reaction steps described for scheme A.

The compounds of the present invention wherein $R^4$ is aryl, $C_{3-7}$cycloalkyl or $C_{1-6}$alkyl, said subgroup of $R^4$ being represented by $R^{4'}$, and $=Z^1-Z^2=Z^3-$ is a radical of formula (a-1), said compounds being represented by formula (I-a-1-b) can be prepared according to the following general reaction scheme D.

Step 1: This step is analogous to step 1 in scheme A.

Step 2: The resin D-1 is reacted with a Grignard reagent of formula (VI) in a suitable solvent such as, for example, tetrahydrofuran and diethylether. Stirring and the use of an inert atmosphere such as a nitrogen atmosphere may enhance the reaction. After reaction, the resulting resin D-2 may be washed, rinsed and dried using conventional techniques.

Scheme D

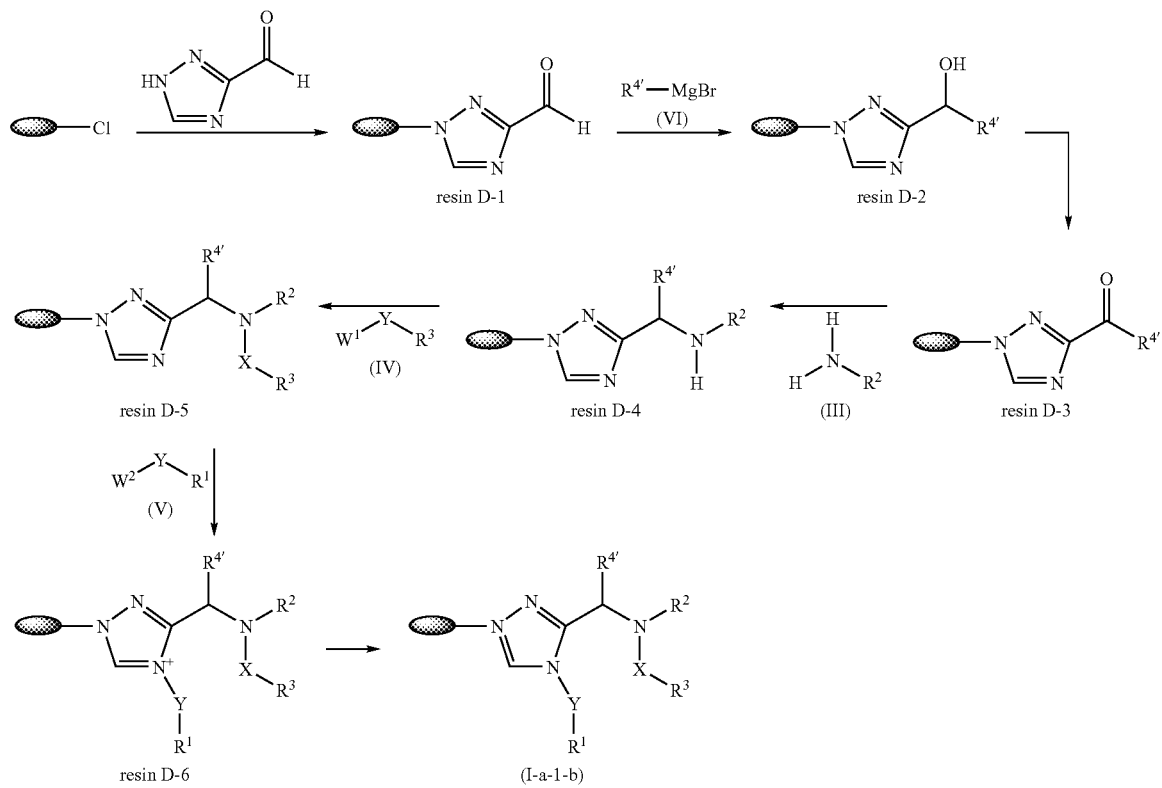

Step 3: The resin D-2 is reacted with an appropriate oxidizing reagent such as, for example, 2-iodoxybenzoic acid, Dess-Martin 12-I-5 preiodinane reagent, 1,1,1-tris(acetyloxy)-1,1-dihydro-1,2-benziodoxol-3(1H)-one, in a suitable solvent such as, for example, dimethylsulfoxide and methylene chloride. Stirring and the use of an inert atmosphere such The compounds of the present invention wherein $R^4$ is substituted $C_{1-6}$alkyl, said subgroup of $R^4$ being represented by $R^{4''}$, and $=Z^1-Z^2=Z^3-$ is a radical of formula (a-1), said compounds being represented by formula (I-a-1-c) can be prepared according to the following general reaction scheme E.

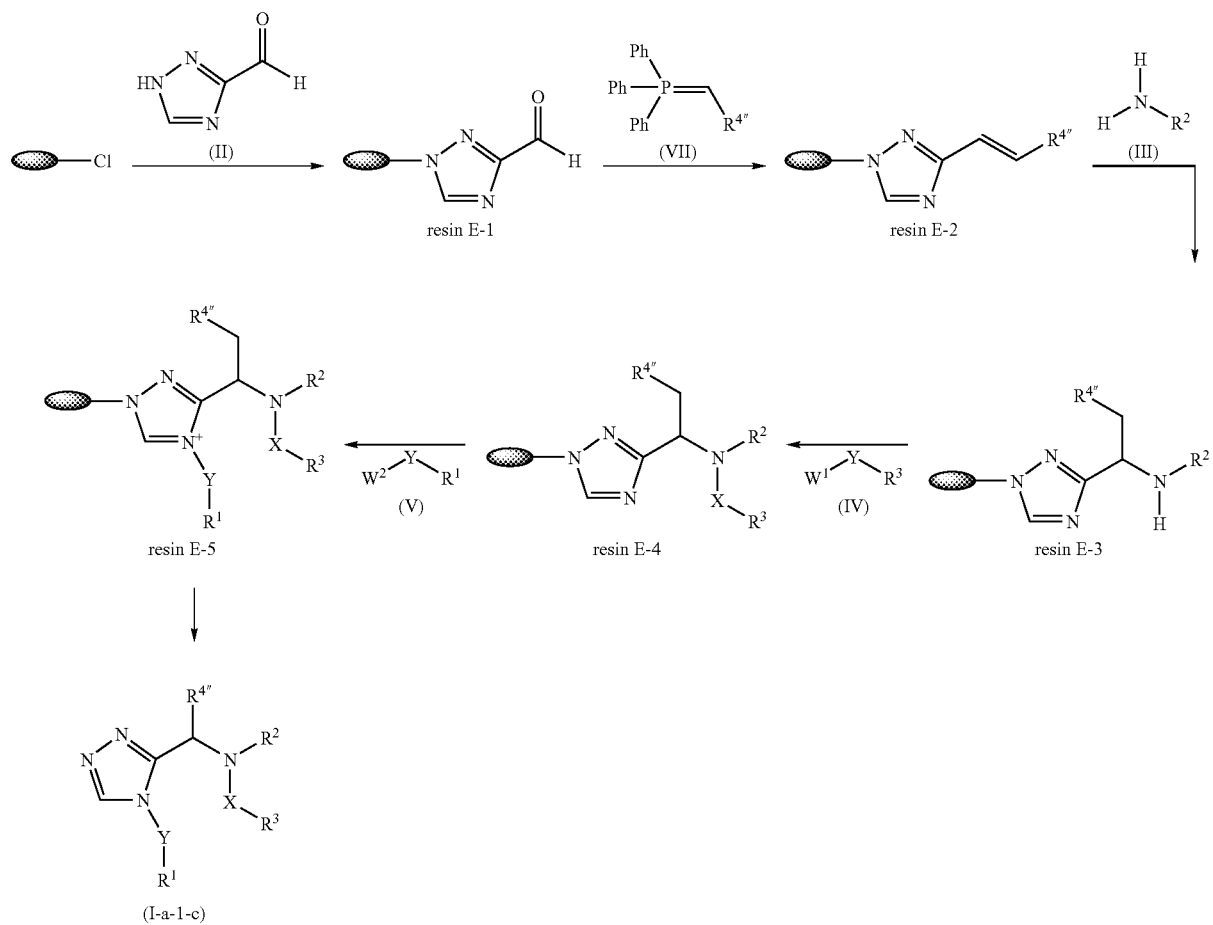

as a nitrogen atmosphere may enhance the reaction. However, caution should be used when using potentially explosive hypervalent iodine compounds such as the ones mentioned above. After reaction, the resulting resin D-3 may be washed, rinsed and dried using conventional techniques.

Subsequent steps: The subsequent steps were performed analogous to steps 2, 3, 4 & 5 in scheme A.

The compounds of the present invention wherein $R^4$ is limited to the subgroup $R^{4'}$ and $=Z^1-Z^2=Z^3-$ is a radical of formula (a-2), said compounds being represented by formula (I-a-2-b) can be prepared analogous to the general reaction scheme E but replacing of 1H-1,2,4-triazole-3-carboxaldehyde by the triazole used in scheme B.

The compounds of the present invention wherein $R^4$ is limited to the subgroup $R^{4'}$ and $=Z^1-Z^2=Z^3-$ is a radical of formula (a-3), said compounds being represented by formula (I-a-3-b) can be prepared analogous to the general reaction scheme E but replacing of 1H-1,2,4-triazole-3-carboxaldehyde by the triazole used in scheme B.

Step 1: This step is analogous to step 1 in scheme A.

Step 2: The resin E-1 is reacted with a Wittig reagent of formula (VII) in a suitable solvent such as, for example, tetrahydrofuran, dioxane, ether and 1,2-dimethoxy-ethane. Stirring and the use of an inert atmosphere such as a nitrogen atmosphere may enhance the reaction. After reaction, the resulting resin E-2 may be washed, rinsed and dried using conventional techniques.

Step 3: The resin E-2 is reacted with an intermediate of formula (III) in the presence of a base such as, for example, n-butyllithium, potassium tert-butoxide, sodium hydride, potassium hydride, and in a suitable solvent such as, for example, tetrahydrofuran, dioxane and 1,2-dimethoxyethane. Stirring and the use of an inert atmosphere such as a nitrogen atmosphere may enhance the reaction. After reaction, the resulting resin E-3 may be washed, rinsed and dried using conventional techniques.

Subsequent steps: The subsequent steps were performed analogous to steps 3, 4 & 5 in scheme A.

The compounds of the present invention wherein $R^4$ is limited to the subgroup $R^{4"}$ and $=Z^1-Z^2=Z^3-$ is a radical of formula (a-2), said compounds being represented by formula (I-a-2-c) can be prepared analogous to the general reaction scheme E but replacing of 1H-1,2,4-triazole-3-carboxaldehyde by the triazole used in scheme B.

The compounds of the present invention wherein $R^4$ is limited to the subgroup $R^{4"}$ and $=Z^1-Z^2=Z^3-$ is a radical of formula (a-3), said compounds being represented by formula (I-a-3-c) can be prepared analogous to the general reaction scheme E but replacing of 1H-1,2,4-triazole-3-carboxaldehyde by the triazole used in scheme C.

The compound of the present invention represented by formula (I-a-1-f) wherein $R^{10}$ is a cycloalkyl, methylenecycloalkyl, aryl or a $C_{1-14}$hereocycle wherein said $C_{1-14}$hereocycle preferably contains nitrogen, optionally substituted with a protecting group, as heteroatom; and $=Z^1-Z^2=Z^3-$ is a radical of formula (a-1), said compounds can be prepared according to the following reaction scheme H.

Except for steps 4 & 5, all steps in the above scheme H are conducted in a similar manner as described for equivalent intermediates in Scheme A.

Step 4: The resin H-3 is treated with a deprotecting reagent as may be well known in art such as cesium fluoride, tetrabutylammonium fluoride, piperidine etc. After reaction, the resulting resin H-4 may be washed, rinsed and dried using conventional techniques.

Step 5: The resin H-4 is reacted with a reagent of formula V, wherein reagent V is defined in the same way as reagent IV in Scheme A. The reaction procedure is also similar as step 3 in general reaction Scheme A.

Variations to the above mentioned schemes A, B, C, D, E and H are possible. For instance, it may be convenient to build the chemical groups defined in $R^2$ and $R^3$ in different steps. The synthesis schemes F and G below exemplify possible methods for such.

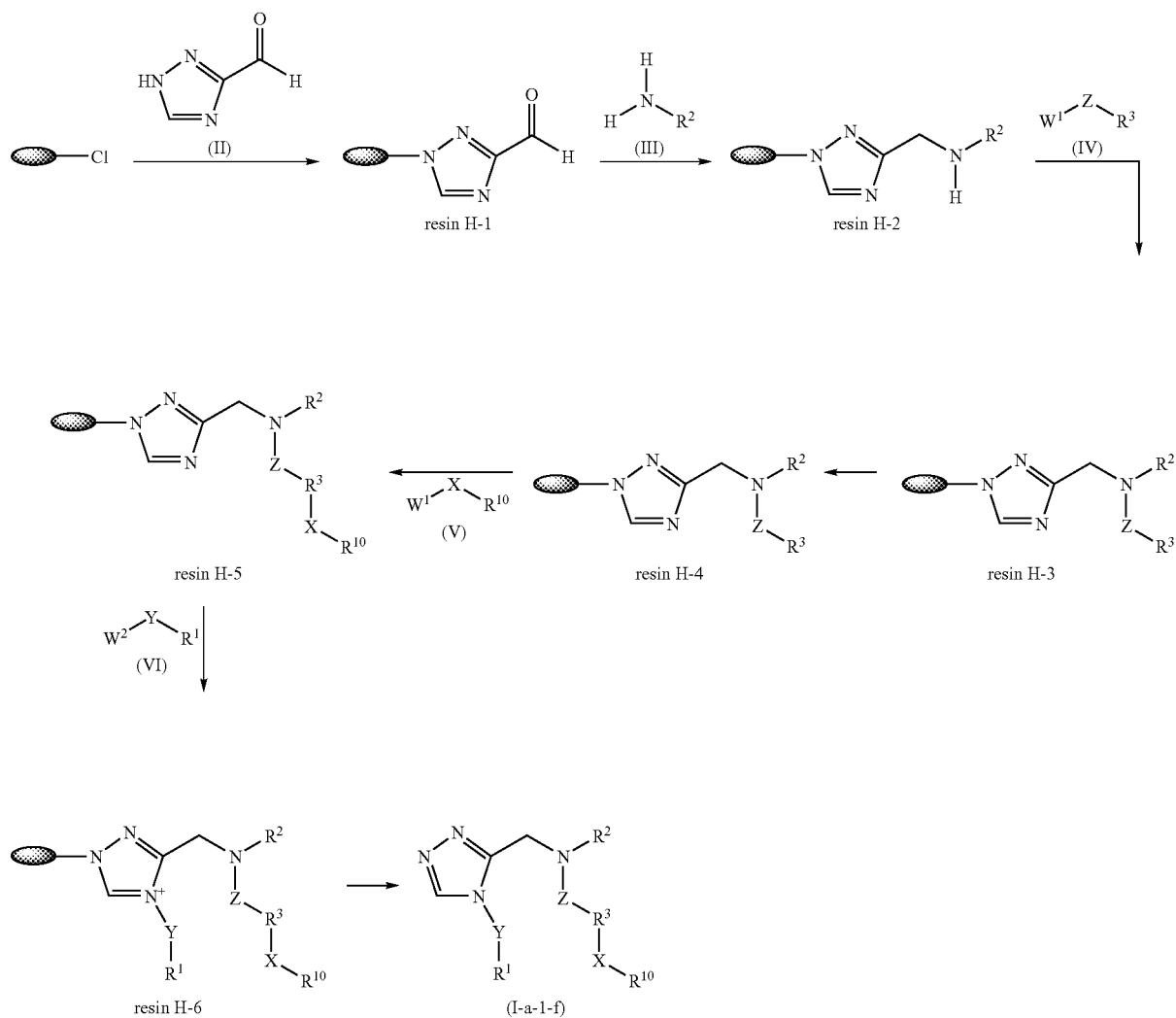

Scheme F

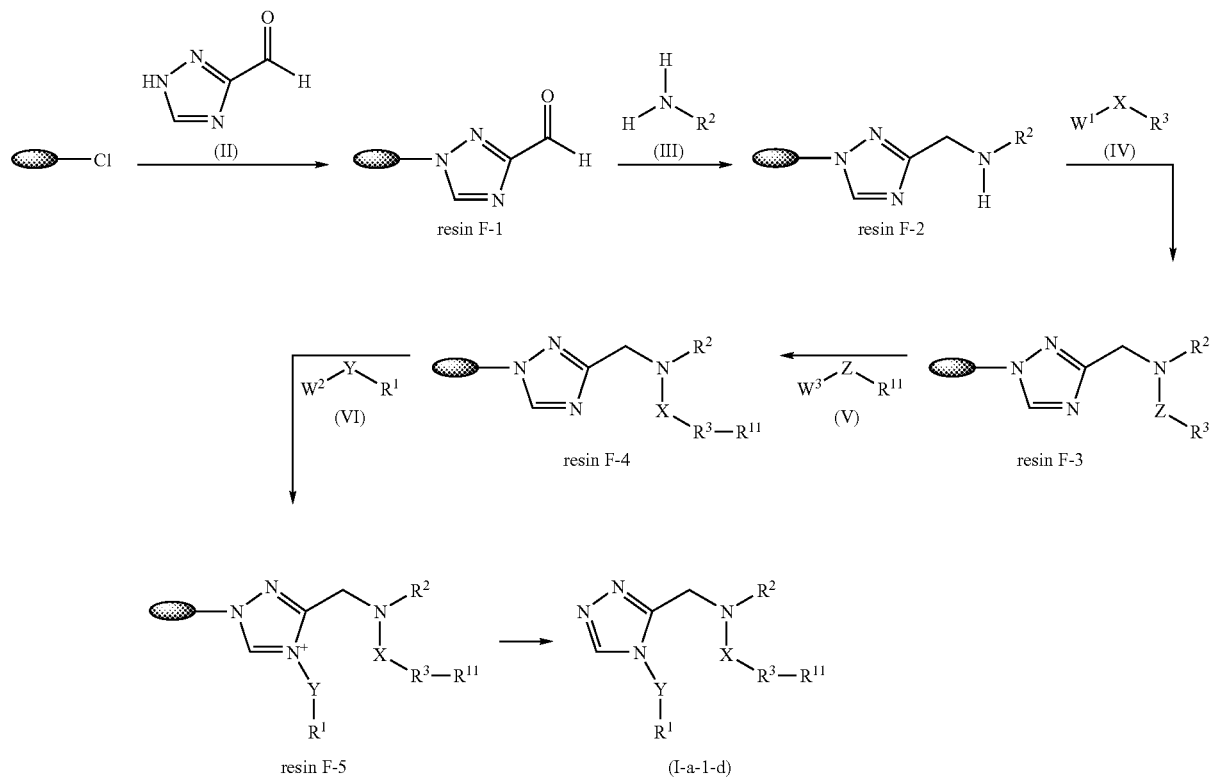

In the above scheme for example, reagent W¹—X—R³ is the same as reagent IV in Scheme A with the stipulation that R³ be an aryl or heteroaryl group additionally substituted with a halogen. Reagent V may be an aryl boronic acid {Ar—B(OH)₂}, a terminal acetylene, an olefin, a secondary amine, a phenol or other hydroxy containing compound. Such reaction is conducted in the presence of a Pd-ligand and/or organometallic catalysts such as tris(dibenzylideneacetone)dipalladium (0), tetrakis(triphenylphosphine) palladium (0), [1,1'-binaphthalene]-2,2'-diylbis[diphenyl]-phosphine, bis(triphenylphosphine)palladium dichloride, dichloro biscyanophenyl palladium (0), tri-tertbutylphosphine, copper (I) iodide, copper (II) chloride, Palladium (II) acetate, tri-o-tolylphosphine, 1,4-bis(diphenylphosphino)butane (dppb), dichlorobis(triphenylphosphine)palladium etc. Such reactions are well described in literature and are frequently referred to as Suzuki, Sonogashira, Buchwald or Heck reactions. Reviews on such reactions are available eg. Palladium catalysis in the synthesis of medicinal agents. Larsen, Robert D. Curr. Opin. Drug Discovery Dev. (1999), 2(6), 651-667. A comprehensive review of the applications of transition metal-catalyzed reactions to solid phase synthesis. Kingsbury, Celia L.; Mehrman, Steven J.; Takacs, James M. Curr. Org. Chem. (1999), 3(5), 497-555. These reactions may be conducted in a suitable solvent such as toluene, dioxane, dimethoxyethane etc. In the structure I-a-1-D, the group R¹¹ is therefore an aryl, heteroaryl, aminocycloalkyl, amino subst alkyl, aryl acetylene, carbonylaryl, etc. All steps in above Scheme F except step 4 are conducted in a similar manner as described for equivalent intermediates in Scheme A. Steps 3a and 3b in example A5 further exemplify this synthesis route.

Further variations to the general reaction schemes A, B, C, D, E and H can be achieved following reaction scheme G.

Scheme G

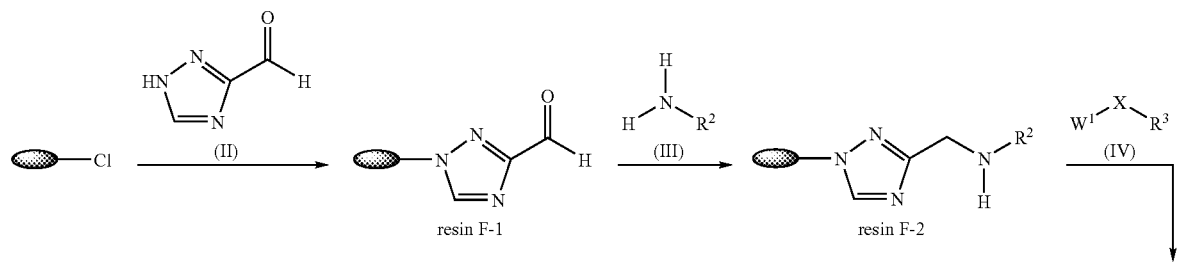

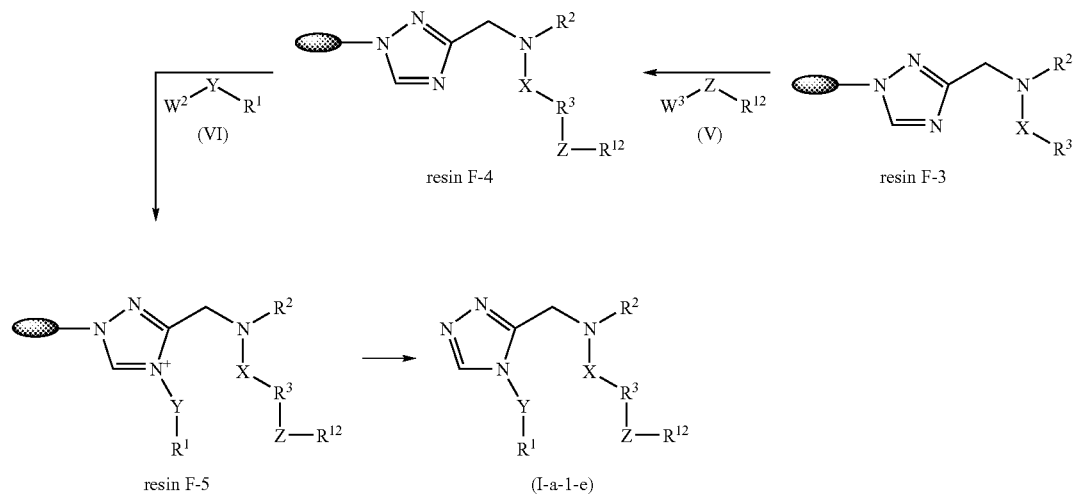

The R³ group in reagent IV above is similar to that described for Scheme A with the stipulation that it must contain a group that can be displaced by a nucleophile. Example groups include a halomethylene (CH₂—Cl or CH₂—Br) or ortho-nitrofluoro phenyl moiety. The descriptions for resin F-3 can therefore be X=CO, SO₂; R³=CH₂Cl, C₆H₄CH₂Cl, C₆H₄CH₂Br, C₆H₄(NO₂)(ortho-F) etc. All steps in above scheme G except step 4, is conducted in a similar manner as described for equivalent intermediates in scheme A. The procedure for step 4 involves reaction with a nucleophile such as a secondary or primary amine additionally substituted with an alkyl, heteroalkyl, aryl, heteroaryl moiety, or a similarly substituted thiol or a hydroxy bearing agent. The nucleophile may also be a heterocycle containing a nucleophilic nitrogen atom such as a substituted imidazole, triazole, indole, benzimidazole etc. The descriptions of groups for resin F-4, F-5 and structure I-a-1-e are therefore R¹² is Alkyl, subst. alkyl, Aryl, heteroaryl, cycloalkyl, cycloaryl, etc. and Z is NH, N, O, S.

Other variations to R² and R³ group modifications are also possible. For example, The R³ group may be a substituted benzimidazole or indole group, when ortho-fluoro or ortho-iodo nitro benzene groups are attached to the nitrogen atom in resin A-2 (Scheme A) employing procedures similar to those described for step 3 in Scheme A. Such ortho-fluoro or ortho-iodo benzene is then further modified to substituted indole or benzimidazole groups employing solid phase synthesis methods well established in art. It is also readily possible to effect similar types of modifications to the R² group as those discussed for R³ group above. In all solid phase synthesis techniques, a method to facilitate rapid parallel synthesis of compound libraries such as some well described in art was employed.

Solution phase synthesis methods employing traditional procedures and schemes well established in art may also be utilized for synthesis of all target compounds described. Such methods were most useful for scale up of intermediates and in synthesis of compounds wherein =Z¹-Z²=Z³- represents a radical of formula (a-1) and L¹ and L² in structure I-a-1-g (Scheme J) are R¹—Y— whereby Y is $C_{1-4}$alkanediyl for L¹, and whereby Y is $C_{1-4}$alkanediyl or a direct bond for L². This synthesis scheme shown below is not limited to only these compounds however and can be readily utilized by one practiced in the art for a diversity of structures otherwise inaccessible by solid phase synthesis. Example procedures for various steps employed in Scheme J can be found in De Lombaert, S. De et al. *J. Med. Chem.* 2000, 43, 488; Owens, A. P. et. al. *Bioorg. Med. Chem. Lett.* 1998, 8, 51; Baldwin, J. J. et al. *J. Med. Chem.* 1975, 18, 895 etc.

General Scheme J

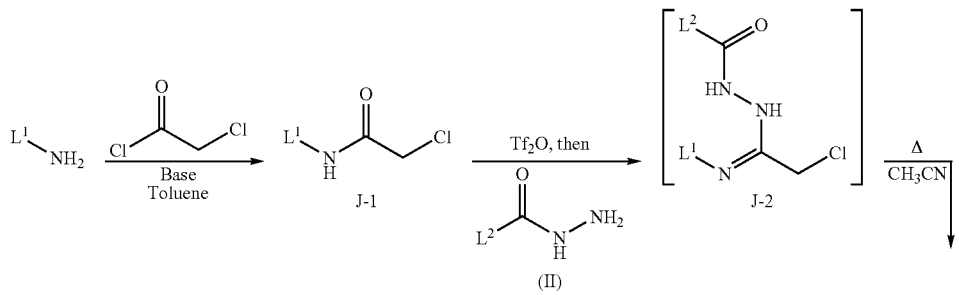

-continued

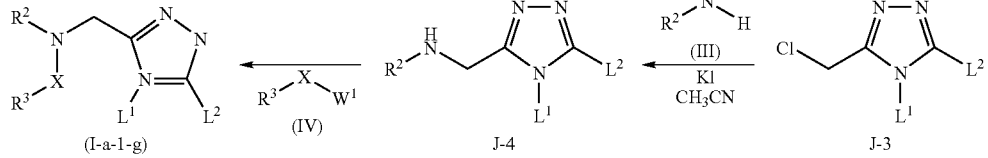

Step 1: The amine which is commercially available or can be made using conventional techniques, is reacted with an (α-haloacyl halide such as for example, chloroacyl chloride or bromoacyl bromide in the presence of a suitable base such as, for example, N,N-diisopropylethylamine and a suitable solvent such as, for example, toluene to give intermediate J-1 after a brief work up.

Step 2: Intermediate J-1 is activated with an activating agent such as for example trifluoromethane sulfonic anhydride or phosphorus pentachloride in a suitable solvent such as, for example, acetonitrile and subsequently treated with an acyl hydrazide of formula II, whereby the $L^2$ group may be an alkyl, substituted alkyl, a substituted or unsubstituted $C_{1-14}$heterocycle, cyano or an aryl moiety.

Step 3: The intermediate J-2 was heated without isolation resulting in intermediate J-3, which was isolated after a work up and chromatography conform to those well described in art.

Step 4: Reaction with an amine of formula III (as described in Scheme A) in the absence or presence of a suitable activating agent such as, for example, potassium iodide in a suitable solvent such as, for example, acetonitrile produced intermediate J-4 after work up and isolation.

Step 5: This step was carried out in the same manner as described for step 3 in Scheme A, except that work up and isolation procedures conformed to those well described in art for solution phase synthesis with or without the aid of scavenger resins and thereafter, or simultaneously therewith, effecting one or more of the following optional conversions:

(i) when the compound of formula (I) is formed, converting it into another compound of formula (I) having different values of $L^1$, $L^2$, $R^2$, $R^3$, and $R^4$ by treatment with an appropriate reagent and/or under suitable conditions;

(ii) removing any remaining protecting groups;

(iii) when the compound of formula (I) is formed, converting into a prodrug, N-oxide, addition salt, quaternary amine or stereochemically isomeric form thereof;

(iv) when a pharmaceutically acceptable derivative of a compound of formula (I) is formed, converting the said derivative into a compound of formula (I), or a different derivative thereof.

Example A7 further exemplify this synthesis route.

Variations to the above mentioned schemes A, B, C, D and E are possible. For instance, it may be convenient to build the chemical groups defined in $R^2$ and $R^3$ in different steps. Steps 3a and 3b in example A5 exemplify this synthesis route.

Another example of such variation is exemplified in example A6. There, the cleavage from the resin is performed prior to reacting the thus formed monosubstituted triazole derivative with an intermediate of formula (IV).

Said monosubstituted triazoles, generally depicted as follows

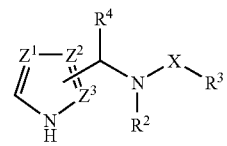

are interesting and useful intermediates in the preparation of the compounds of formula (I). Some of said monosubstituted triazoles also show interesting farnesyl transferase inhibiting activity.

The intermediates used in the above synthesis schemes are either commercially available or can be prepared according to generally known synthesis procedures.

The compounds of formula (I) containing a stereogenic center as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Compounds of formula (I) may be converted into an ester by reaction with an appropriate esterifying agent, for example, an acid halide or anhydride. Where it is desired to isolate a compound of formula (I) as an acid addition salt, for example, a physiologically acceptable acid addition salt, the salt may be formed by reacting the compound of formula (I) in the form of the free base with the appropriate acid. The two reactants are preferably used in equivalent amounts and the reaction may be carried out in a suitable solvent such as an alcohol, for example ethanol, an ester, for example ethyl acetate, or an ether, for example tetrahydrofuran. One salt of a compound of formula (I) may be converted into another salt using standard methods, for example where it is desired to convert a salt of a compound of formula (I) with an acid which is not physiologically acceptable into a salt with a physiologically acceptable acid. An ester or salt may be converted into the parent compound, for example by hydrolysis.

The compounds of formula (I), the pharmaceutically acceptable acid addition salts and stereoisomeric forms thereof have valuable pharmacological properties in that they surprisingly have valuable farnesyl protein transferase (FPTase) and/or geranylgeranyltransferase inhibitory effects.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, *Cancer Research*, 55, 4575-4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma, kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neurofibromatosis, or tumors in which ras is activated due to mutation or overexpression of tyrosine kinase oncogenes, may be inhibited by the compounds of this invention.

The compounds of present invention are particularly useful for the treatment of proliferative diseases, both benign and malignant, wherein the K-ras B isoform is activated as a result of oncogenic mutation.

Hence, the present invention discloses the compounds of formula (I) for use as a medicine as well as the use of these compounds of formula (I) for the manufacture of a medicament for treating one or more of the above mentioned conditions.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 1 mg to 200 mg of active ingredient per unit dosage form.

The present invention also relates to a combination of an antineoplastic agent and a compound of the present invention, i.e. a farnesyl transferase inhibitor, and thus relates also to a method of treating cancer using said combination, which method comprises administering to a mammal, either sequentially in any order or simultaneously, therapeutic effective amounts of at least one antineoplastic agent and one compound of the present invention. The present invention thus also relates to a combination of an antineoplastic agent and a compound of the present invention for use as a medicine.

Examples of an antineoplastic agent include, for instance, microtubule-stabilising agents such as paclitaxel, docetaxel, epothilone A, epothilone B, desoxyepothilone A, desoxyepothilone B or derivatives thereof; microtubule-disruptor agents; alkylating agents; anti-metabolites; a fusel poison; epidophyllotoxin; an antineoplastic enzyme; a topoisomerase inhibitor; procarbazine; mitoxantrone; platinum coordination complexes; biological response modifiers and growth inhibitors; hormonal and anti-hormonal therapeutic agents and hematopoietic growth factors.

Example classes of antineopastic agents include, for instance, the anthracycline family of drugs, vinca drugs, mitomycins, bleomycins, cytotoxic nucleosides, taxanes, epothilones, discodermolide, the pteridine family of drugs, diynenes and the podophyllotoxins.

Examples of particularly useful antineoplastic agents include doxorubicin, carminomycin, daunorubicin, aminopterin, methotrexate, metopterin, dichloro-methotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, paclitaxel, estramustine, cisplatine, carboplatin, cyclophosphamide, bleomycin, tamoxifen, ifosamide, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

Said combination may also be used in conjunction with other methods of treating cancers and/or tumors, including radiation therapy and surgery. Radiation therapy, including X-rays or gamma-rays which are delivered from either an externally applied beam or by implantation of radioactive sources, may also be used in combination with a compound of the present invention alone to treat cancer. The compound of formula (I) may be administered concurrently with the radiation therapy or may be administered prior to the application of the radiation.

According to a further aspect of this invention the compounds of formula (I) or any subgroup thereof show antiviral properties. Viral infections treatable using the compounds and methods of the present invention include those infections brought on by ortho- and paramyxoviruses and in particular by human and bovine respiratory syncytial virus (RSV).

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The following examples are provided for purposes of illustration.

A Preparation of the Compounds of Formula (I) Following Scheme A

Hereinafter, the following acronyms are used: DMF [N,N-dimethylformamide], DCE [1,2-dichloroethane], DCM [dichloromethane], DIEA [N-ethyl-N-(1-methylethyl)-2-propanamine]

EXAMPLE A1

Preparation of

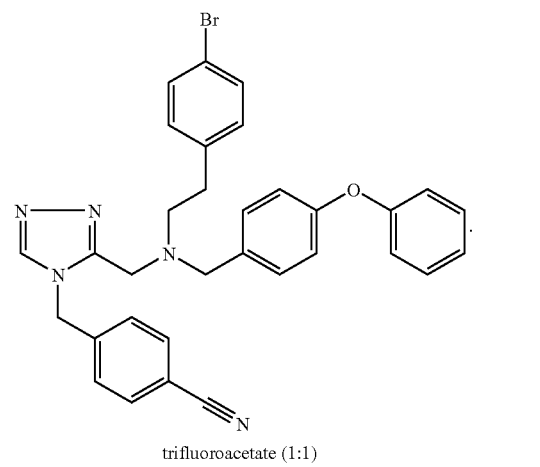

(compound 3)

trifluoroacetate (1:1)

Step 1:

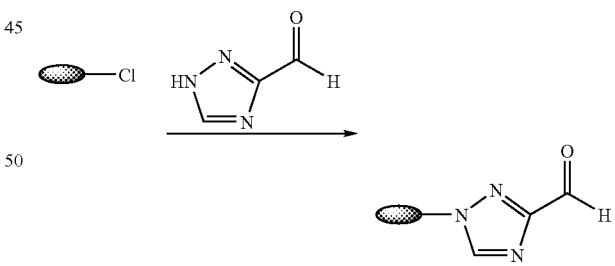

DMF (45.0 mL) and DIEA (15.0 mL, 0.0861 mole) were added to a hot solution of 1H-1,2,4-triazole-3-carboxaldehyde (2.71 g, 0.0279 mole). The mixture was heated while shaking until homogeneous. The warm solution was diluted with DCE (15.0 mL), and the solution was added to the pre-swelled 2-chlorotrityl chloride resin (10.00 g, 0.010 mole). The solution was heated at 60° C. overnight with intermittent $N_2$ bubbling. The resulting resin was drained, then heated in DMF (45 mL) at 60° C. for 30 min. The warm DMF washing was repeated four times. The resin was rinsed with DCM (4×) and methanol (4×) and dried in vacuo overnight.

Step 2:

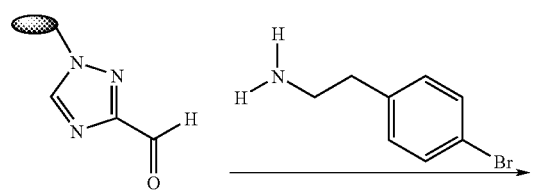

A solution of the 4-bromo-benzeneethanamine (0.025 mole) in 1,2-dichloroethane (99.0 mL) and acetic acid (1.00 mL) was added to the pre-swelled resin from step 1 (0.005 mole). The mixture was sonicated for 5 min at 23° C. then heated to 60° C. for 30 min with intermittent $N_2$ bubbling. Na(AcO)$_3$BH (5.299 g, 0.025 mole) was added. The mixture was sonicated for 5 min at 23° C. then heated to 60° C. for 30 min with intermittent $N_2$ bubbling. The heat source was removed, and the reaction was allowed to bubble overnight at 23° C. Excess Na(AcO)$_3$BH was quenched with methanol. The resin was rinsed with DMF (4×) and methanol (4×), then dried in vacuo overnight.

Step 3:

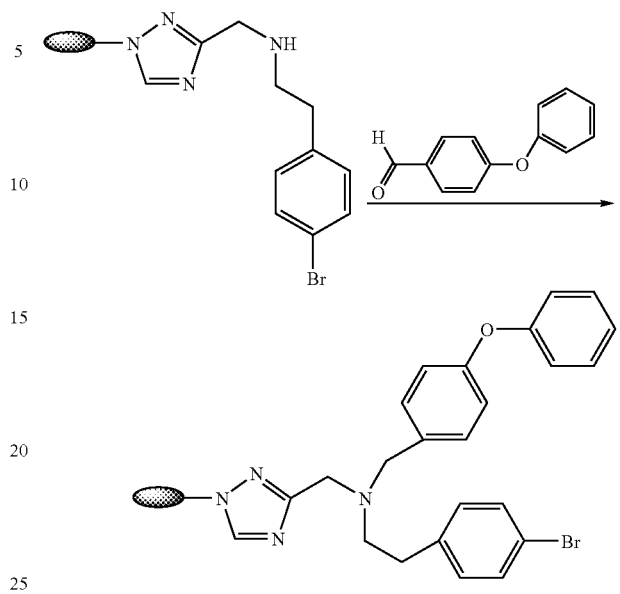

The resin from step 2 (0.00113 mole) was weighed into a custom 200 mL solid phase synthesis bottle and the 4-phenoxybenzaldehyde (0.00565 mole) was added in a solution of 1% acetic acid-DCE (28.6 mL). The mixture was purged with $N_2$ and sonicated in a warm (60° C.) ultrasonic bath for 10 min. The mixture was then allowed to gently agitate under $N_2$ for 16 hour. A pre-sonicated solution of NaBH(OAc)3 (0.00565 mole) was then added and reaction vessel sonicated for 10 min at 60° C. and then allowed to gently agitate under $N_2$ overnight. The resulting resin was then washed with methanol (2×), DMF (6×), methanol (4×), and DCM (6×).

Step 4:

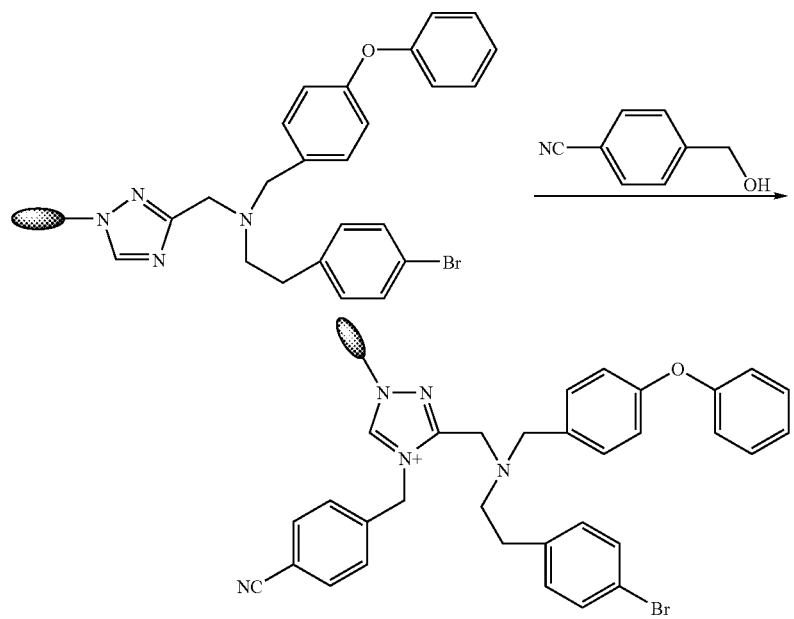

A solution of the 4-(hydroxymethyl)-benzonitrile (0.00019 mole) and DIEA (0.00019 mole) in DCM (1 mL) was added to the resin from step 3 (0.000093 mole). A solution of trifluoroacetic acid anhydride in DCM (1 mL) was added to the mixture at −78° C. The reaction was agitated under N₂ for 30 min at −78° C., then at room temperature for 4 hr. The solution was removed through filtration. The reaction was repeated on the resin. The solutions were combined, dried under N₂, and purified by HPLC.

Step 5:

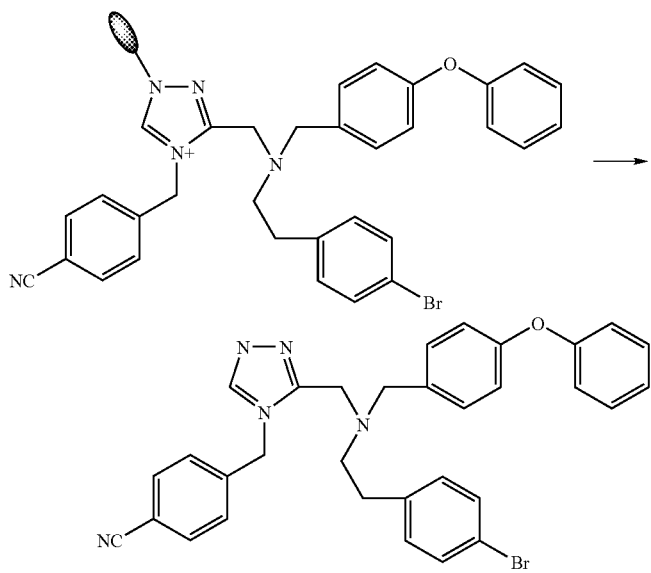

95:5 Trifluoroacetic acid: DCM (5 mL) was added to the dried resin from step 4 (0.0001 mole). The resin was allowed to sit in the cleavage solution for 2 hr. The resin was filtered off, and the solvent was removed from the resulting solution using a Savant speedvac. The resulting residue was combined with the solution obtained from step 4 and purified by reverse phase HPLC utilizing a gradient of acetonitrile with 0.1% trifluoroacetic acid to water with 0.1% trifluoroacetic acid. The pure fractions from HPLC were combined, frozen, and lyophilized overnight.

EXAMPLE A2

Preparation of (compound 4)

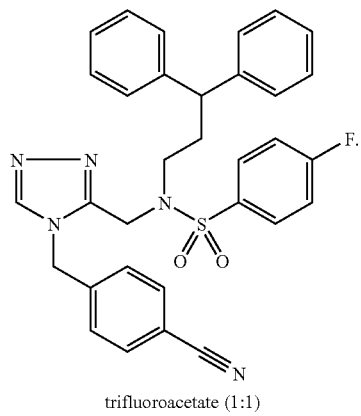

trifluoroacetate (1:1)

Step 1 & 2: Analogous to Step 1 & 2 of Example A1

Step 3:

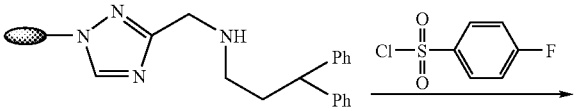

-continued

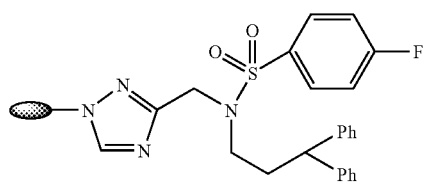

The resin from step 2 (0.000075 mole) was swelled in DCM (10 mL) and then drained. A solution of DIEA (0.87 mL, 0.0025 mole) in 1 M DCE was added, followed by a solution of the sulfonyl chloride (0.0025 mole) in 0.5 M DCE. The resulting suspension was shaken with gyrating motion under intermittent N₂ purge for 12 hours. The solvent was then removed, and the resin was washed 6 times with DCM, twice DMF, 4 times with DCM, and finally 6 times with methanol. The resulting resin was then dried in vacuum.

Step 4 & 5: Analogous to step 4 & 5 of example A1.

EXAMPLE A3

Preparation of (compound 141)

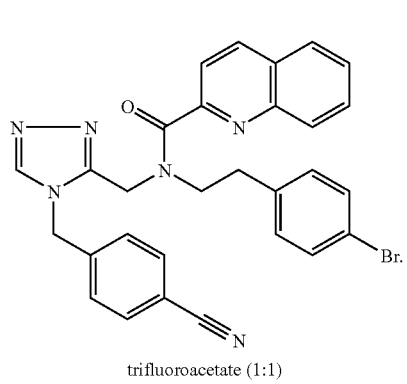

trifluoroacetate (1:1)

Step 1 & 2: Analogous to Step 1 & 2 of Example A1
Step3:

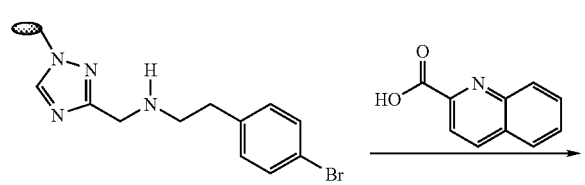

A solution of the 2-quinolinecarboxylic acid (0.00025 mole), 1-[bis(dimethylamino)methylene]-hexafluorophosphate(1−)-1H-benzotriazolium 3-oxide (0.00025 mole) and DIEA (0.0005 mole) in DMF (2 mL) was added to the resin from step 2 (0.000091 mole). The reaction mixture was agitated under N$_2$ overnight at room temperature. The solvent was drained and the resulting resin was washed extensively with DMF, methanol, and DCM. The resulting resin was dried under N$_2$.

Step 4 & 5: Analogous to Step 4 & 5 of Example A1.

EXAMPLE A4

Preparation of (compound 164)

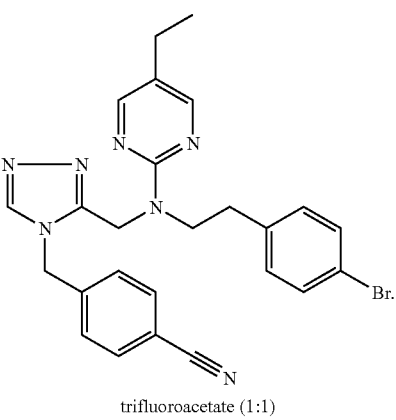

trifluoroacetate (1:1)

Step 1 & 2: Analogous to Step 1 & 2 of Example A1
Step 3:

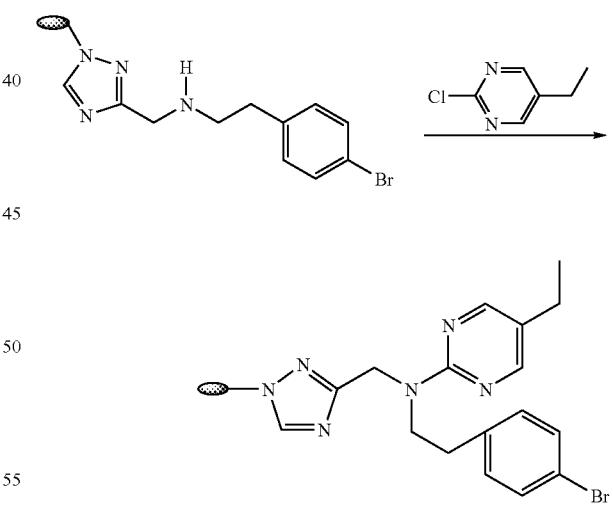

A solution of 2-chloro-5-ethyl-pyrimidine (0.00157 mole) in dioxane and DIEA (0.00189 mole) were added to the resin from step 2 (0.00105 mole). The reaction mixture was heated at 85° C. for 2 days. The resulting resin was washed with DMF, methanol, and DCM, then dried under N$_2$.

Step 4 & 5: Analogous to Step 4 & 5 of Example A1

EXAMPLE A5

Preparation of (compound 192)

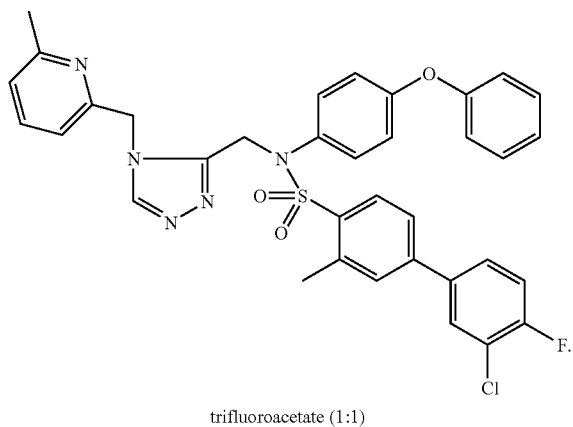

trifluoroacetate (1:1)

Step 1 & 2: Analogous to Step 1 & 2 of Example A1
Step 3a:

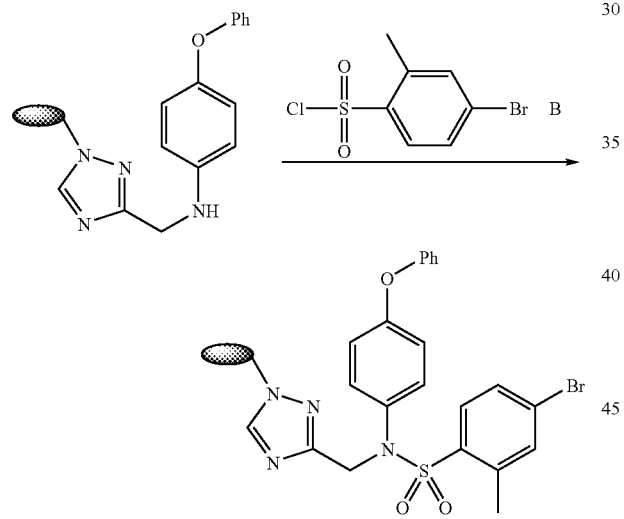

This step was accomplished analogous to step 3 in example A2.

Step 3b:

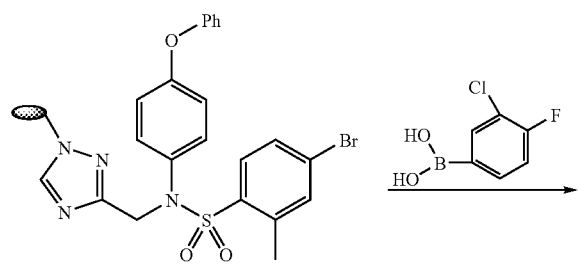

-continued

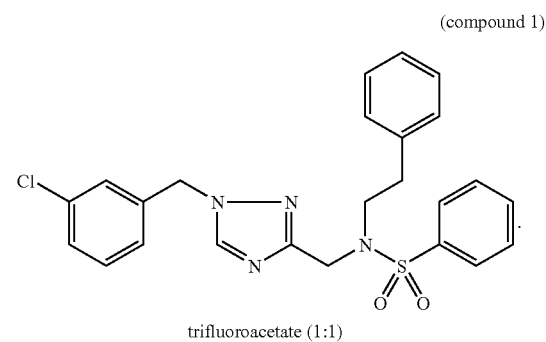

Dimethyl ether (1.6 mL) was added to the resin from step 3a (0.0001 mole). The resulting suspension was degassed by bubbling Ar for several minutes. $Pd[P(C_6H_5)_3]_4$ (0.0004 mole) was added, and the mixture was agitated for 5 minutes. The (3-chloro-4-fluorophenyl)-boronic acid (0.0004 mole) and sodium carbonate (0.0005 mole) were added. The mixture was then refluxed for 14 hours under gentle Ar purging. The mixture was cooled to room temperature, diluted with 25% ammonium acetate, and stirred for 5 minutes and drained. The resulting resin was successively washed with 2 mL each of 1:1 dimethyl ether: $H_2O$, 0.2N HCl, $H_2O$, dimethyl ether, DCM, and methanol. The resin was dried in a high vacuum.

Step 4 & 5: Analogous to Step 4 & 5 of Example A1.

EXAMPLE A6

Preparation of (compound 1)

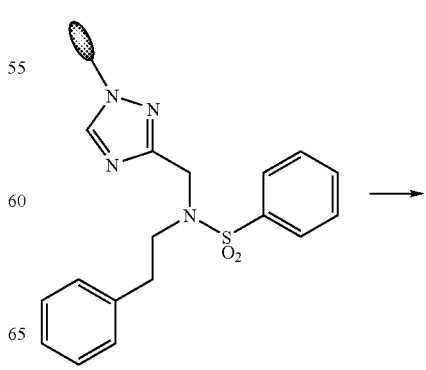

trifluoroacetate (1:1)

Step 1 & 2: Analogous to Step 1 & 2 of Example A1
Step 3: Analogous to Step 3 of Example A2.
Step 4:

-continued

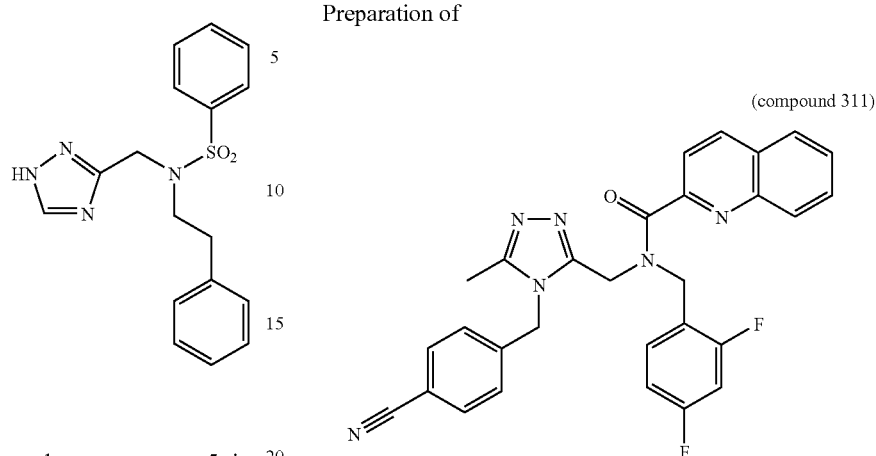

The cleavage was performed analogous to step 5 in example A1.

Step 5:

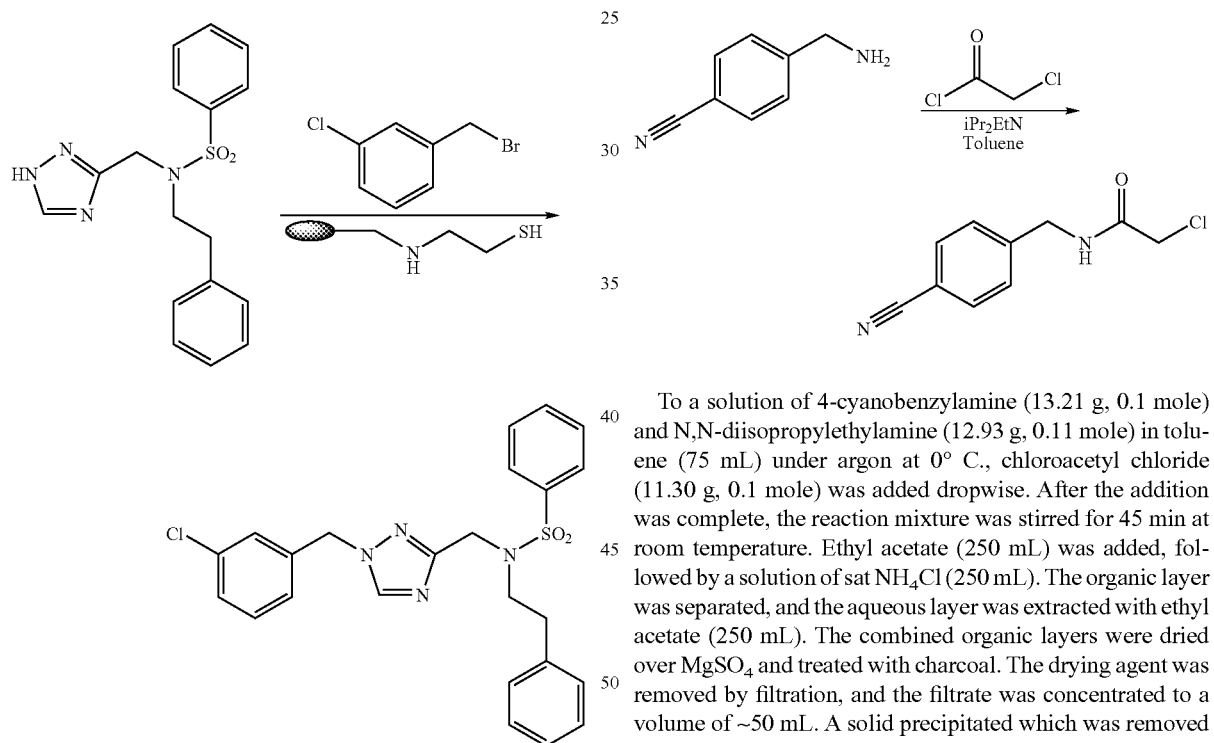

Sodium hydride (0.00069 mole) was added to a solution of the triazole resulting from step 4 in dimethylsulfoxide (2 mL). After 10 minutes 25° C., 1-(bromomethyl)-4-chloro-benzene (0.00104 mole) was added, and the resulting solution was left overnight at 25° C. The pre-swelled scavenger resin to remove excess, 1-(bromomethyl)-4-chloro-benzene was added. The resin was filtered off, and the resulting rinses were combined with the reaction solution. The dimethylsulfoxide solution was diluted tenfold with water, and passed through a solid phase extraction column, then rinsed with water. The compound 1 was eluted with acetonitrile, purified by preparatory HPLC, frozen, and lyophilized.

EXAMPLE A7

Preparation of (compound 311)

Step 1:

To a solution of 4-cyanobenzylamine (13.21 g, 0.1 mole) and N,N-diisopropylethylamine (12.93 g, 0.11 mole) in toluene (75 mL) under argon at 0° C., chloroacetyl chloride (11.30 g, 0.1 mole) was added dropwise. After the addition was complete, the reaction mixture was stirred for 45 min at room temperature. Ethyl acetate (250 mL) was added, followed by a solution of sat NH$_4$Cl (250 mL). The organic layer was separated, and the aqueous layer was extracted with ethyl acetate (250 mL). The combined organic layers were dried over MgSO$_4$ and treated with charcoal. The drying agent was removed by filtration, and the filtrate was concentrated to a volume of ~50 mL. A solid precipitated which was removed by filtration. The solid was dried under vacuum to yield 14.25 g (68.3%) of 4-cyanobenzyl-5-methyl-1,2,4-triazole.

Step 2:

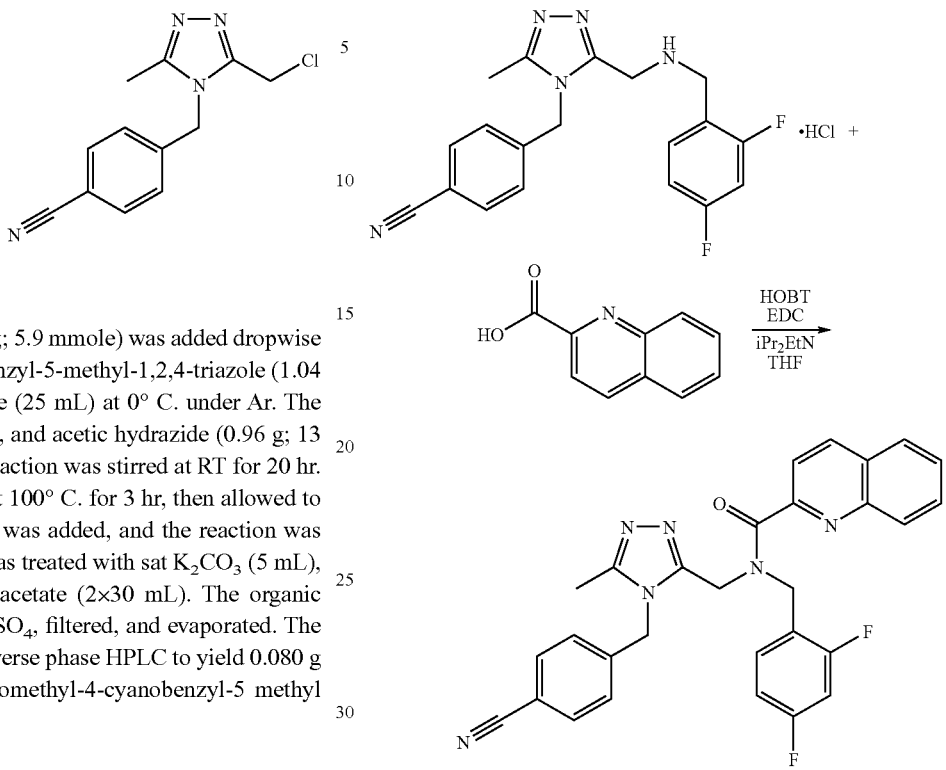

Triflic anhydride (1.66 g; 5.9 mmole) was added dropwise to a solution of 4-cyanobenzyl-5-methyl-1,2,4-triazole (1.04 g; 5 mmole) in acetonitrile (25 mL) at 0° C. under Ar. The cooling bath was removed, and acetic hydrazide (0.96 g; 13 mmole) was added. The reaction was stirred at RT for 20 hr. The reaction was heated at 100° C. for 3 hr, then allowed to cool to RT. Water (5 mL) was added, and the reaction was evaporated. The residue was treated with sat $K_2CO_3$ (5 mL), and extracted with ethyl acetate (2×30 mL). The organic phase was dried over $Na_2SO_4$, filtered, and evaporated. The residue was purified by reverse phase HPLC to yield 0.080 g (6.5%) of desired 3-chloromethyl-4-cyanobenzyl-5 methyl triazole.

Step 3:

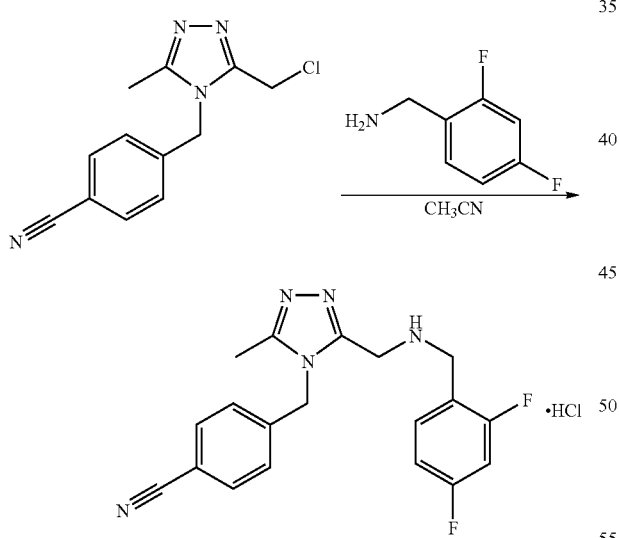

3-Chloromethyl-4-cyanobenzyl-5 methyl triazole (0.080 g; 0.32 mmole ) and 2,4-difluorobenzylamine (0.254 g; 1.77 mmole) were combined in acetonitrile (10 mL), and stirred under argon for 7 days at room temperature. The formed solid was removed by filtration, and the filtrate was concentrated to dryness at 35° C. under a nitrogen flow. After reverse phase HPLC purification, the compound was readsorbed onto the column and eluted with a dilute HCl solution and lyophilized to yield 0.033 g (26.2%) of desired secondary amine.

Step 4:

Secondary amine (33 mg; 0.085 mmole), quinaldic acid (19 mg; 0.11 mmole), 1-hydroxybenzotriazole (HOBt; 18 mg; 0.13 mmole), 1-(3-dimethylaminopropyl)-3-ethylcarbodiimide hydrochloride (EDC; 25 mg; 0.13 mmole), and N,N-diisopropylethylamine (32 mg; 0.25 mmole) were combined in anhydrous tetrahydrofuran (10 mL). The reaction was stirred at room temperature for 20 hr. The solvent was removed under a nitrogen flow, and the residue was purified by reverse phase HPLC to yield 20 mg (46.5%) desired triazole.

EXAMPLE A8

Preparation of (compound 67)

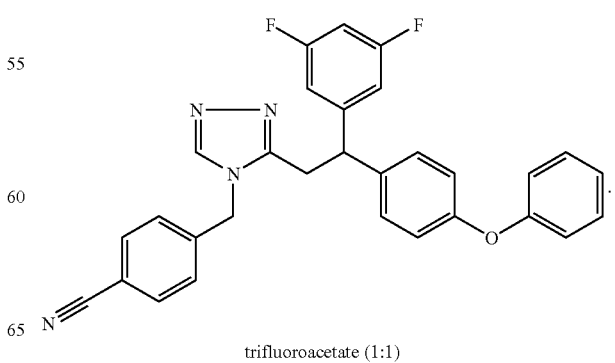

trifluoroacetate (1:1)

51

Step 1 & 2: Analogous to step 1 & 2 of example A1
Step 3:

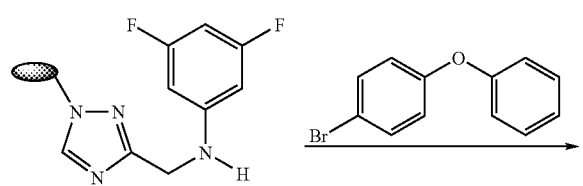

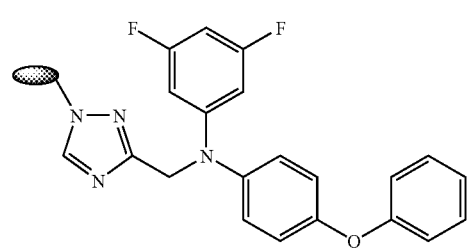

A solution of 4-Bromodiphenyl ether (0.0015 mole) in dioxane (1 mL) was added to the resin from step 2 (0.0001 mole) under nitrogen. A solution of $Pd_2dba_3$ (0.00002 mole), BINAP (0.00004 mole) and sodium tert-butoxide (0.0018 mole) in dioxane (2 mL) was added to the suspension resin. The reaction mixture was agitated under $N_2$ overnight at 80° C. The solvent was drained and the resulting resin was washed with $H_2O$, DMF, DCM, methanol and DCM. The resulting resin was dried under $N_2$.

Step 4 & 5: Analogous to Step 4 & 5 of Example A1

EXAMPLE A9

Preparation of (compound 221)

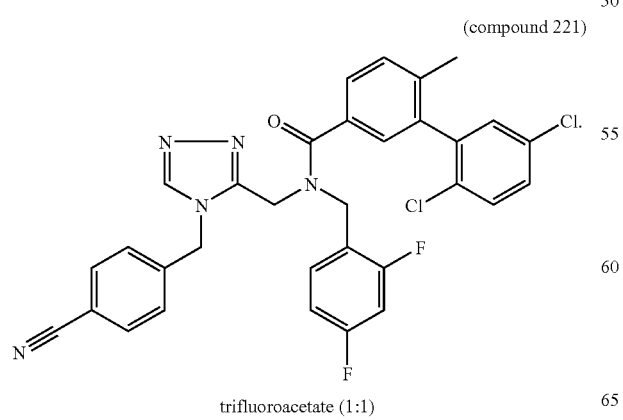

trifluoroacetate (1:1)

52

Step 1 & 2: Analogous to Step 1 & 2 of Example A1
Step 3a:

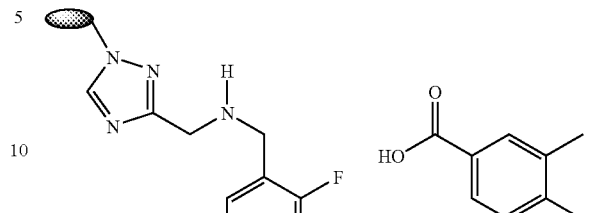

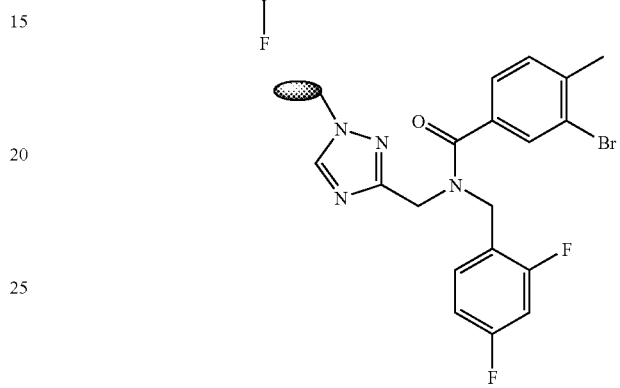

This step was accomplished analogous to step 3 in example A3 Step 3b:

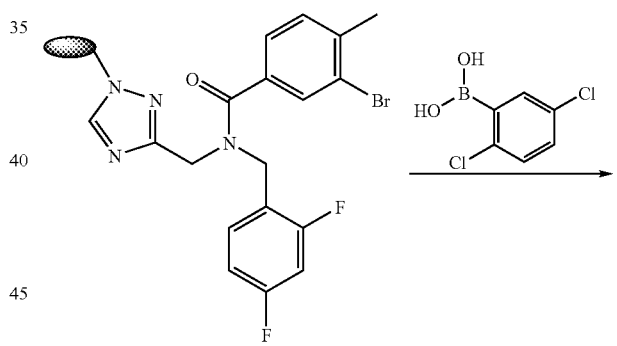

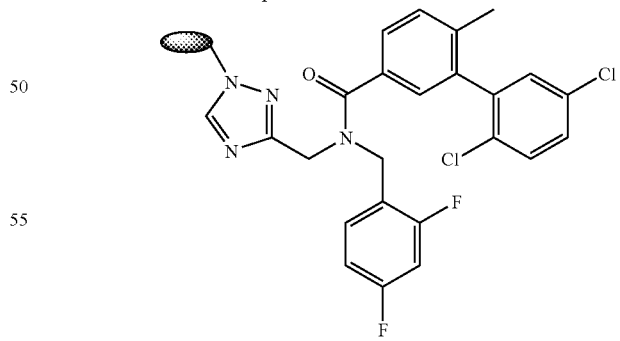

This step was accomplished analogous to step 3b in example A5

Step 4 & 5: Analogous to Step 4 & 5 of Example A1

The following compounds were prepared analogous to example A1: 3, 7 to 13, 23 to 64, 88 to 140, 150 to 158, 168 to 177, 179 to 185 & 217.

The following compounds were prepared analogous to example A2: 4 to 6 & 14 to 22

The following compounds were prepared analogous to example A3: 141 to 149, 218 to 220, 222, 223, 225, 226, 229, 231 to 233, 236, 237, 240, 241, 243 to 254, 256, 258, 262 to 271, 273, 275 to 277, 280, 282, 284 to 286, 289 to 291, 293 to 295, 297 to 307, 310, 314 & 315.

The following compounds were prepared analogous to example A4: 159 to 167 & 178.

The following compounds were prepared analogous to example A5: 186 to 216.

The following compounds were prepared analogous to example A6: 1 & 2.

The following compounds were prepared analogous to example A7: 311 to 313

The following compounds were prepared analogous to example A8: 65 to 87

The following compounds were prepared analogous to example A9: 221, 224, 227, 230, 235, 239, 242, 259, 260, 272, 274, 278, 281, 238, 287, 288, 292, 296 & 308.

All of the above exemplified are depicted herein below.

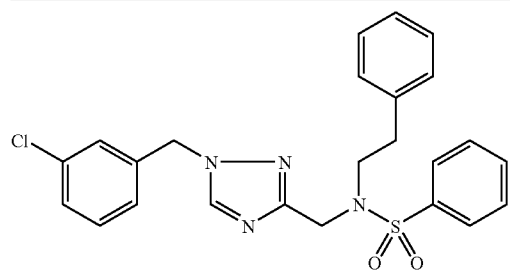

Trifluoroacetate (1:1) comp. 1.

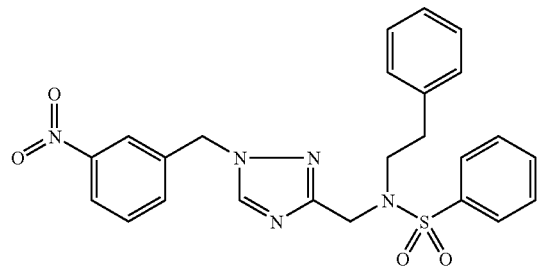

Trifluoroacetate (1:1) comp. 2.

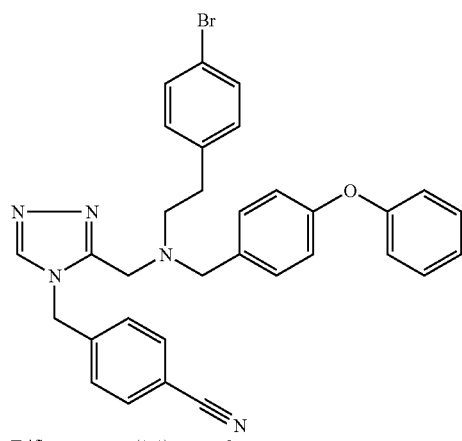

Trifluoroacetate (1:1) comp. 3.

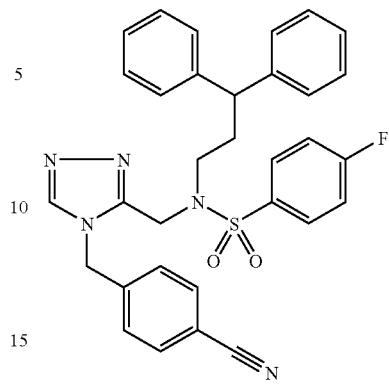

Trifluoroacetate (1:1) comp. 4.

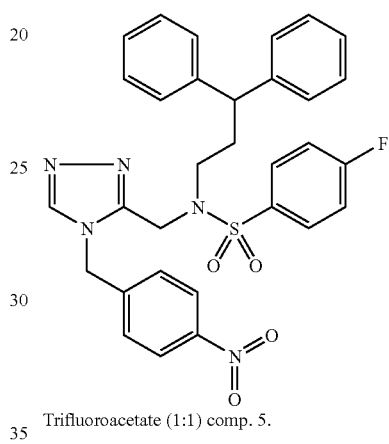

Trifluoroacetate (1:1) comp. 5.

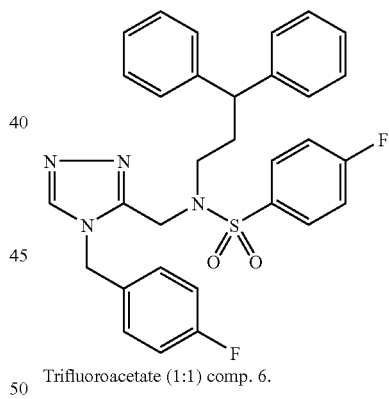

Trifluoroacetate (1:1) comp. 6.

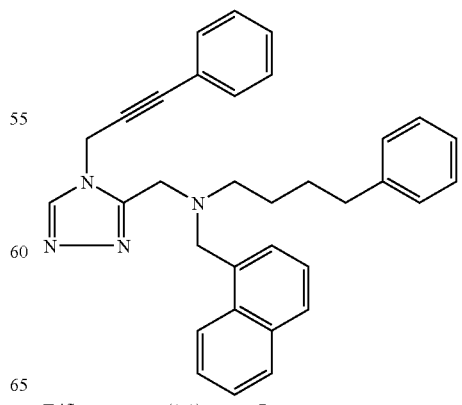

Trifluoroacetate (1:1) comp. 7.

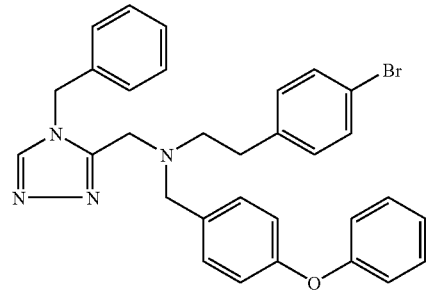
Trifluoroacetate (1:1) comp. 8.
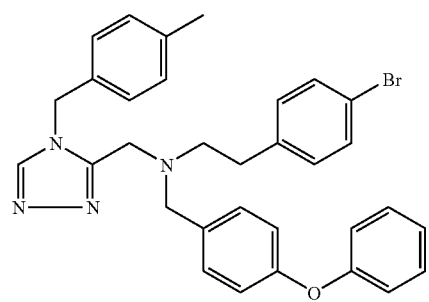
Trifluoroacetate (1:1) comp. 9.
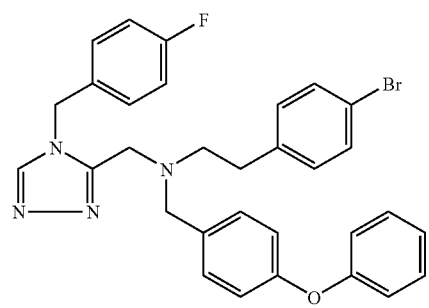
Trifluoroacetate (1:1) comp. 10.
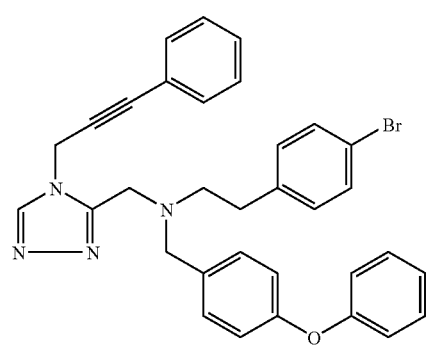
Trifluoroacetate (1:1) comp. 11.
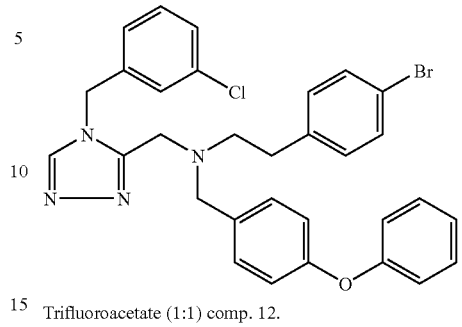
Trifluoroacetate (1:1) comp. 12.
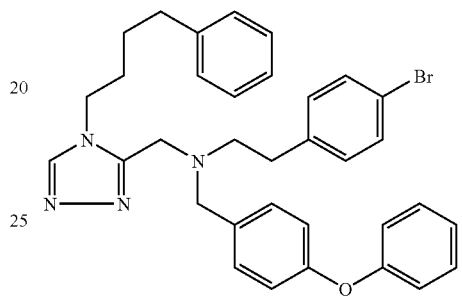
Trifluoroacetate (1:1) comp. 13.
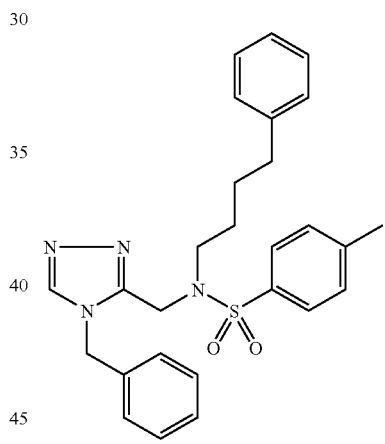
Trifluoroacetate (1:1) comp. 14.
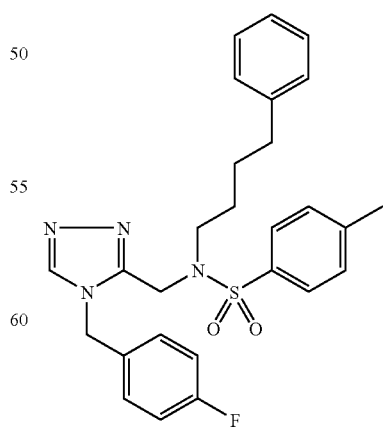
Trifluoroacetate (1:1) comp. 15.

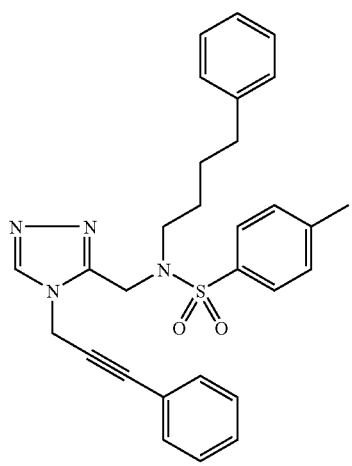
Trifluoroacetate (1:1) comp. 16.
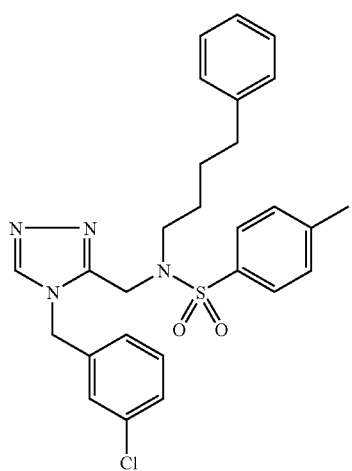
Trifluoroacetate (1:1) comp. 17.
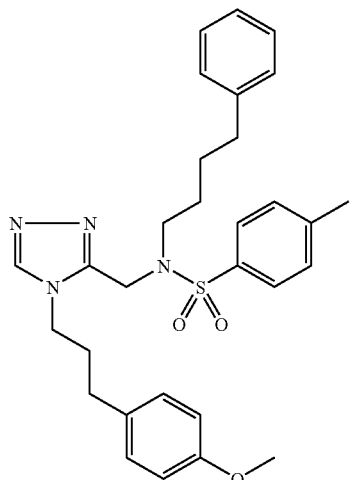
Trifluoroacetate (1:1) comp. 18.
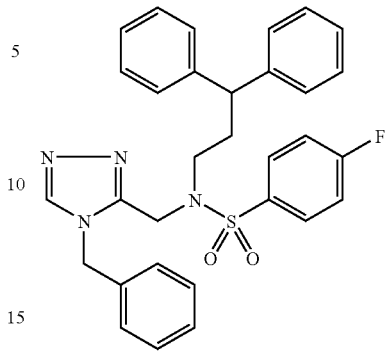
Trifluoroacetate (1:1) comp. 19.
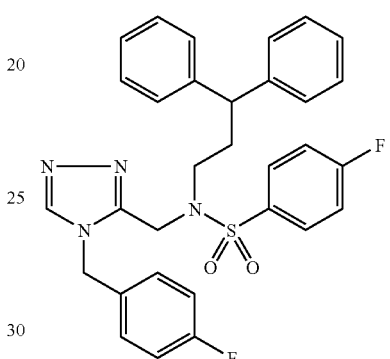
Trifluoroacetate (1:1) comp. 20.
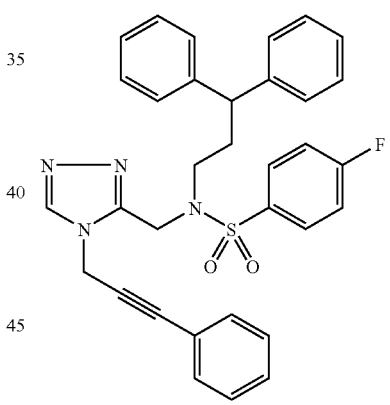
Trifluoroacetate (1:1) comp. 21.
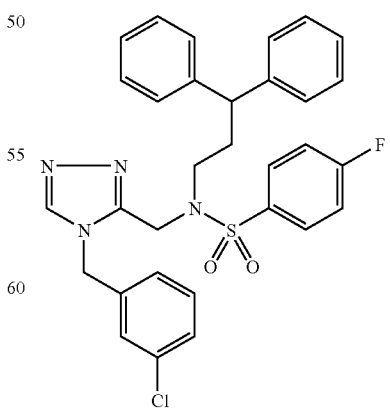
Trifluoroacetate (1:1) comp. 22.

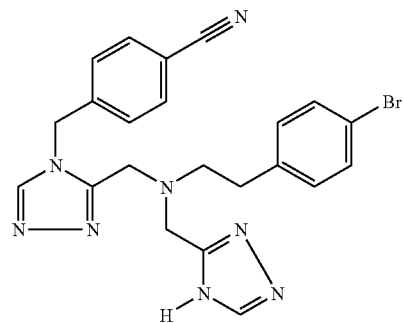
Trifluoroacetate (1:1) comp. 23.
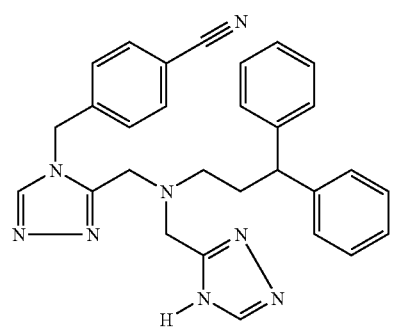
Trifluoroacetate (1:1) comp. 24.
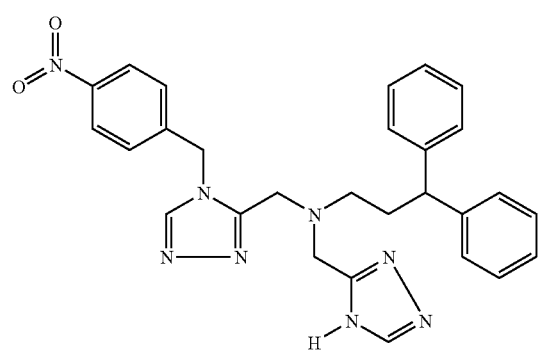
Trifluoroacetate (1:1) comp. 25.
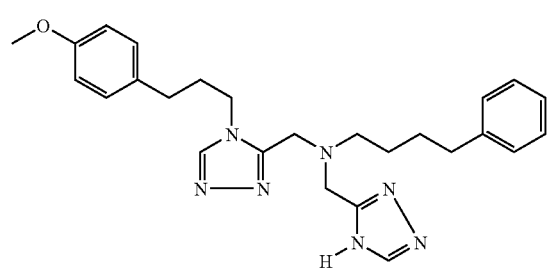
Trifluoroacetate (1:1) comp. 26.
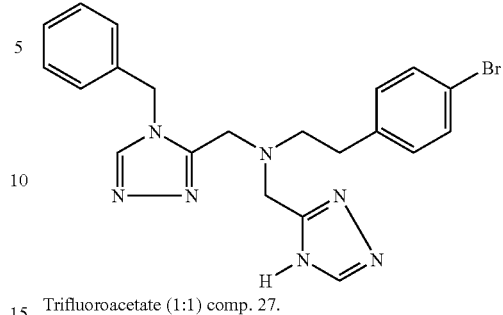
Trifluoroacetate (1:1) comp. 27.
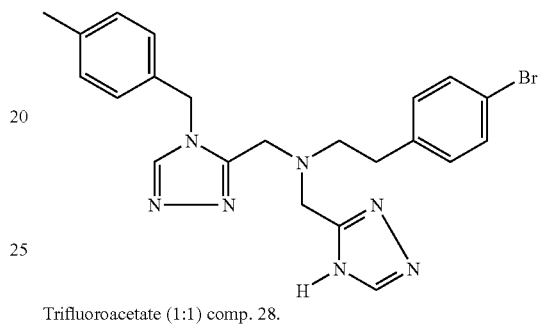
Trifluoroacetate (1:1) comp. 28.
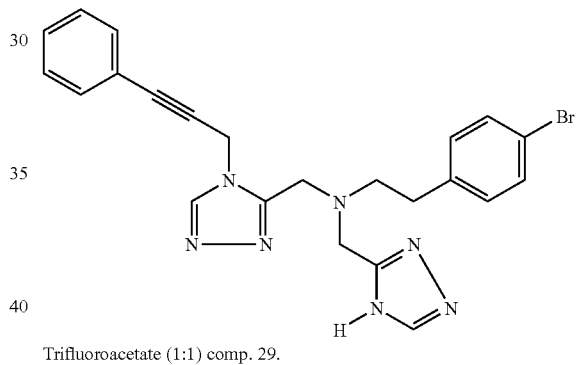
Trifluoroacetate (1:1) comp. 29.
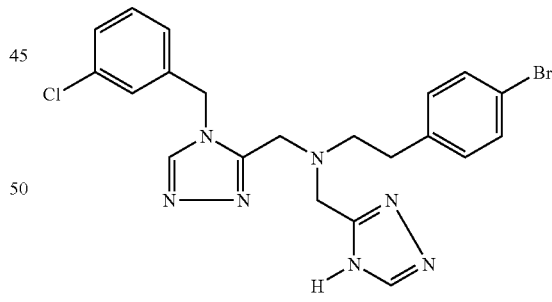
Trifluoroacetate (1:1) comp. 30.
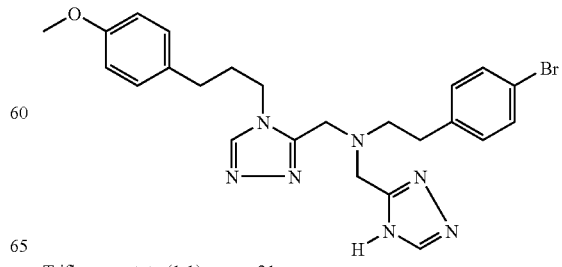
Trifluoroacetate (1:1) comp. 31.

-continued
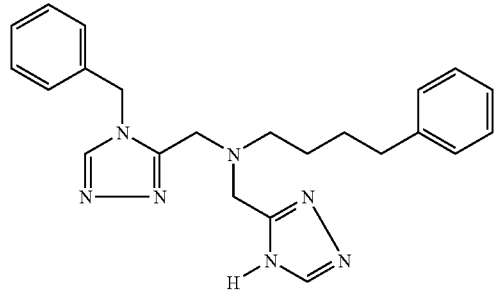
Trifluoroacetate (1:1) comp. 32.
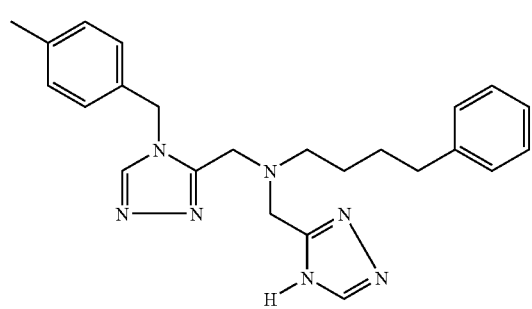
Trifluoroacetate (1:1) comp. 33.
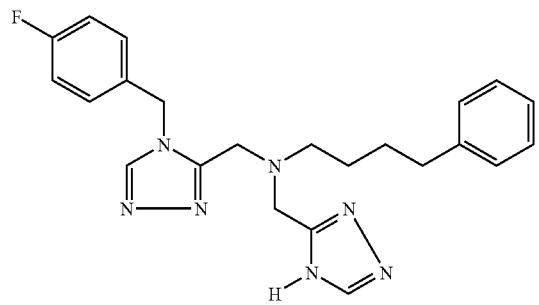
Trifluoroacetate (1:1) comp. 34.
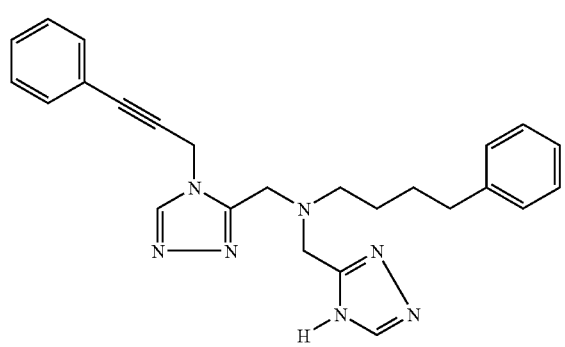
Trifluoroacetate (1:1) comp. 35.
-continued
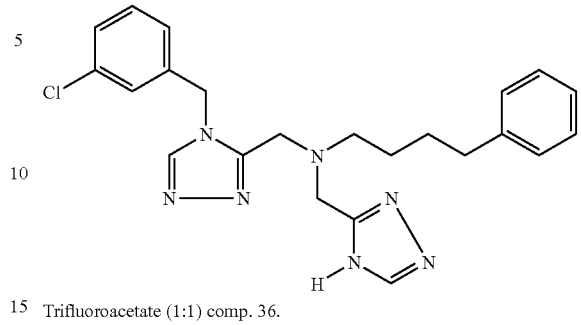
Trifluoroacetate (1:1) comp. 36.
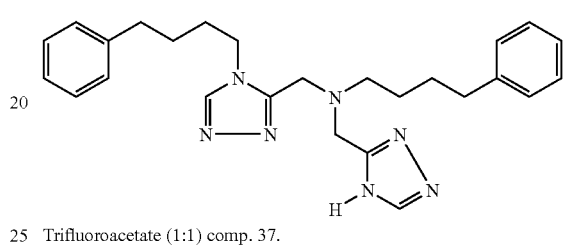
Trifluoroacetate (1:1) comp. 37.
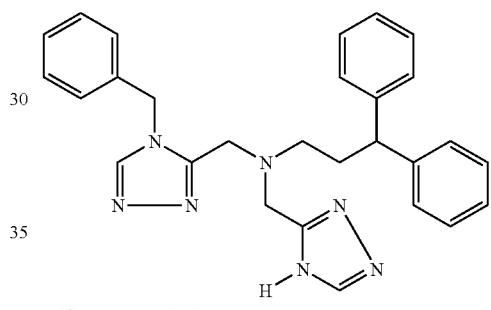
Trifluoroacetate (1:1) comp. 38.
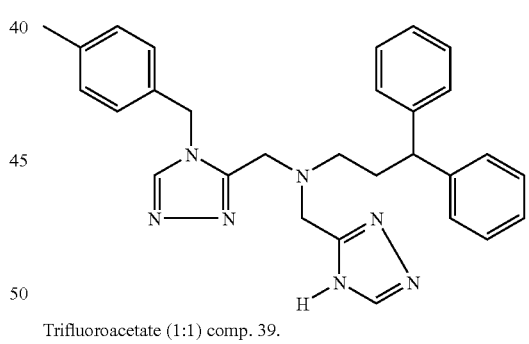
Trifluoroacetate (1:1) comp. 39.
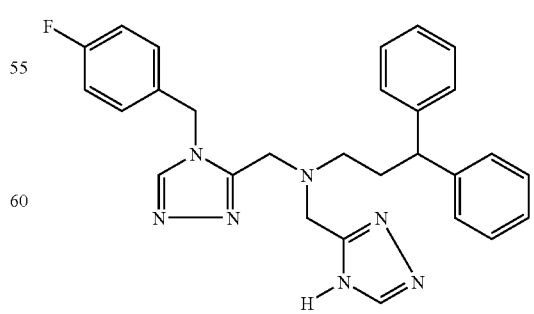
Trifluoroacetate (1:1) comp. 40.

-continued
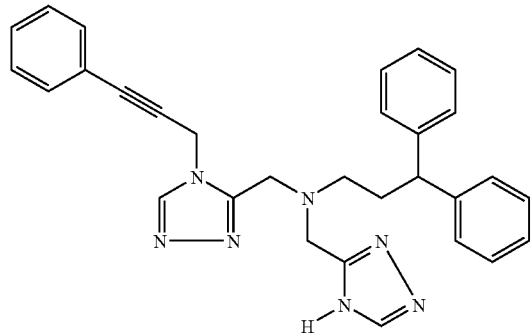
Trifluoroacetate (1:1) comp. 41.
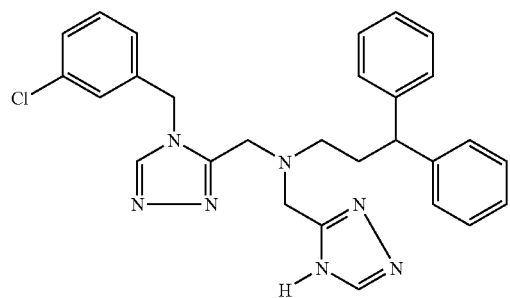
Trifluoroacetate (1:1) comp. 42.
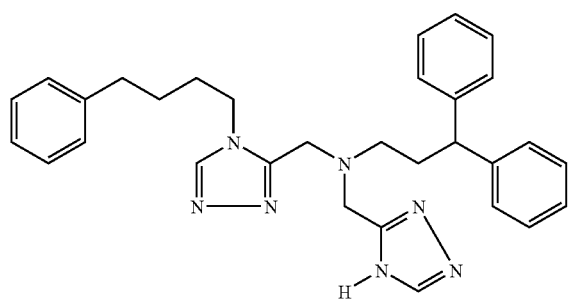
Trifluoroacetate (1:1) comp. 43.
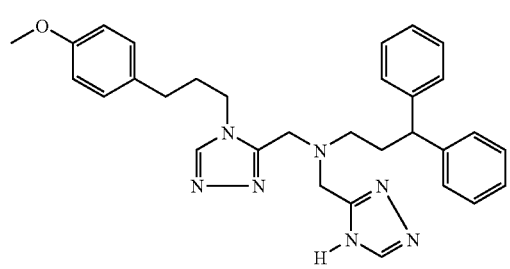
Trifluoroacetate (1:1) comp. 44.
-continued
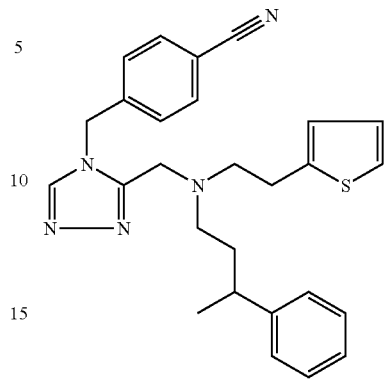
Trifluoroacetate (1:1) comp. 45.
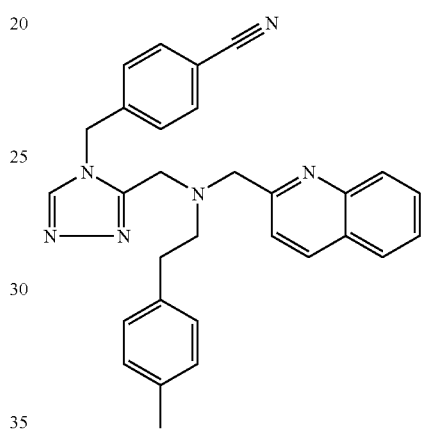
Trifluoroacetate (1:1) comp. 46.
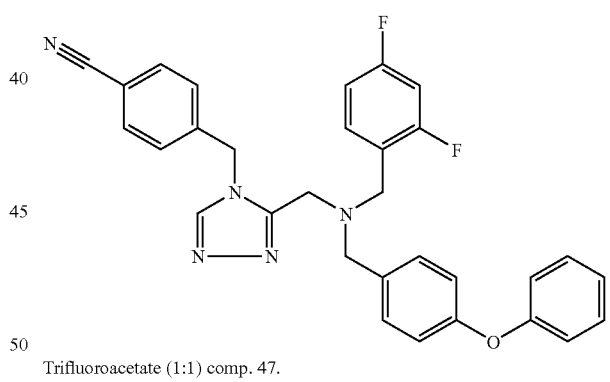
Trifluoroacetate (1:1) comp. 47.
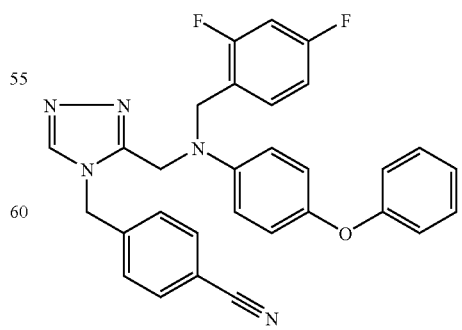
Trifluoroacetate (1:1) comp. 48.

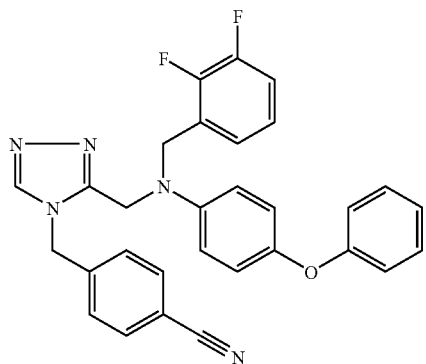
Trifluoroacetate (1:1) comp. 49.
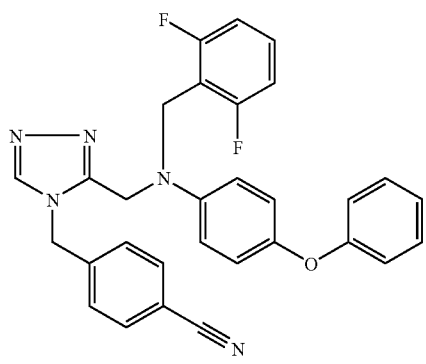
Trifluoroacetate (1:1) comp. 50.
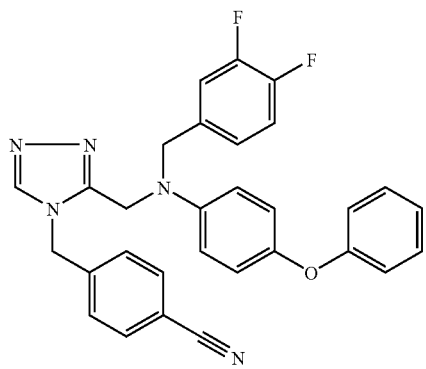
Trifluoroacetate (1:1) comp. 51.
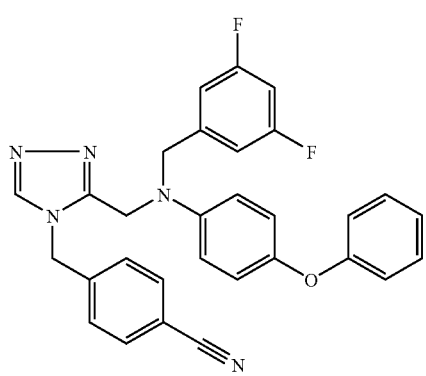
Trifluoroacetate (1:1) comp. 52.
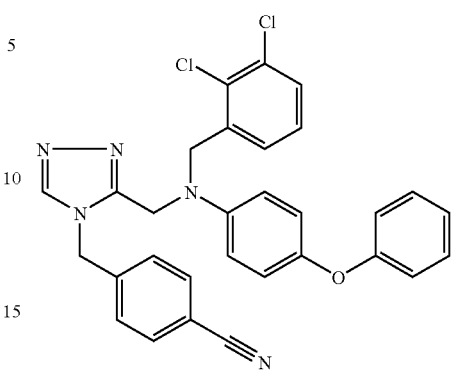
Trifluoroacetate (1:1) comp. 53.
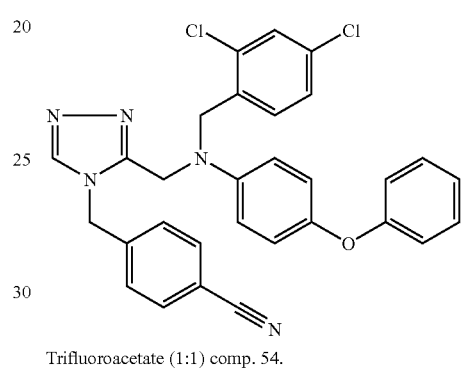
Trifluoroacetate (1:1) comp. 54.
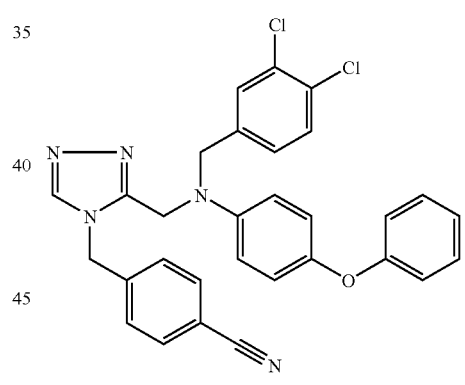
Trifluoroacetate (1:1) comp. 55.
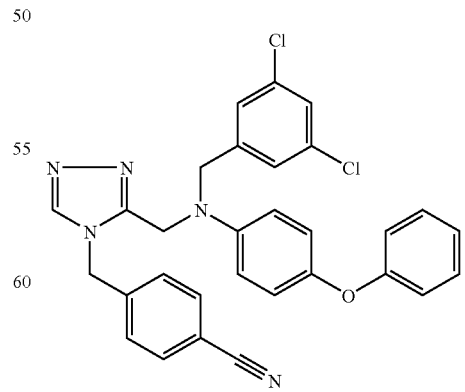
Trifluoroacetate (1:1) comp. 56.

-continued
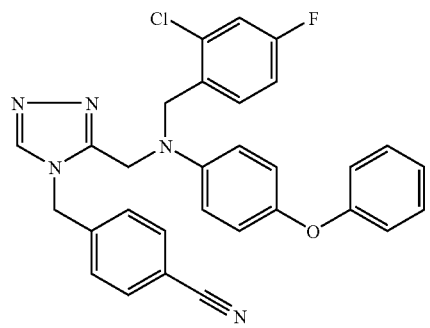
Trifluoroacetate (1:1) comp. 57.
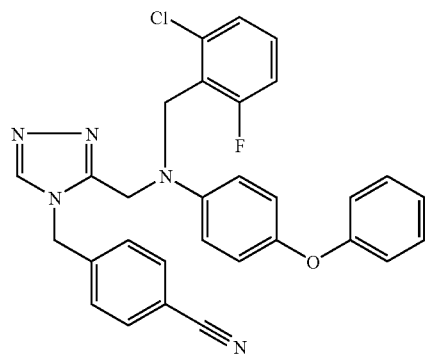
Trifluoroacetate (1:1) comp. 58.
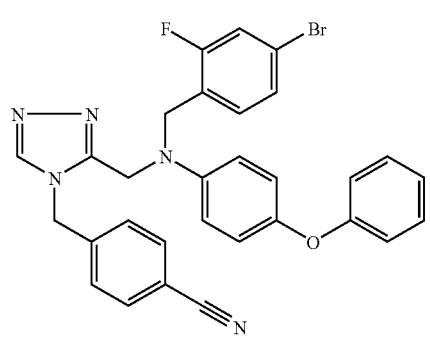
Trifluoroacetate (1:1) comp. 59.
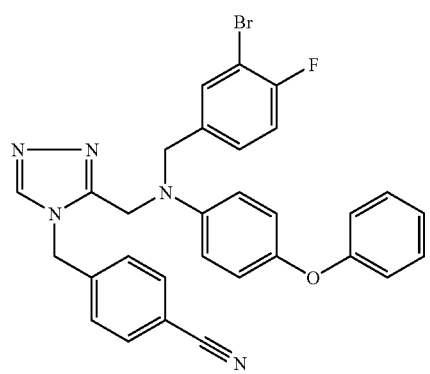
Trifluoroacetate (1:1) comp. 60.
-continued
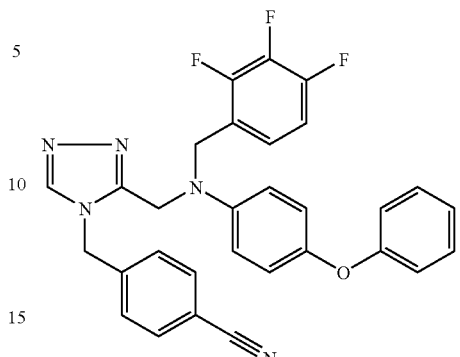
Trifluoroacetate (1:1) comp. 61.
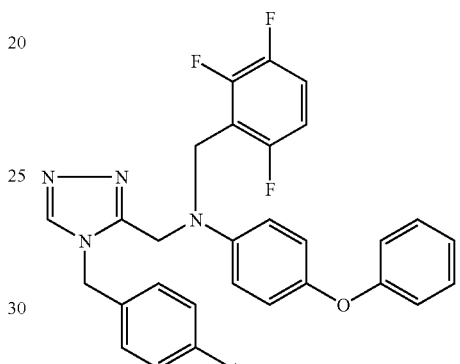
Trifluoroacetate (1:1) comp. 62.
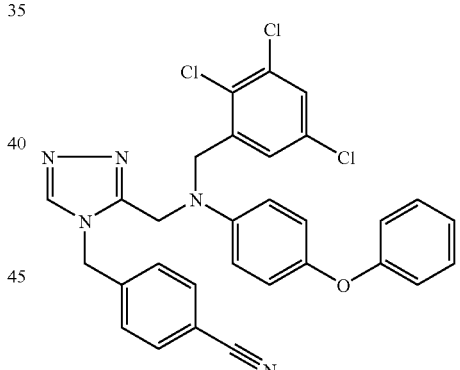
Trifluoroacetate (1:1) comp. 63.
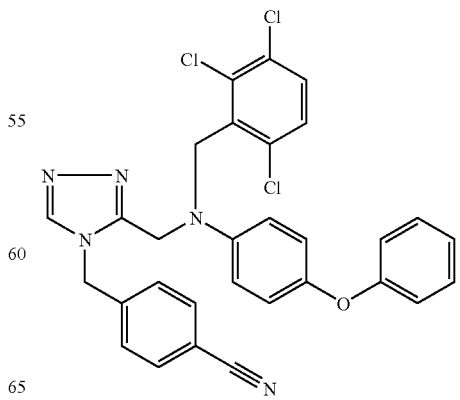
Trifluoroacetate (1:1) comp. 64.

-continued
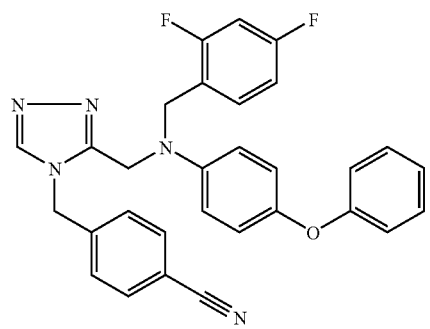
Trifluoroacetate (1:1) comp. 65.
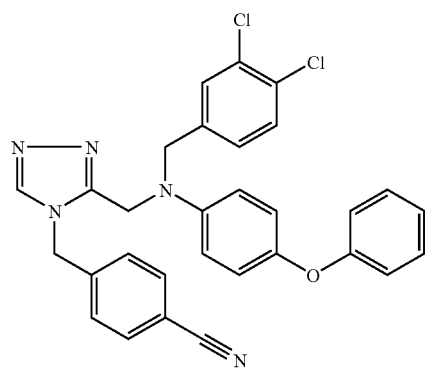
Trifluoroacetate (1:1) comp. 66.
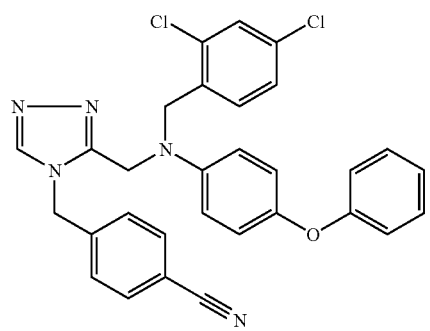
Trifluoroacetate (1:1) comp. 67.
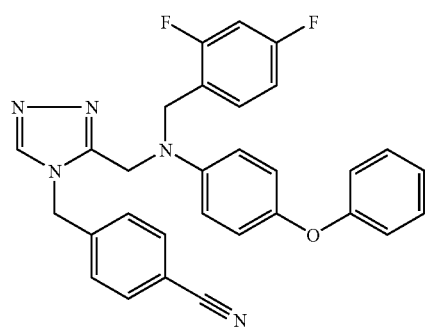
Trifluoroacetate (1:1) comp. 68.
-continued
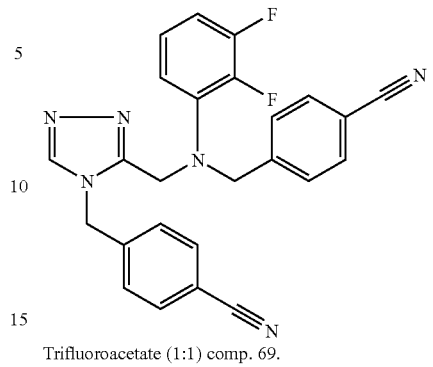
Trifluoroacetate (1:1) comp. 69.
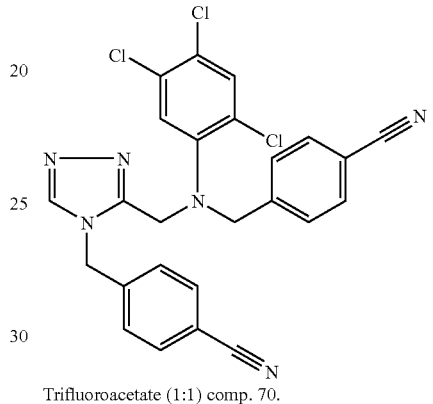
Trifluoroacetate (1:1) comp. 70.
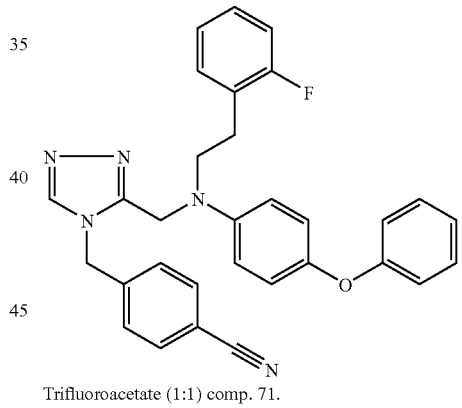
Trifluoroacetate (1:1) comp. 71.
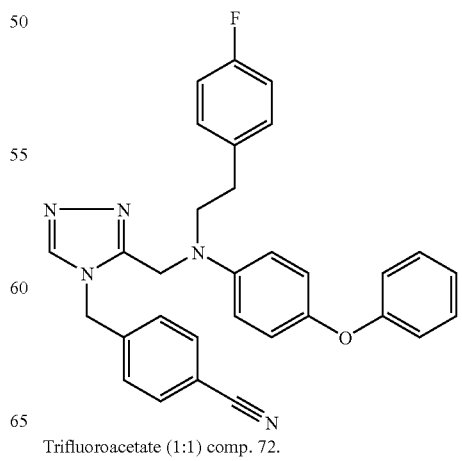
Trifluoroacetate (1:1) comp. 72.

-continued
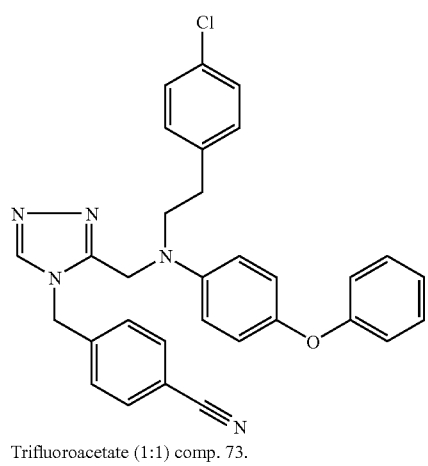
Trifluoroacetate (1:1) comp. 73.
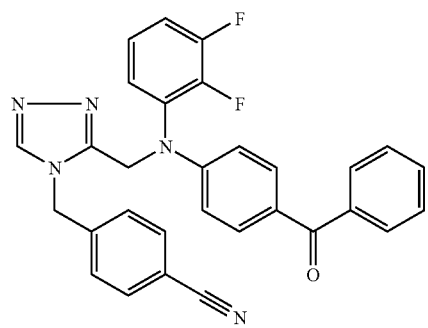
Trifluoroacetate (1:1) comp. 74.
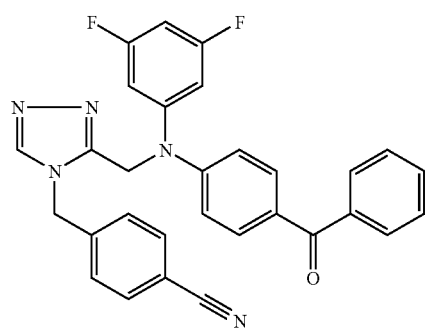
Trifluoroacetate (1:1) comp. 75.
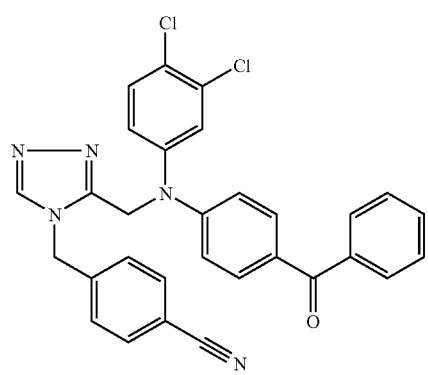
Trifluoroacetate (1:1) comp. 76.
-continued
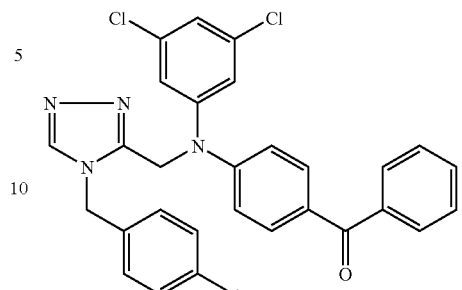
Trifluoroacetate (1:1) comp. 77.
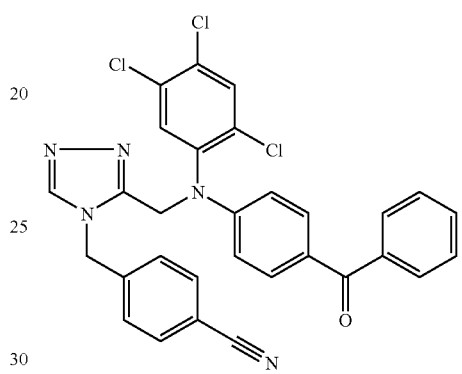
Trifluoroacetate (1:1) comp. 78.
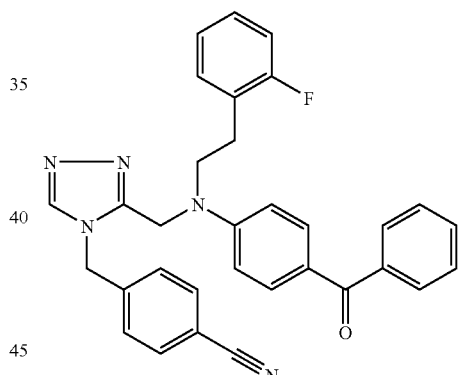
Trifluoroacetate (1:1) comp. 79.
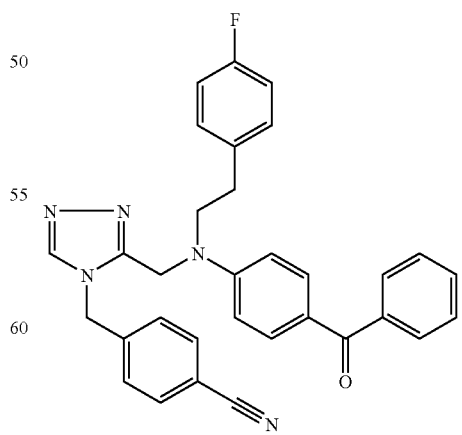
Trifluoroacetate (1:1) comp. 80.

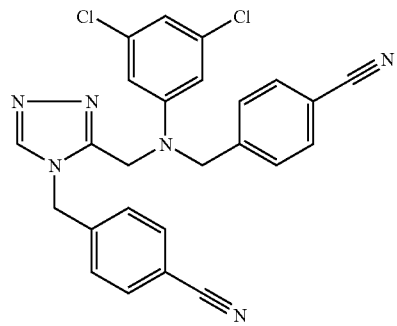
Trifluoroacetate (1:1) comp. 81.
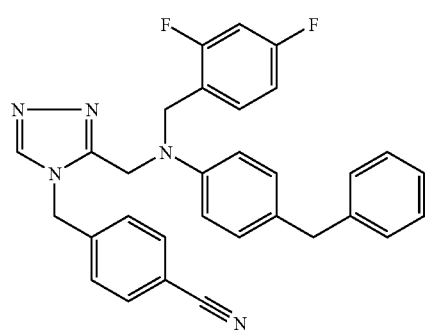
Trifluoroacetate (1:1) comp. 82.
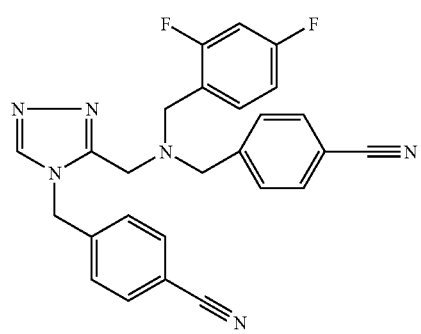
Trifluoroacetate (1:1) comp. 83.
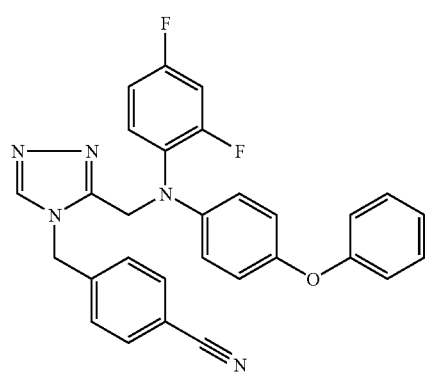
Trifluoroacetate (1:1) comp. 84.
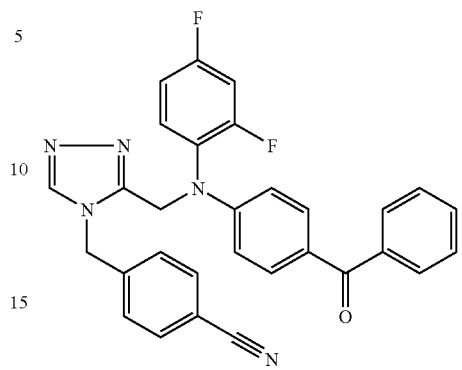
Trifluoroacetate (1:1) comp. 85.
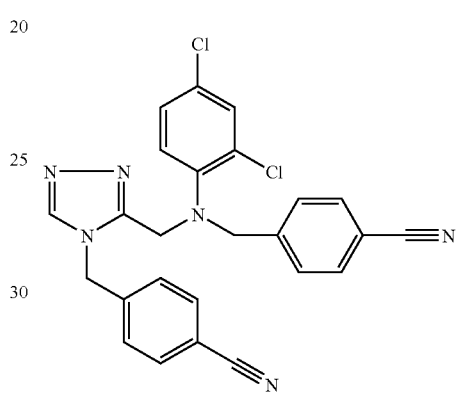
Trifluoroacetate (1:1) comp. 86.
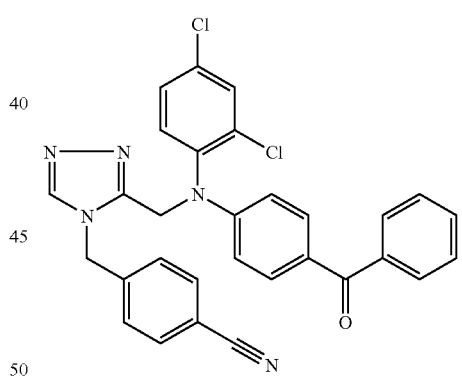
Trifluoroacetate (1:1) comp. 87.
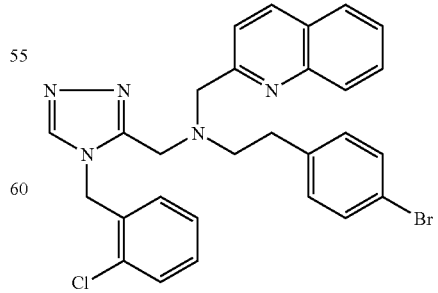
Trifluoroacetate (1:1) comp. 88.

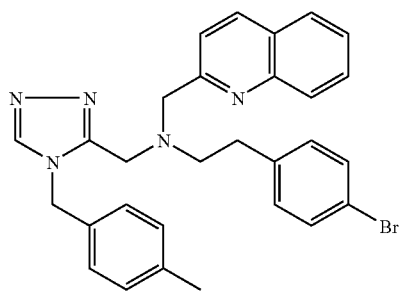
Trifluoroacetate (1:1) comp. 89.
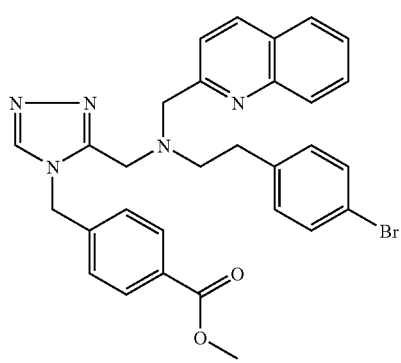
Trifluoroacetate (1:1) comp. 90.
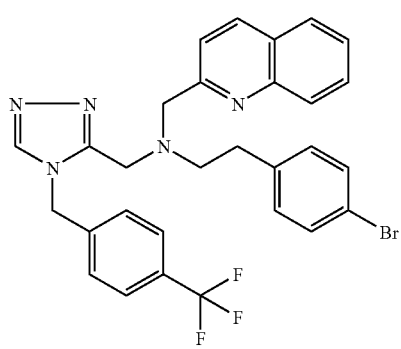
R168843 Trifluoroacetate (1:1) comp. 91.
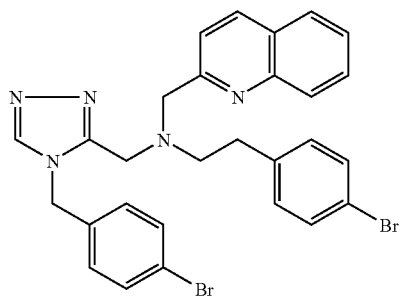
Trifluoroacetate (1:1) comp. 92.
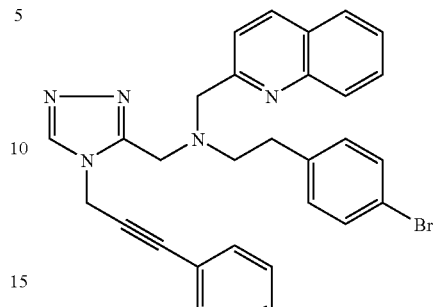
Trifluoroacetate (1:1) comp. 93.
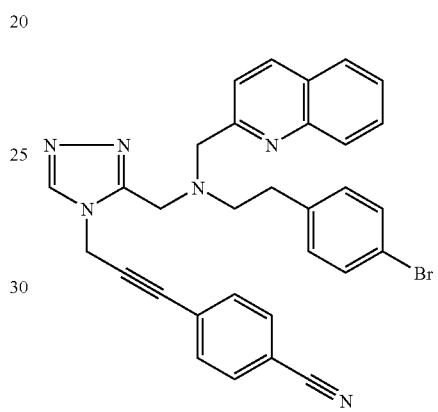
Trifluoroacetate (1:1) comp. 94.
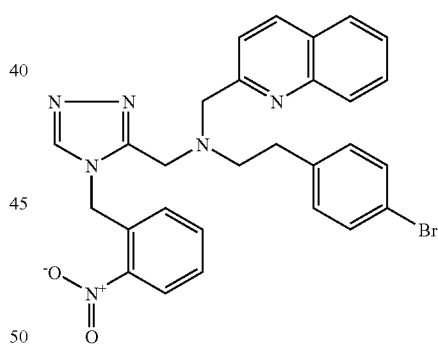
Trifluoroacetate (1:1) comp. 95.
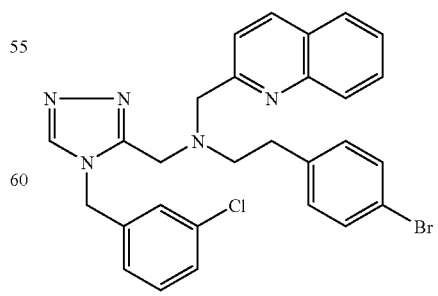
Trifluoroacetate (1:1) comp. 96.

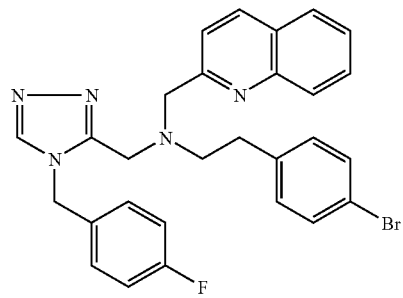
Trifluoroacetate (1:1) comp. 97.
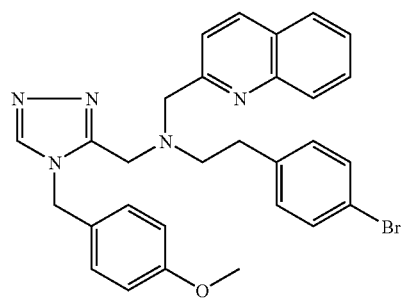
Trifluoroacetate (1:1) comp. 98.
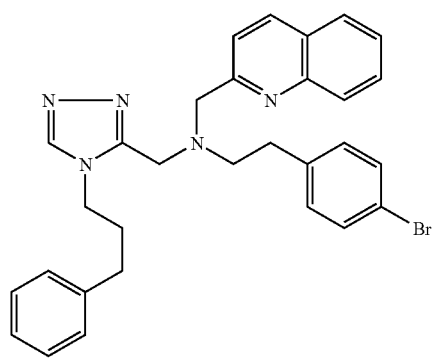
Trifluoroacetate (1:1) comp. 99.
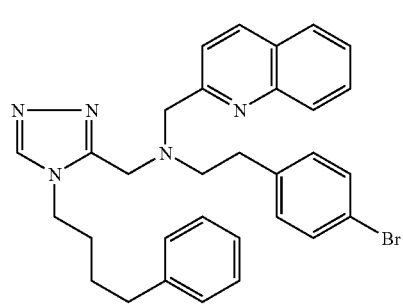
Trifluoroacetate (1:1) comp. 100.
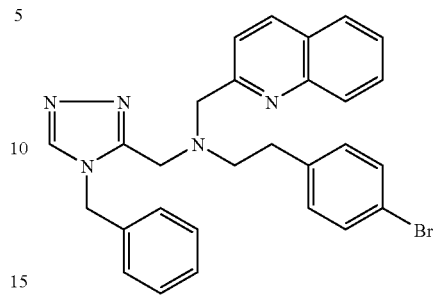
Trifluoroacetate (1:1) comp. 101.
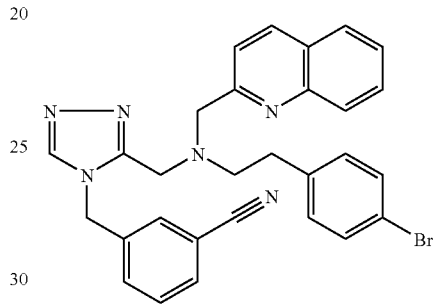
Trifluoroacetate (1:1) comp. 102.
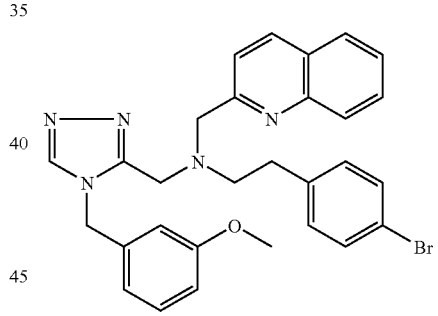
Trifluoroacetate (1:1) comp. 103.
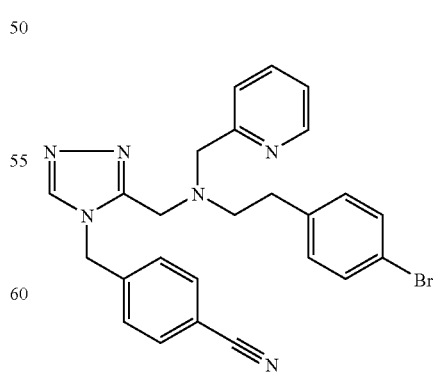
Trifluoroacetate (1:1) comp. 104.

-continued
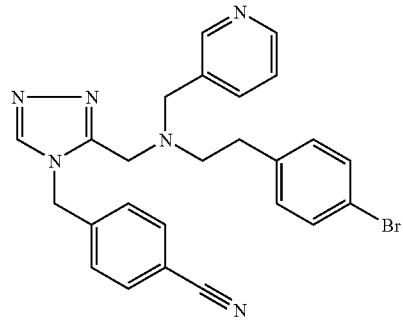
Trifluoroacetate (1:1) comp. 105.
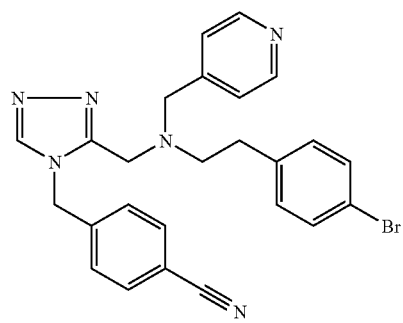
Trifluoroacetate (1:1) comp. 106.
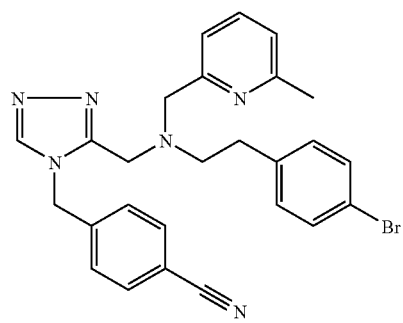
Trifluoroacetate (1:1) comp. 107.
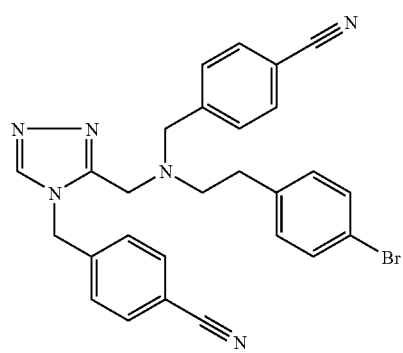
Trifluoroacetate (1:1) comp. 108.
-continued
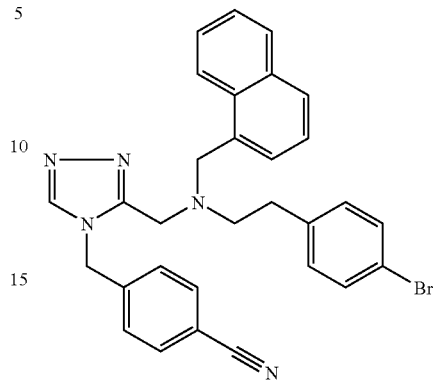
Trifluoroacetate (1:1) comp. 109.
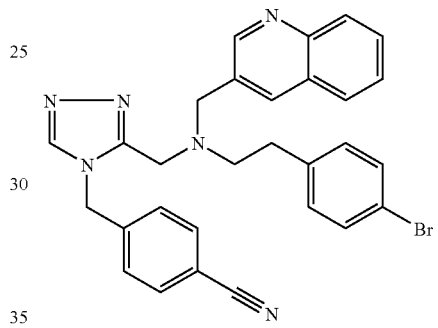
Trifluoroacetate (1:1) comp. 110.
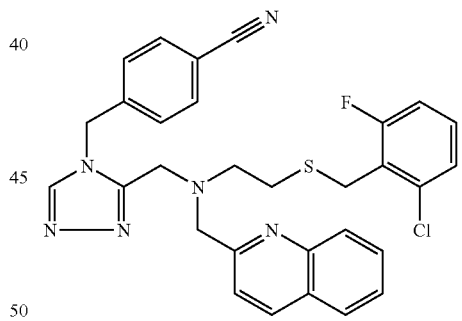
Trifluoroacetate (1:1) comp. 111.
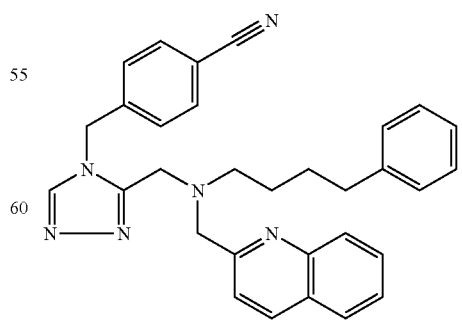
Trifluoroacetate (1:1) comp. 112.

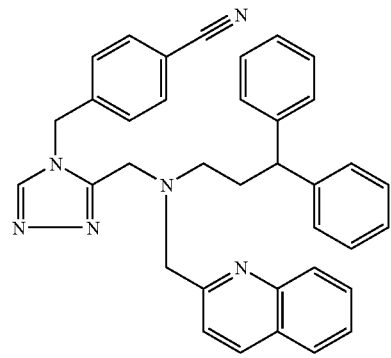
Trifluoroacetate (1:1) comp. 113.
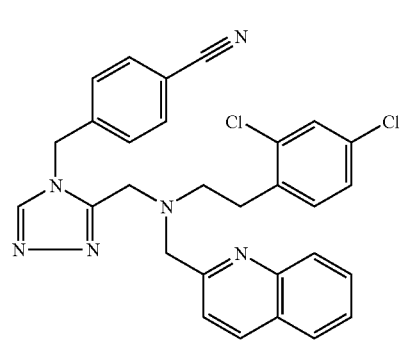
Trifluoroacetate (1:1) comp. 114.
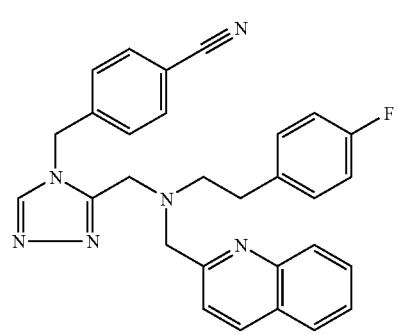
Trifluoroacetate (1:1) comp. 115.
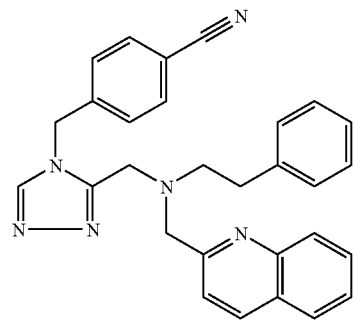
Trifluoroacetate (1:1) comp. 116.
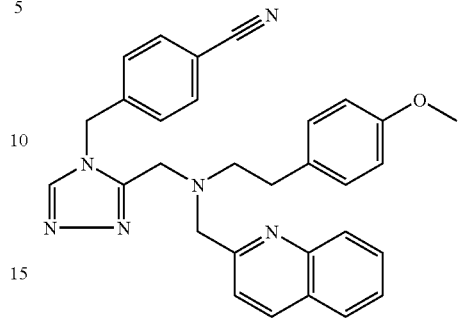
Trifluoroacetate (1:1) comp. 117.
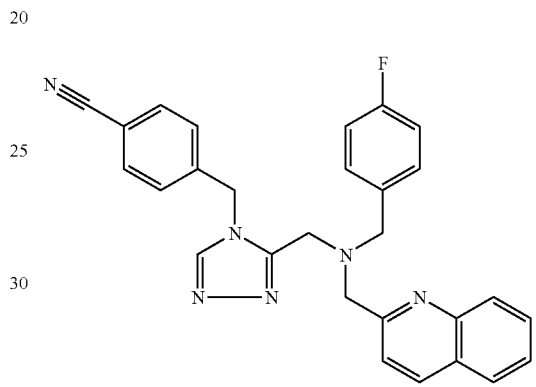
Trifluoroacetate (1:1) comp. 118.
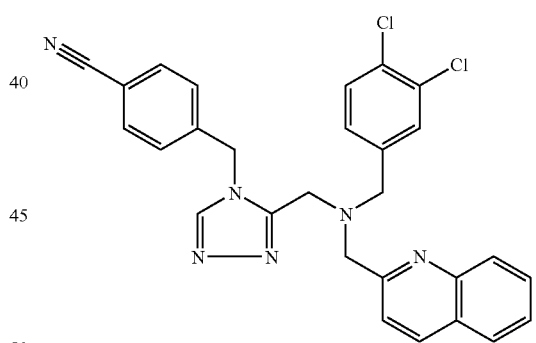
Trifluoroacetate (1:1) comp. 119.
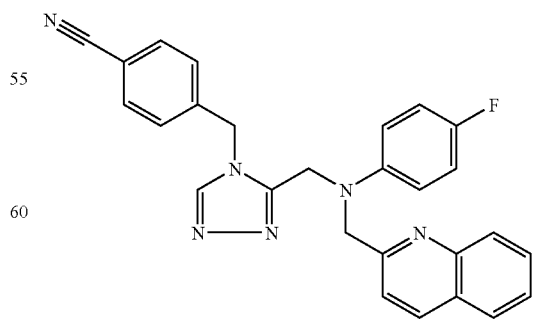
Trifluoroacetate (1:1) comp. 120.

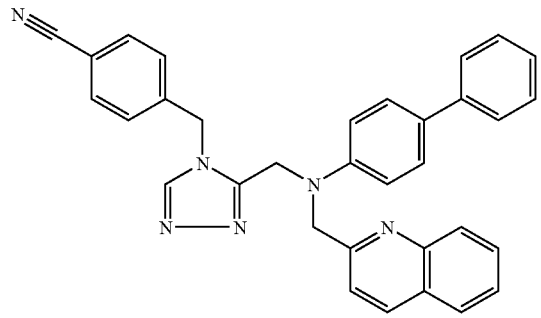
Trifluoroacetate (1:1) comp. 121.
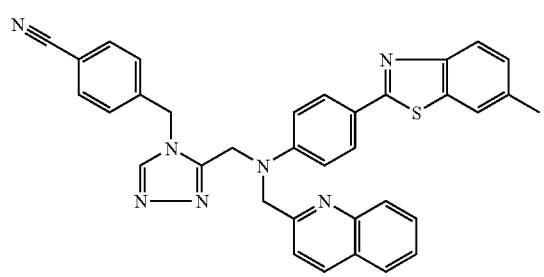
Trifluoroacetate (1:1) comp. 122.
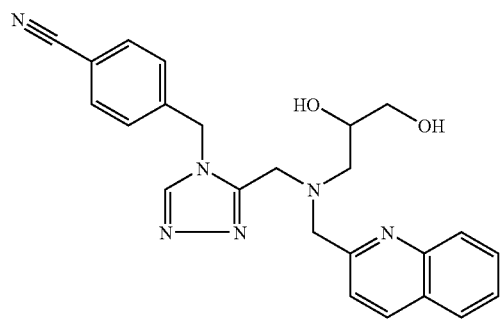
Trifluoroacetate (1:1) comp. 123.
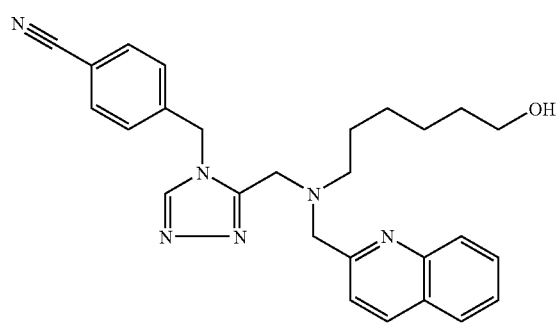
Trifluoroacetate (1:1) comp. 124.
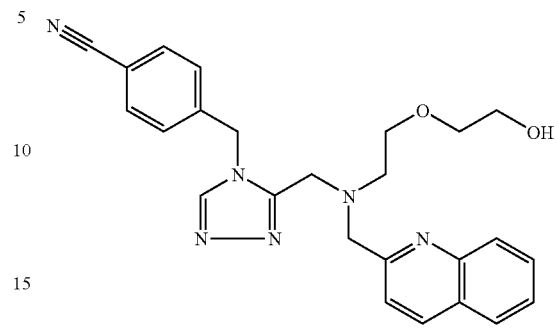
Trifluoroacetate (1:1) comp. 125.
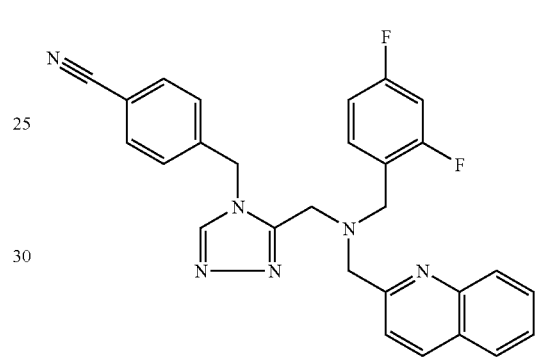
Trifluoroacetate (1:1) comp. 126.
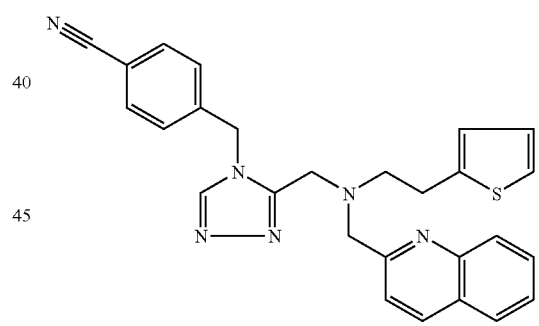
Trifluoroacetate (1:1) comp. 127.
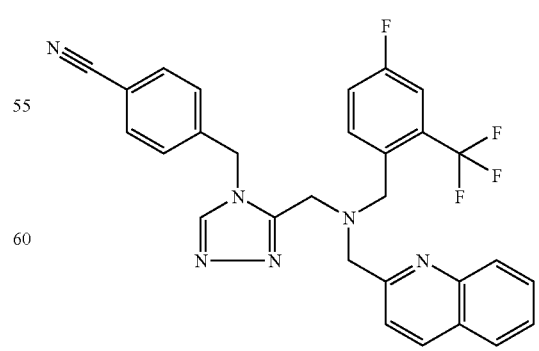
Trifluoroacetate (1:1) comp. 128.

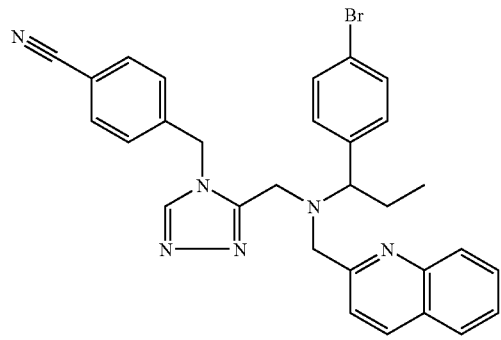
Trifluoroacetate (1:1) comp. 129.
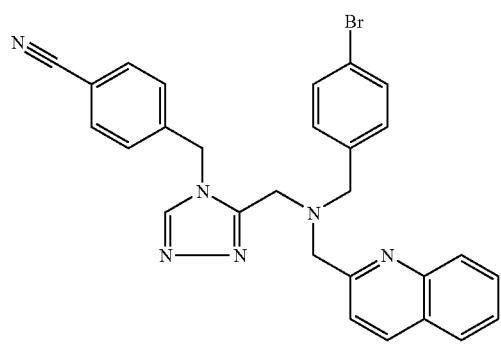
Trifluoroacetate (1:1) comp. 130.
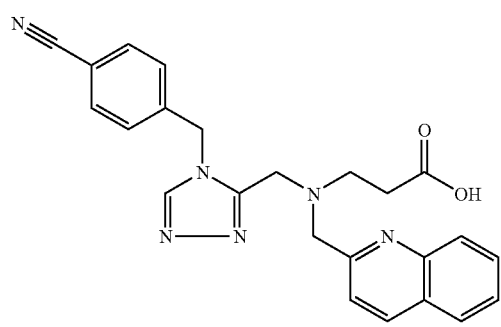
Trifluoroacetate (1:1) comp. 131.
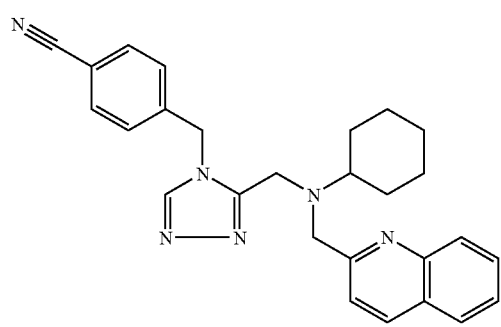
Trifluoroacetate (1:1) comp. 132.
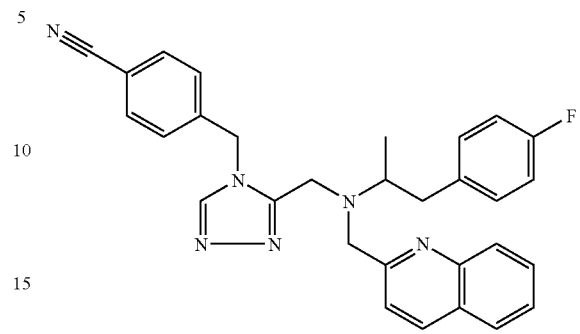
Trifluoroacetate (1:1) comp. 133.
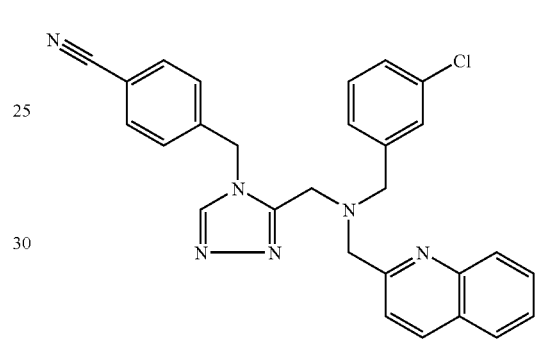
Trifluoroacetate (1:1) comp. 134.
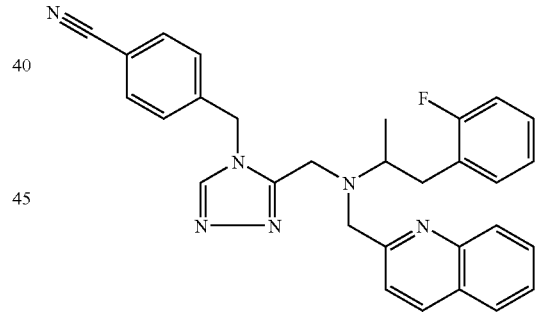
Trifluoroacetate (1:1) comp. 135.
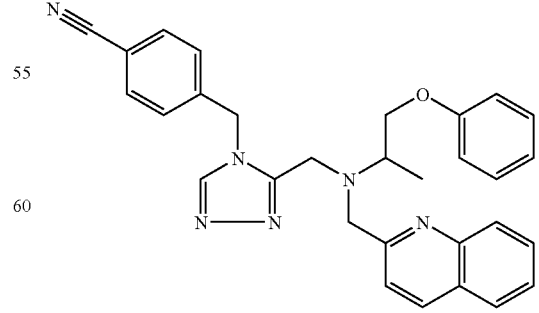
Trifluoroacetate (1:1) comp. 136.

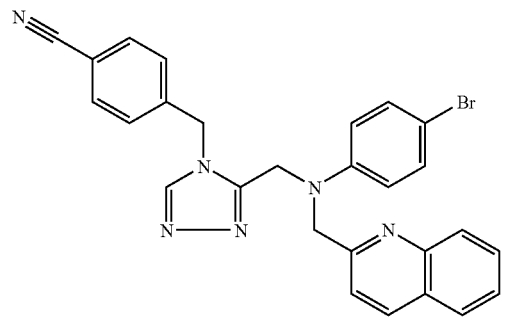
Trifluoroacetate (1:1) comp. 137.
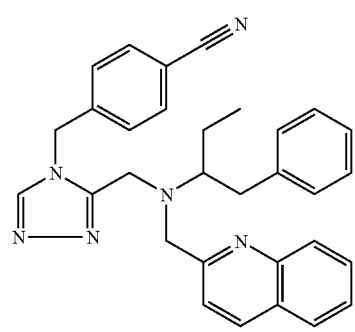
Trifluoroacetate (1:1) comp. 138.
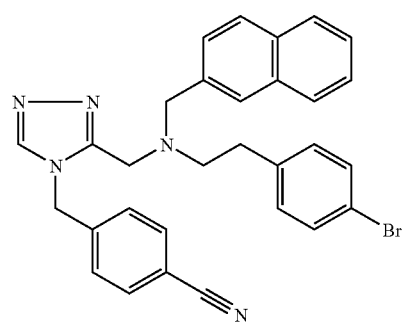
Trifluoroacetate (1:1) comp. 139.
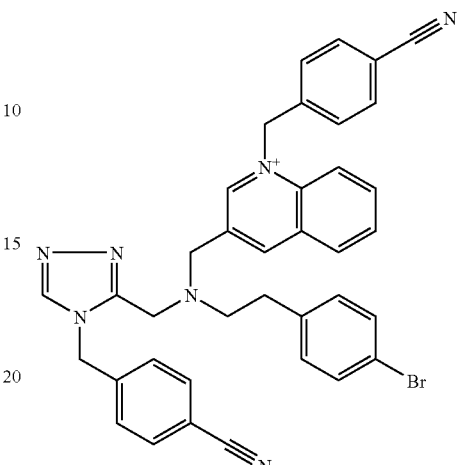
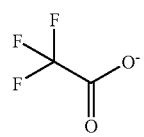
Trifluoroacetate (1:1) comp. 140.
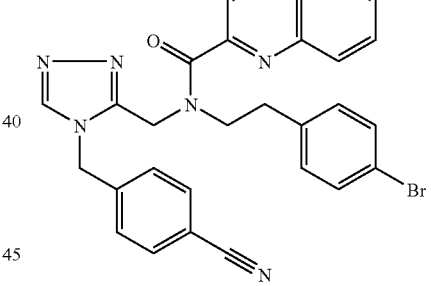
Trifluoroacetate (1:1) comp. 141.
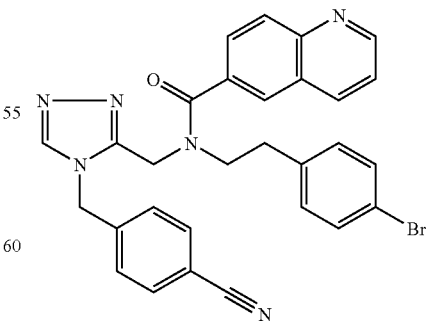
Trifluoroacetate (1:1) comp. 142.

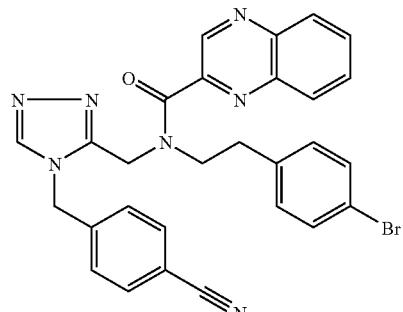
Trifluoroacetate (1:1) comp. 143.
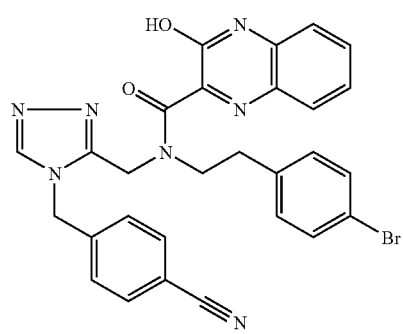
Trifluoroacetate (1:1) comp. 144.
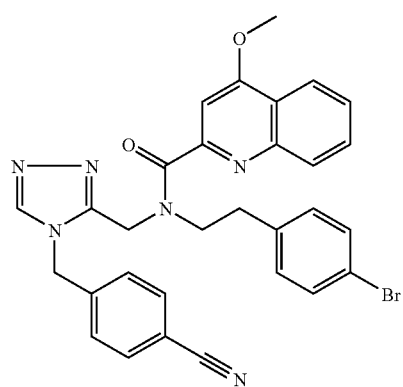
Trifluoroacetate (1:1) comp. 145.
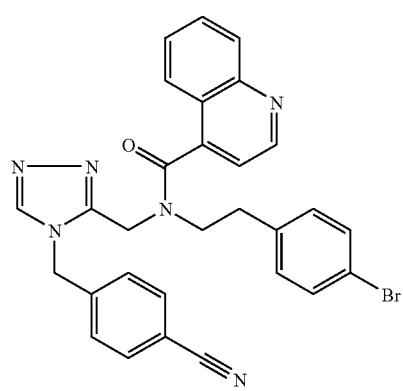
Trifluoroacetate (1:1) comp. 146.
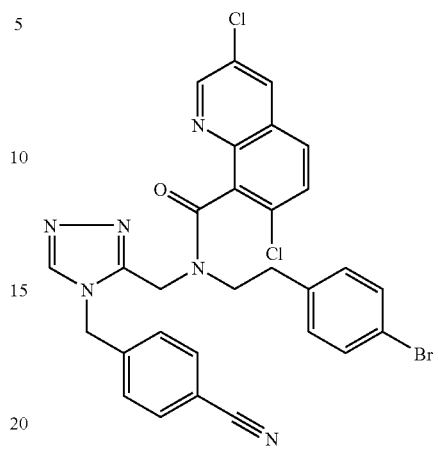
Trifluoroacetate (1:1) comp. 147.
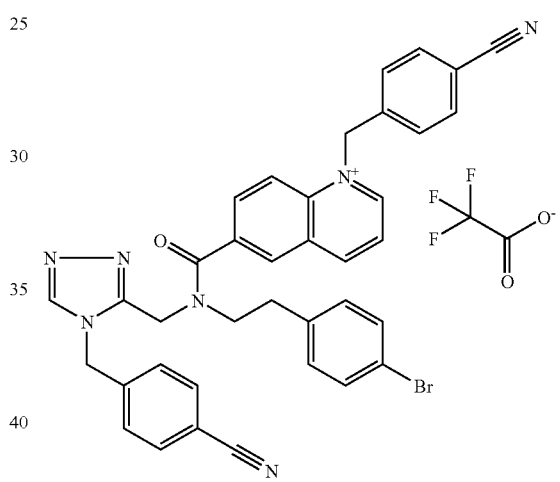
Trifluoroacetate (1:1) comp. 148.
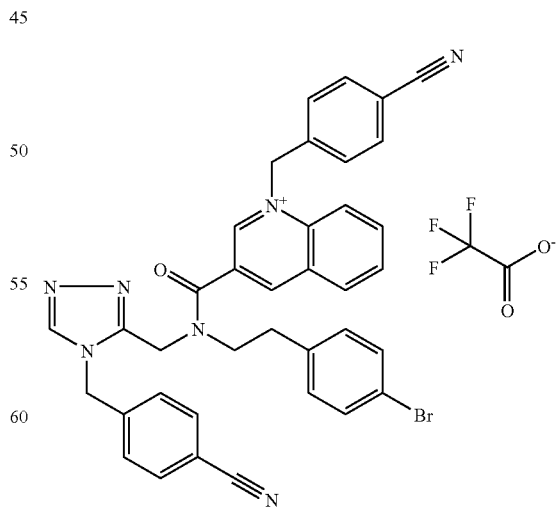
Trifluoroacetate (1:1) comp. 149.

-continued
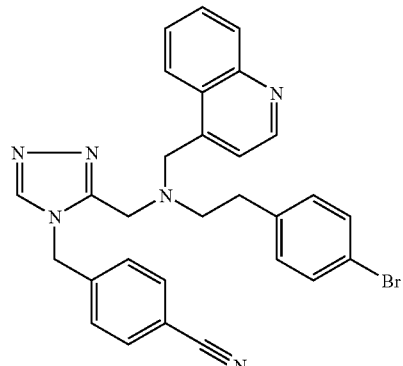
Trifluoroacetate (1:1) comp. 150.
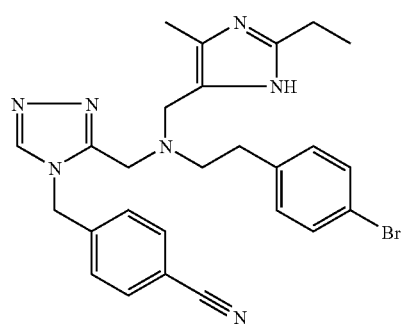
Trifluoroacetate (1:1) comp. 151.
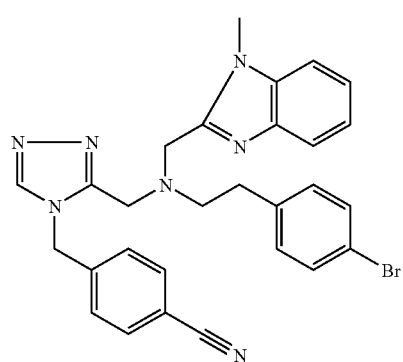
Trifluoroacetate (1:1) comp. 152.
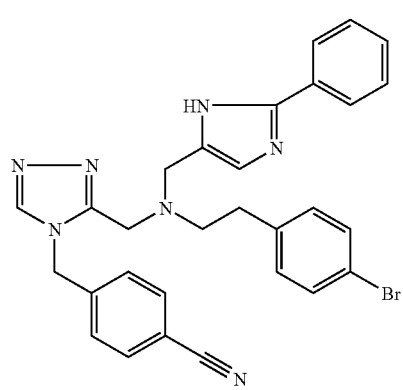
Trifluoroacetate (1:1) comp. 153.
-continued
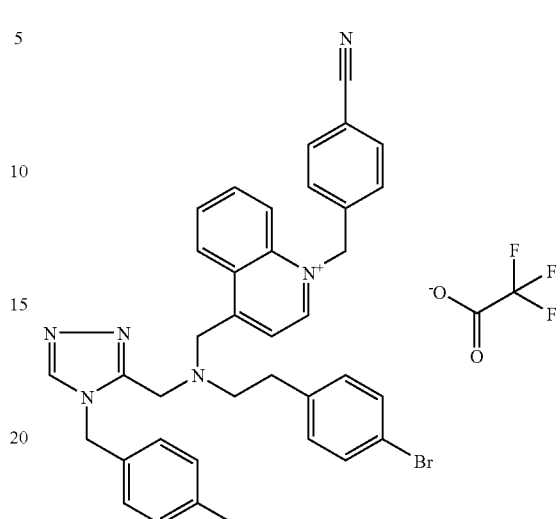
Trifluoroacetate (1:1) comp. 154.
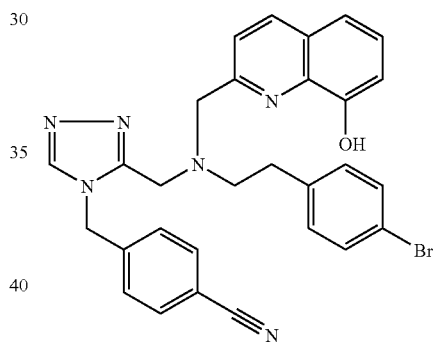
Trifluoroacetate (1:1) comp. 155.
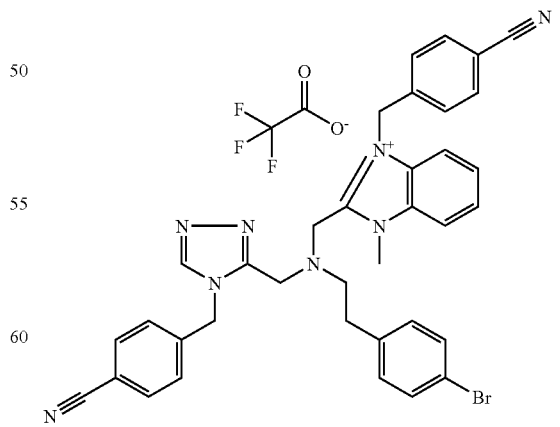
Trifluoroacetate (1:1) comp. 156.

-continued
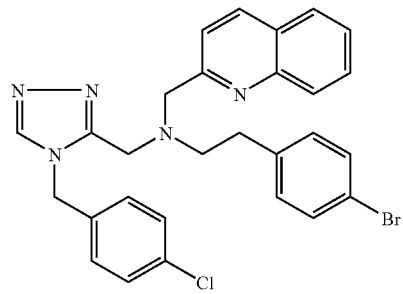
Trifluoroacetate (1:1) comp. 157.
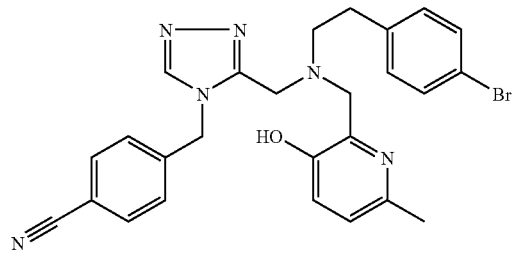
Trifluoroacetate (1:1) comp. 158.
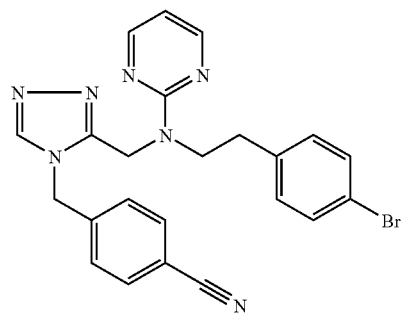
Trifluoroacetate (1:1) comp. 159.
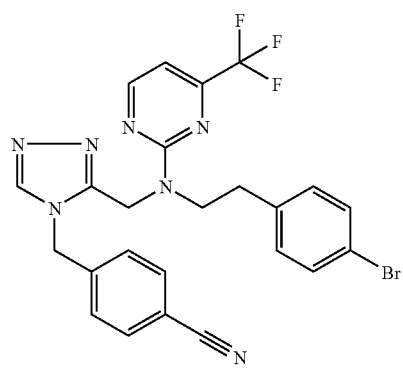
Trifluoroacetate (1:1) comp. 160.
-continued
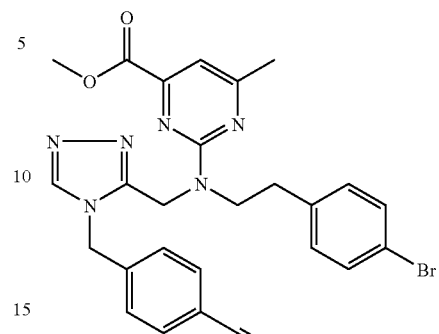
Trifluoroacetate (1:1) comp. 161.
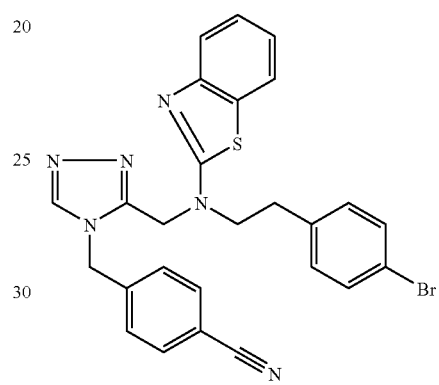
Trifluoroacetate (1:1) comp. 162.
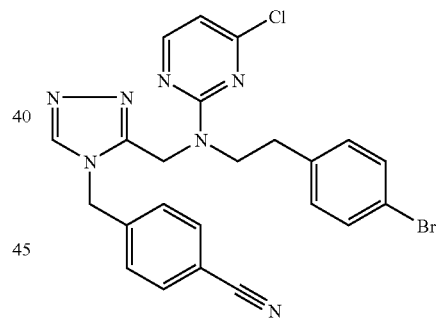
Trifluoroacetate (1:1) comp. 163.
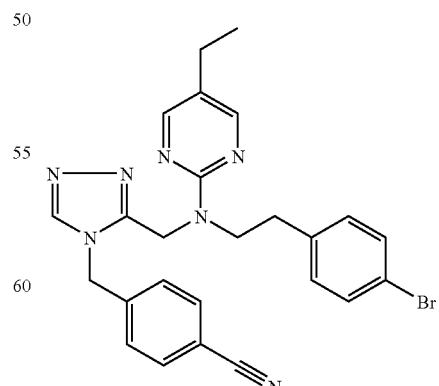
Trifluoroacetate (1:1) comp. 164.

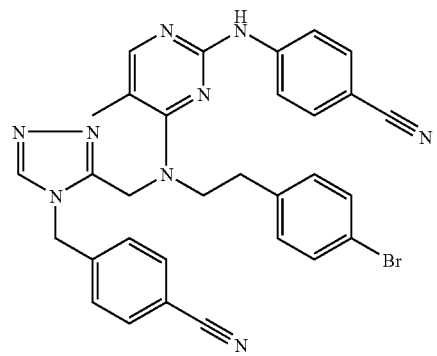
Trifluoroacetate (1:1) comp. 165.
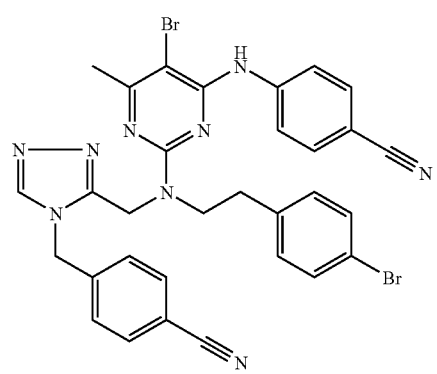
Trifluoroacetate (1:1) comp. 166.
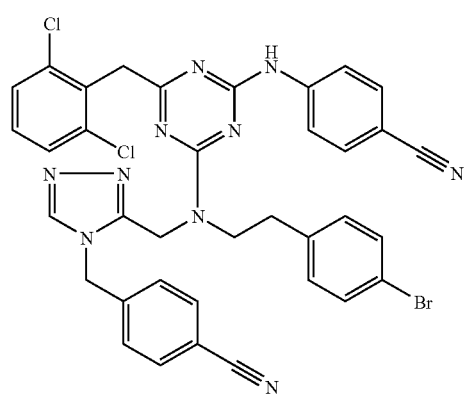
Trifluoroacetate (1:1) comp. 167.
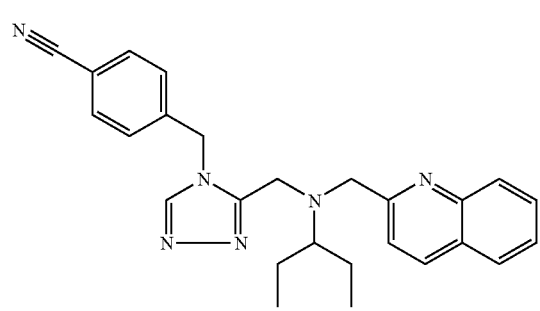
Trifluoroacetate (1:1) comp. 168.
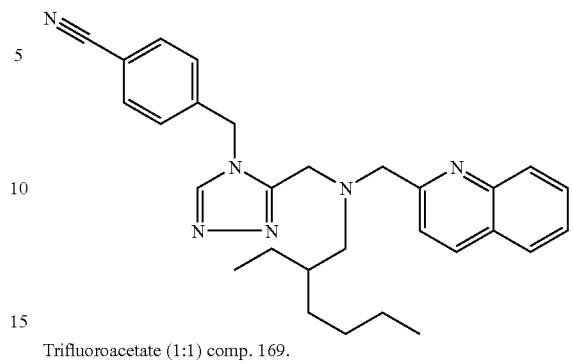
Trifluoroacetate (1:1) comp. 169.
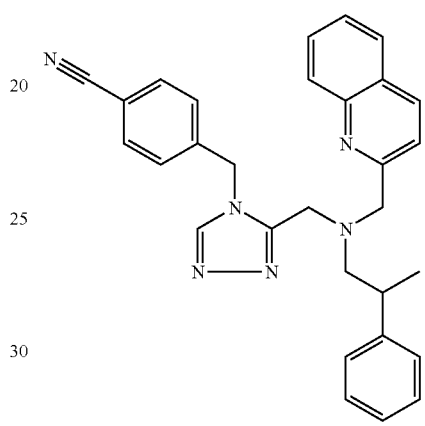
Trifluoroacetate (1:1) comp. 170.
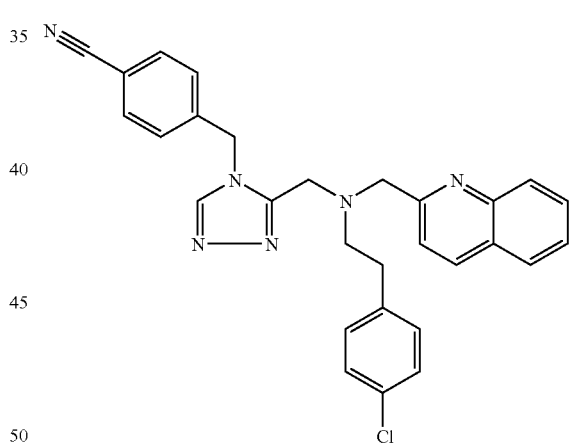
Trifluoroacetate (1:1) comp. 171.
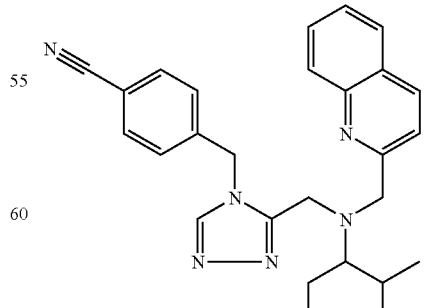
Trifluoroacetate (1:1) comp. 172.

-continued
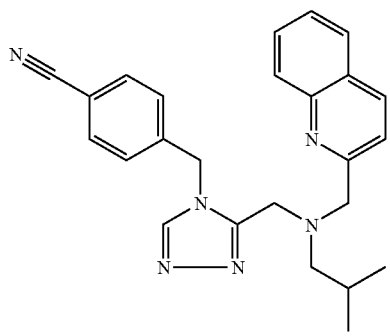
Trifluoroacetate (1:1) comp. 173.
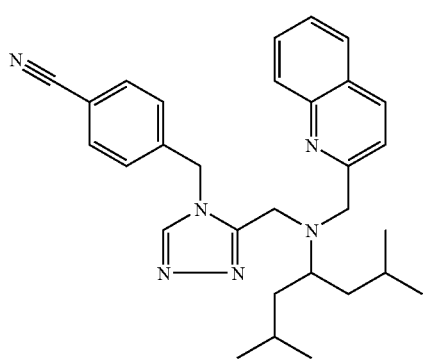
Trifluoroacetate (1:1) comp. 174.
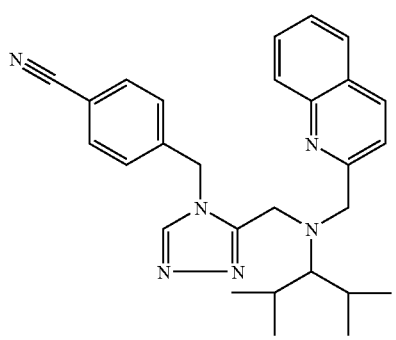
Trifluoroacetate (1:1) comp. 175.
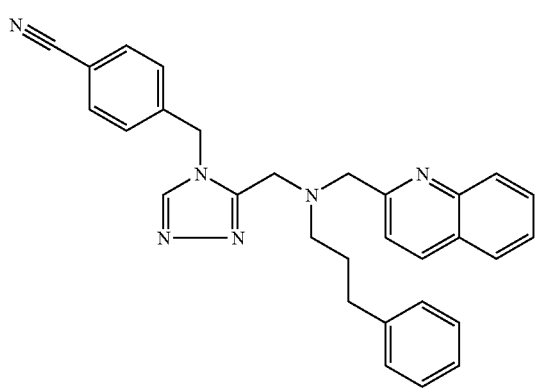
Trifluoroacetate (1:1) comp. 176.
-continued
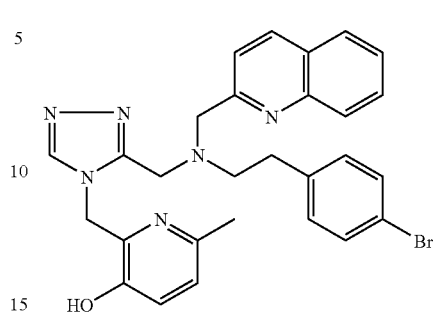
Trifluoroacetate (1:1) comp. 177.
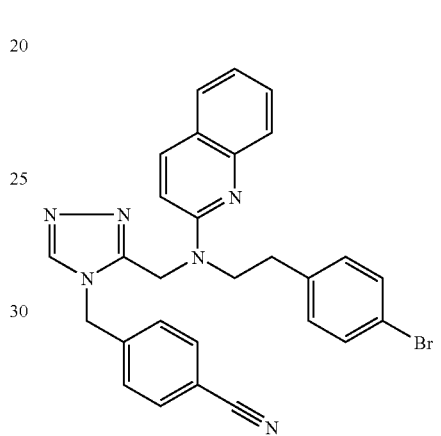
Trifluoroacetate (1:1) comp. 178.
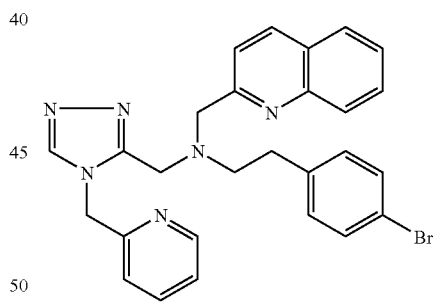
Trifluoroacetate (1:1) comp. 179.
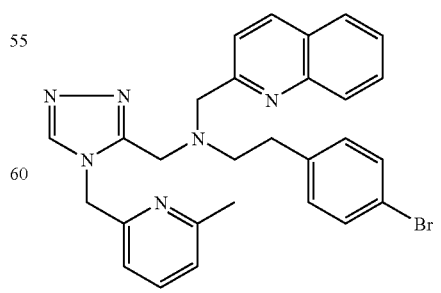
Trifluoroacetate (1:1) comp. 180.

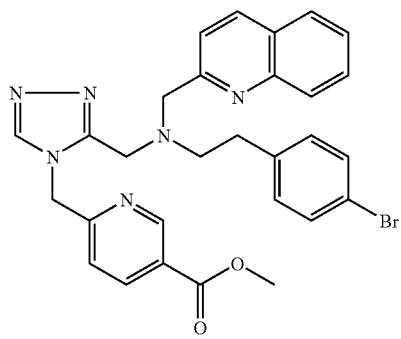
Trifluoroacetate (1:1) comp. 181.
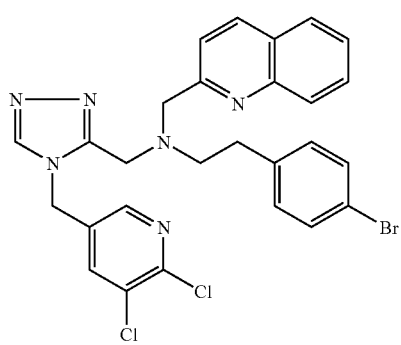
Trifluoroacetate (1:1) comp. 182.
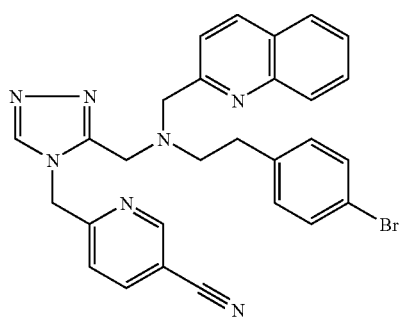
Trifluoroacetate (1:1) comp. 183.
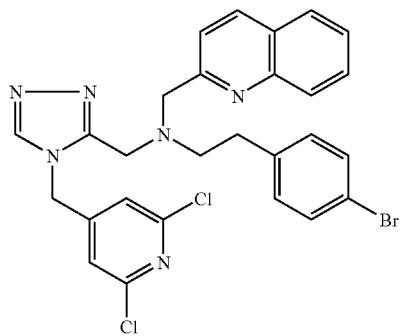
Trifluoroacetate (1:1) comp. 184.
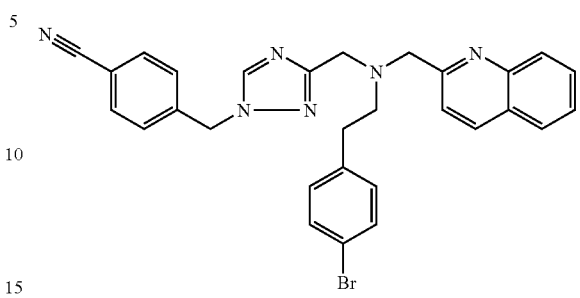
Trifluoroacetate (1:1) comp. 185.
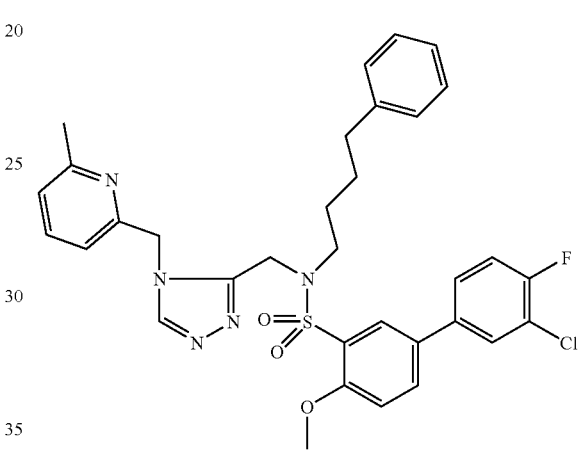
Trifluoroacetate (1:1) comp. 186.
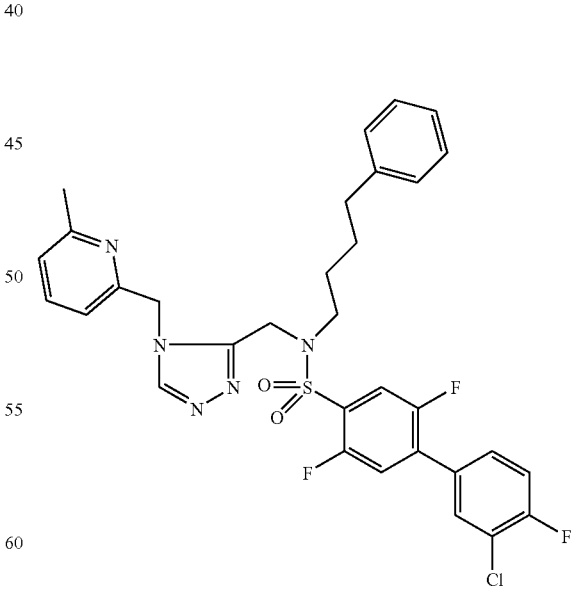
Trifluoroacetate (1:1) comp. 187.

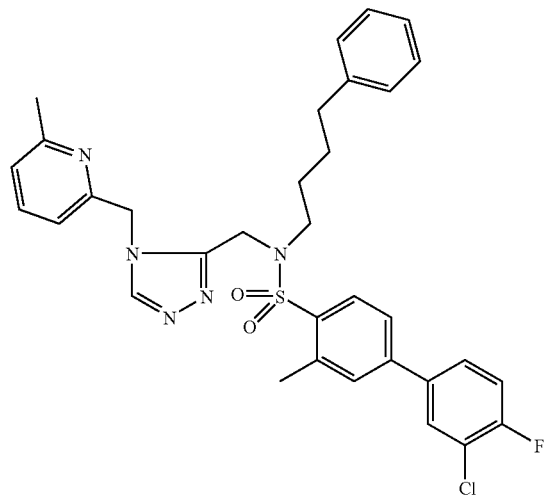
Trifluoroacetate (1:1) comp. 188.
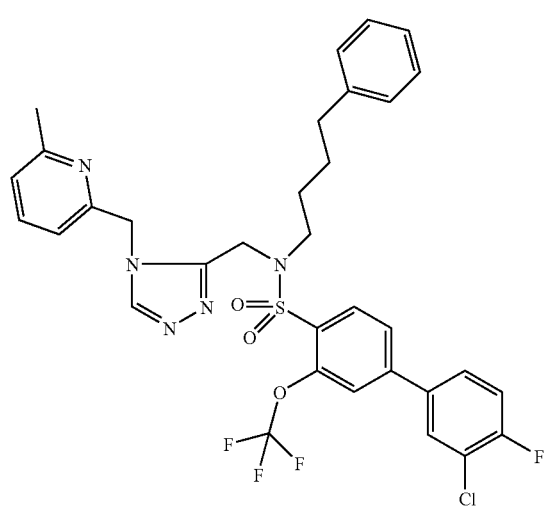
Trifluoroacetate (1:1) comp. 189.
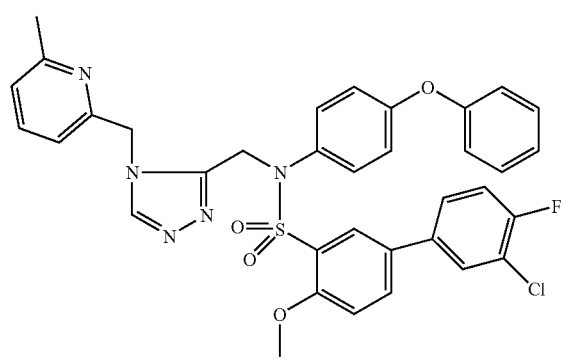
Trifluoroacetate (1:1) comp. 190.
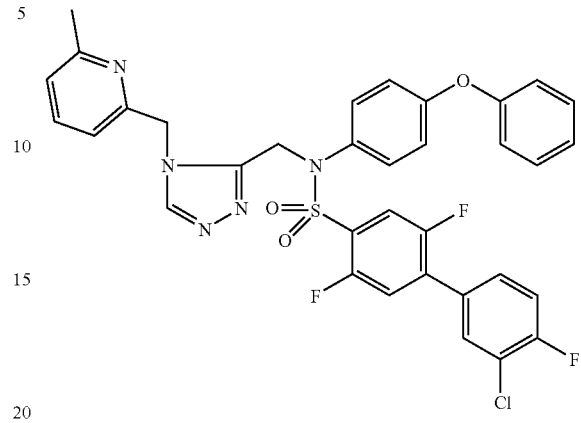
Trifluoroacetate (1:1) comp. 191.
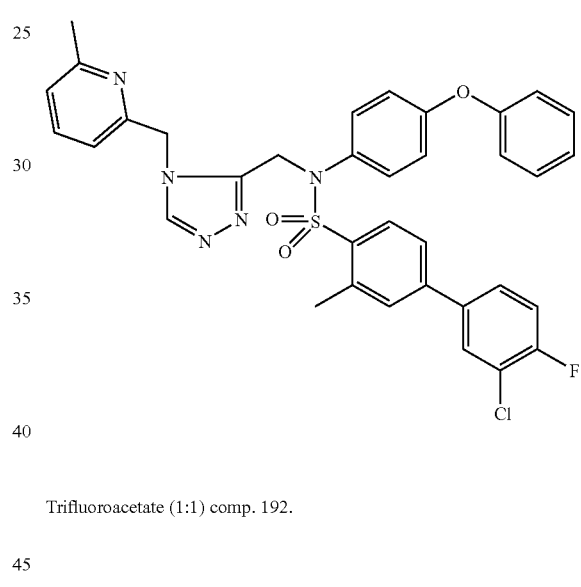
Trifluoroacetate (1:1) comp. 192.
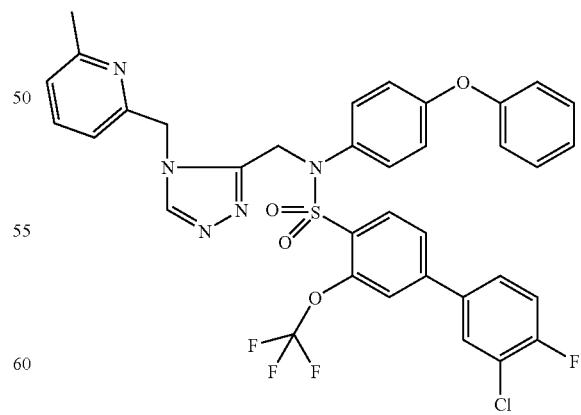
Trifluoroacetate (1:1) comp. 193.

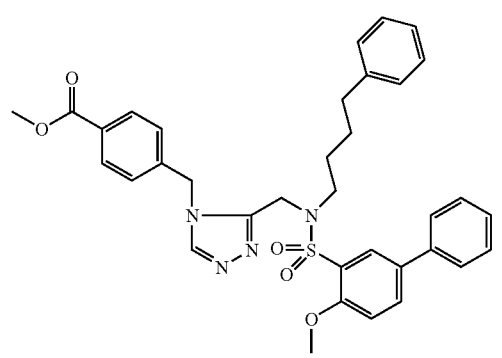
Trifluoroacetate (1:1) comp. 194.
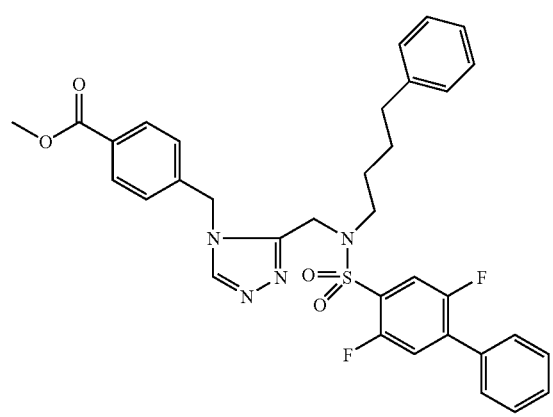
Trifluoroacetate (1:1) comp. 195.
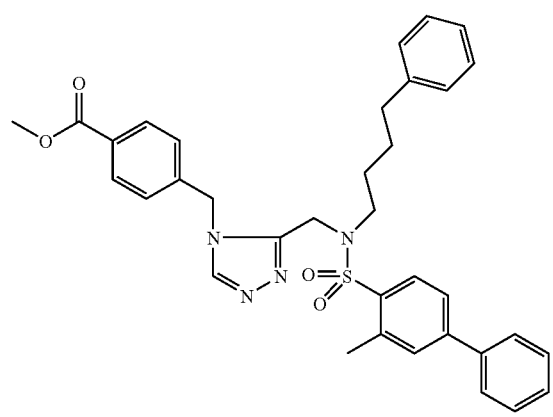
Trifluoroacetate (1:1) comp. 196.
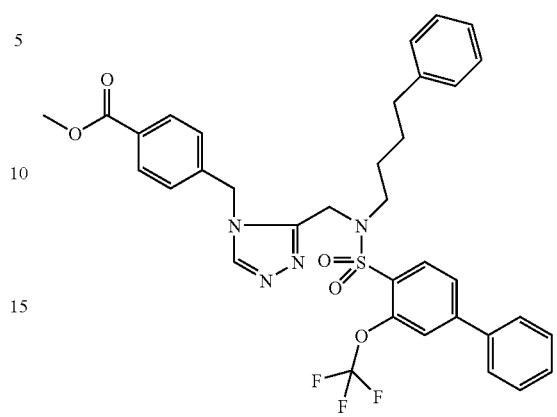
Trifluoroacetate (1:1) comp. 197.
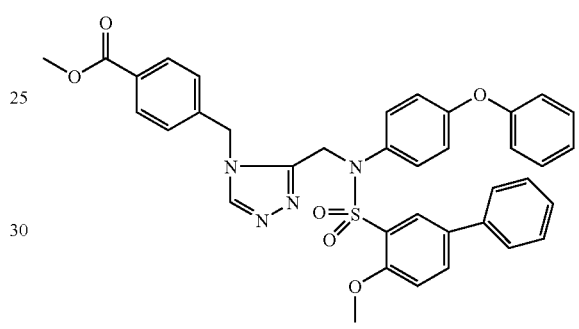
Trifluoroacetate (1:1) comp. 198.
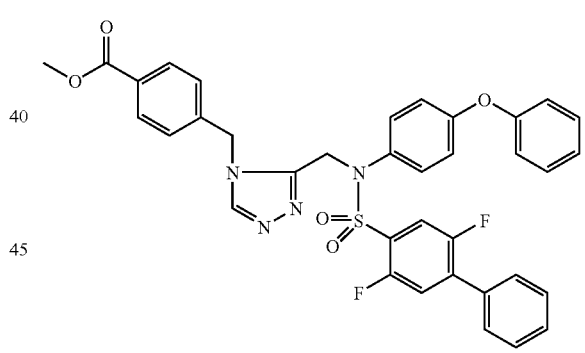
Trifluoroacetate (1:1) comp. 199.
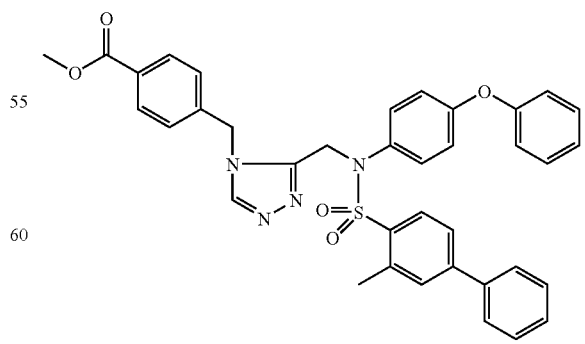
Trifluoroacetate (1:1) comp. 200.

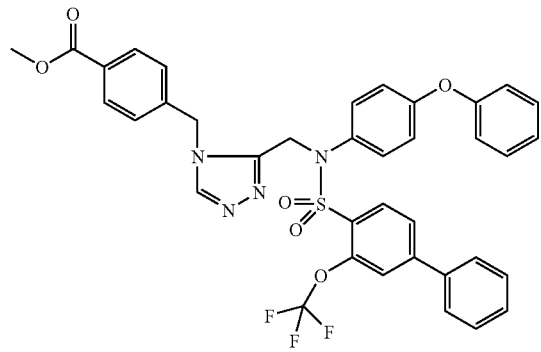
Trifluoroacetate (1:1) comp. 201.
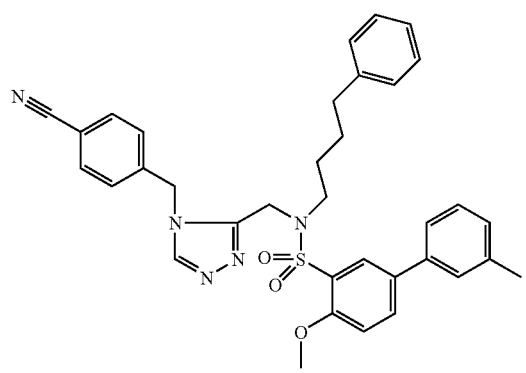
Trifluoroacetate (1:1) comp. 202.
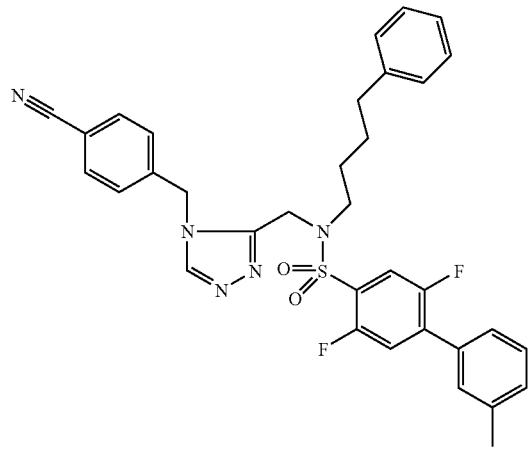
Trifluoroacetate (1:1) comp. 203.
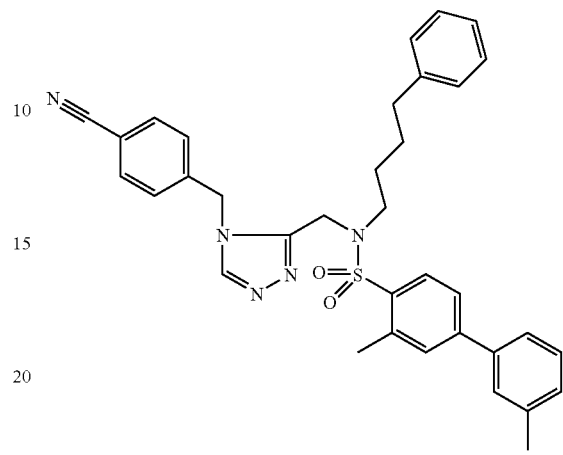
Trifluoroacetate (1:1) comp. 204.
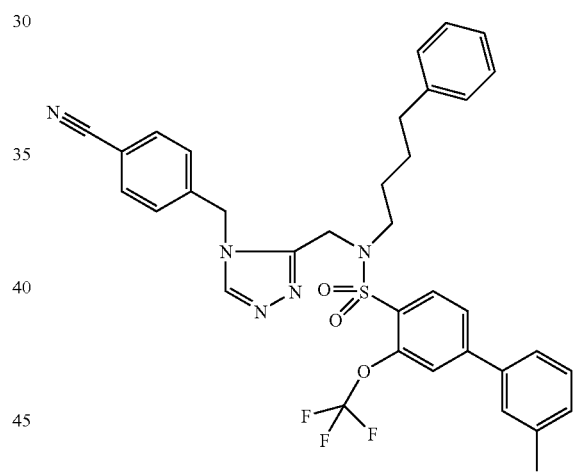
Trifluoroacetate (1:1) comp. 205.
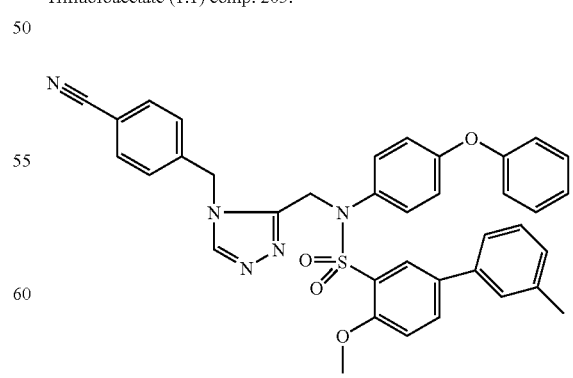
Trifluoroacetate (1:1) comp. 206.

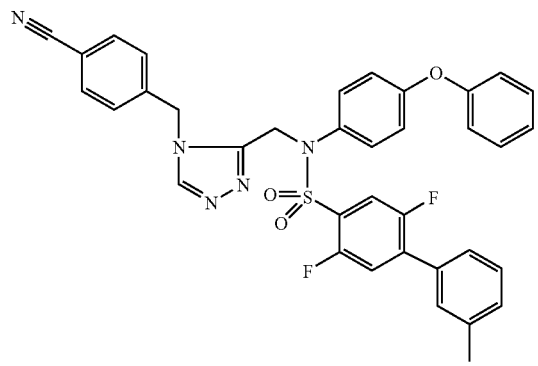
Trifluoroacetate (1:1) comp. 207.
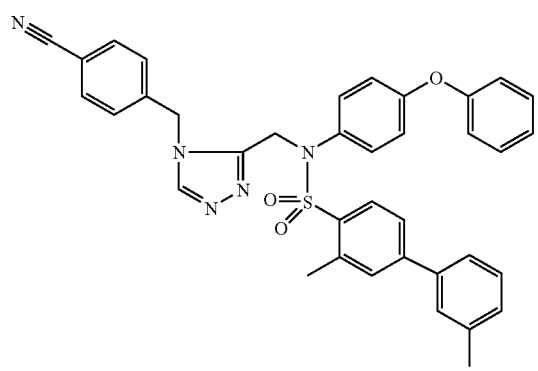
Trifluoroacetate (1:1) comp. 208.
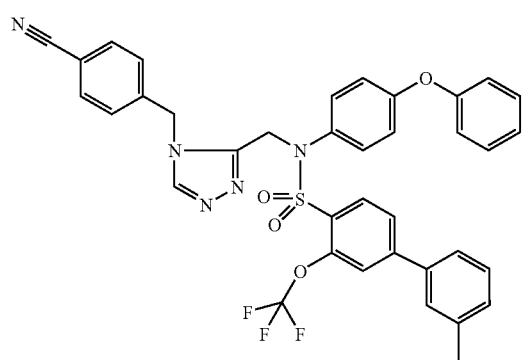
Trifluoroacetate (1:1) comp. 209.
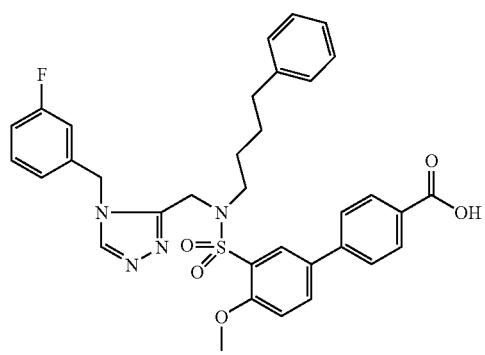
Trifluoroacetate (1:1) comp. 210.
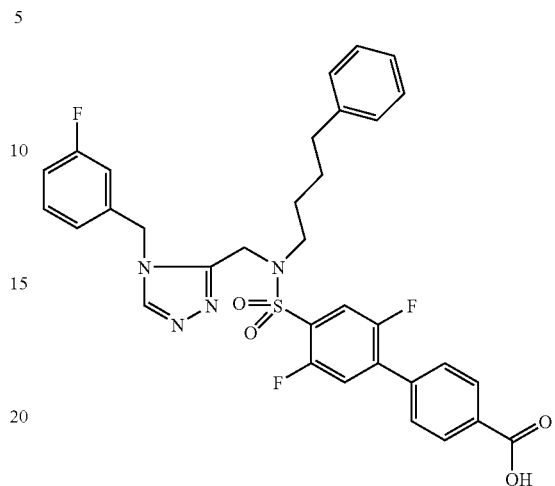
Trifluoroacetate (1:1) comp. 211.
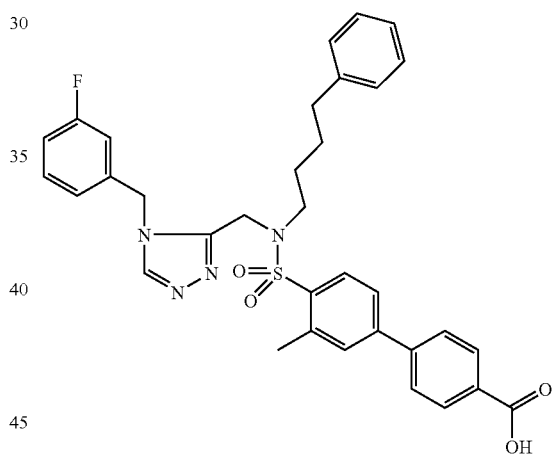
Trifluoroacetate (1:1) comp. 212.
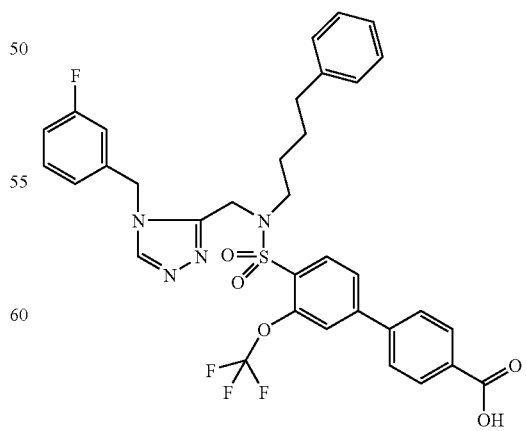
Trifluoroacetate (1:1) comp. 213.

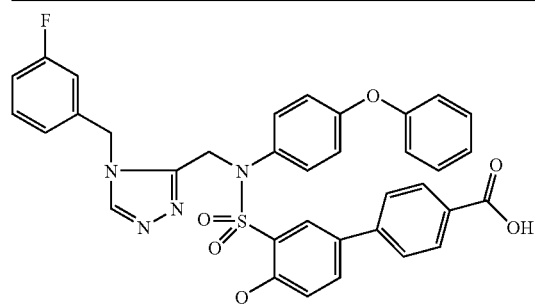
Trifluoroacetate (1:1) comp. 214.
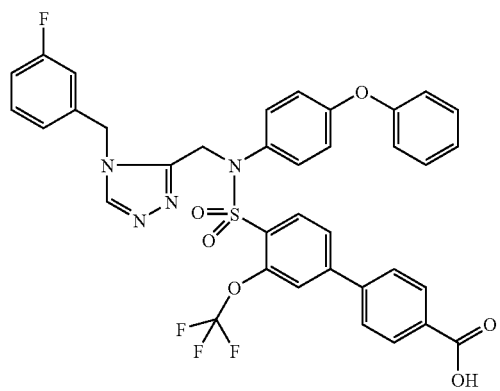
Trifluoroacetate (1:1) comp. 215.
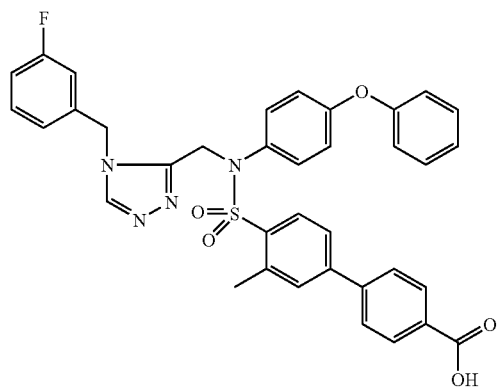
Trifluoroacetate (1:1) comp. 216.
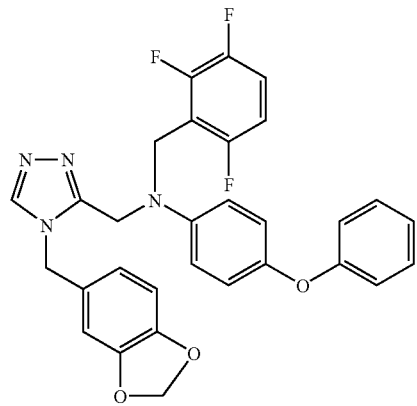
Trifluoroacetate (1:1) comp. 217.
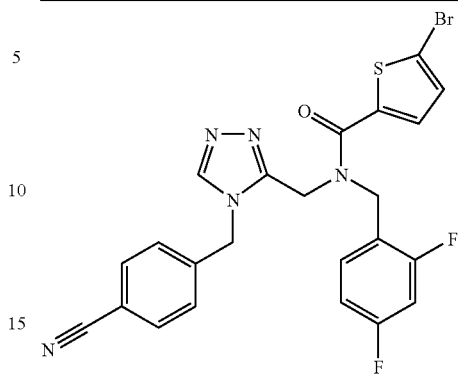
Trifluoroacetate (1:1) comp. 218
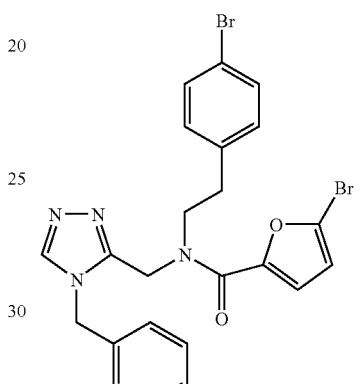
Trifluoroacetate (1:1) comp. 219
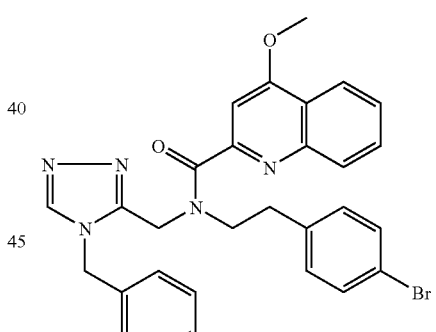
Trifluoroacetate (1:1) comp. 220
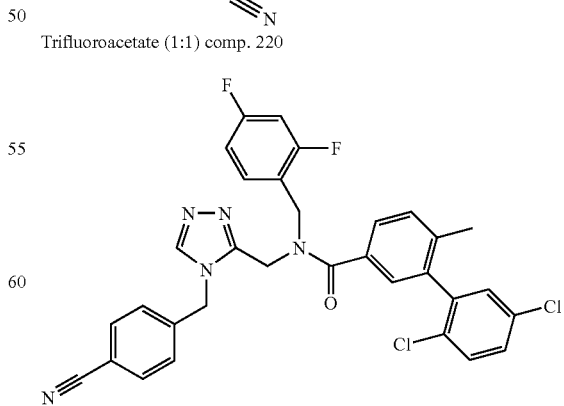
Trifluoroacetate (1:1) comp. 221

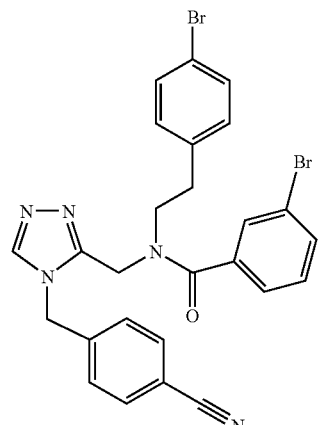
Trifluoroacetate (1:1) comp. 222
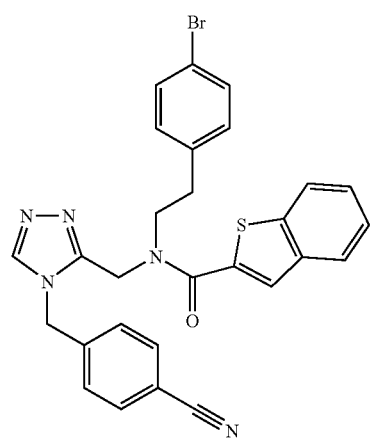
Trifluoroacetate (1:1) comp. 223
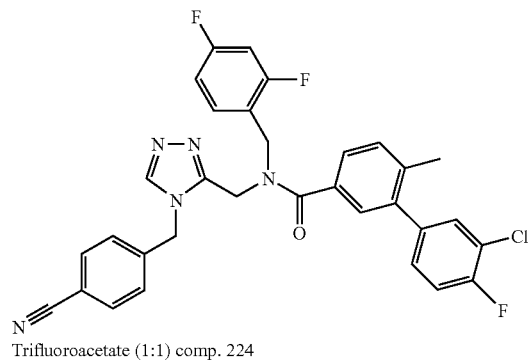
Trifluoroacetate (1:1) comp. 224
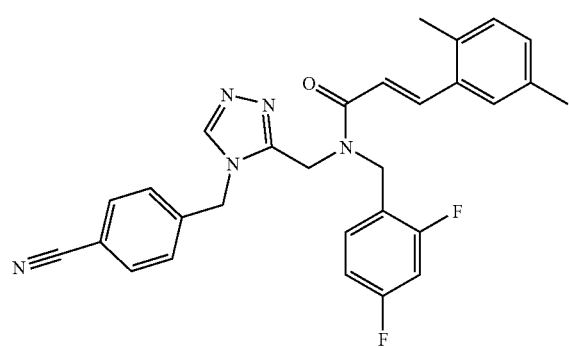
Trifluoroacetate (1:1) comp. 225
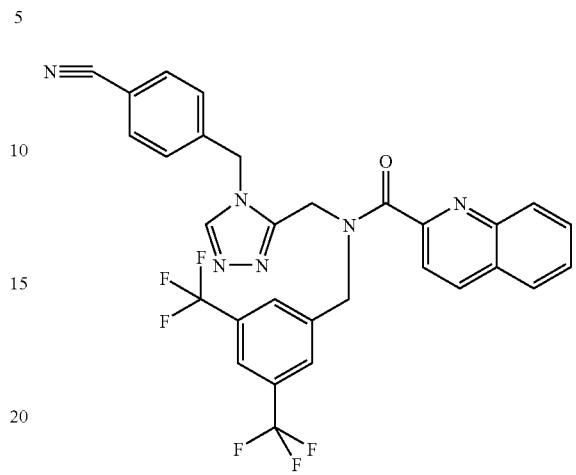
Trifluoroacetate (1:1) comp. 226
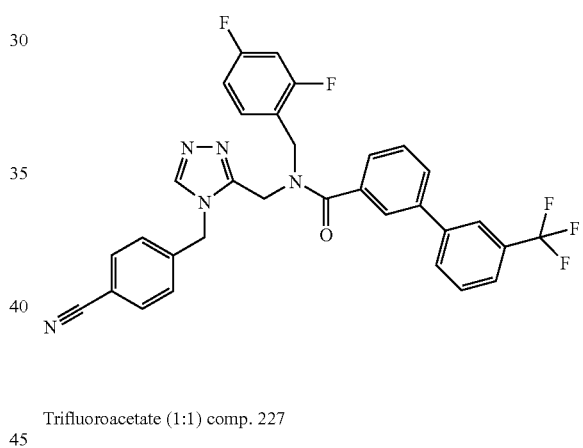
Trifluoroacetate (1:1) comp. 227
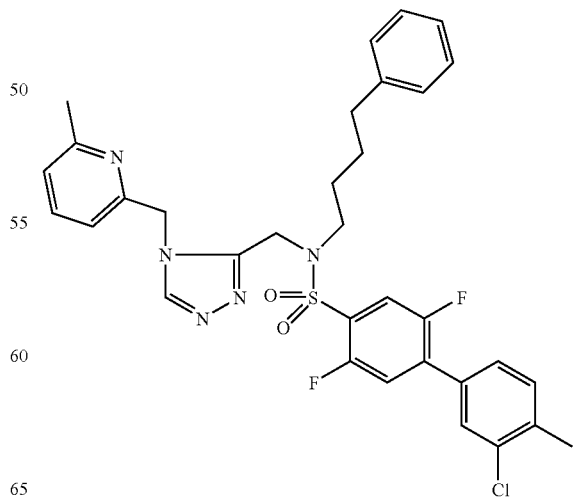
Trifluoroacetate (1:1) comp. 228

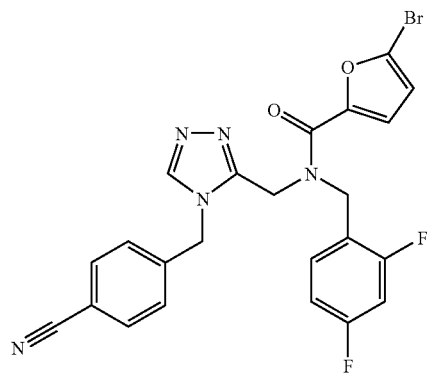
Trifluoroacetate (1:1) comp. 229
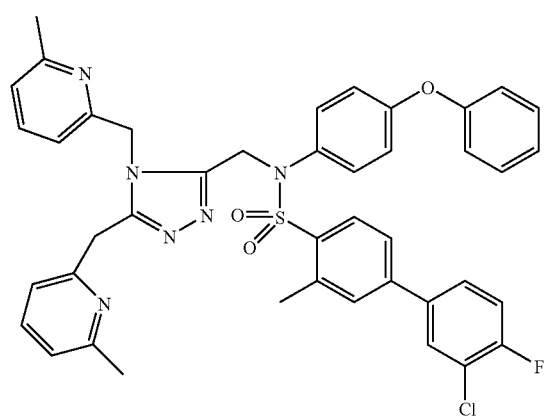
Trifluoroacetate (1:1) comp. 230
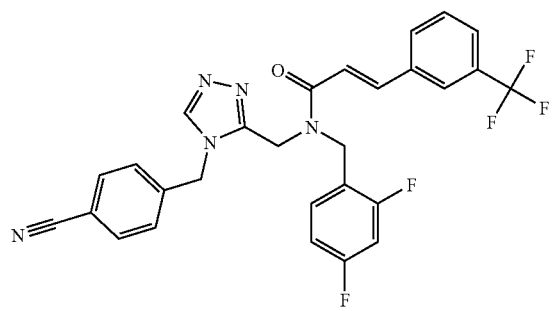
Trifluoroacetate (1:1) comp. 231
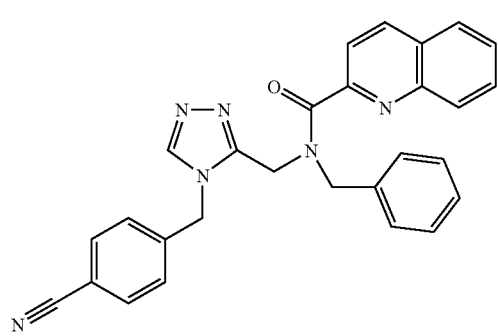
Trifluoroacetate (1:1) comp. 232
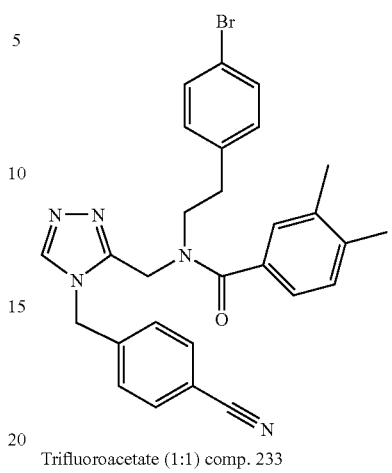
Trifluoroacetate (1:1) comp. 233
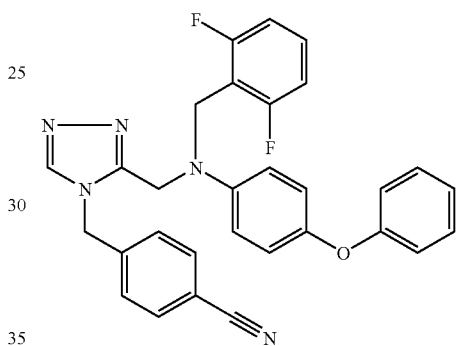
Trifluoroacetate (1:1) comp. 234
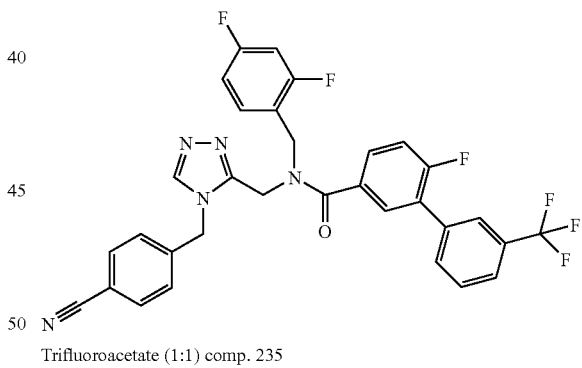
Trifluoroacetate (1:1) comp. 235
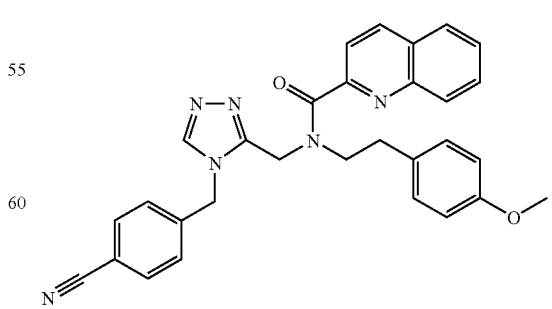
Trifluoroacetate (1:1) comp. 236

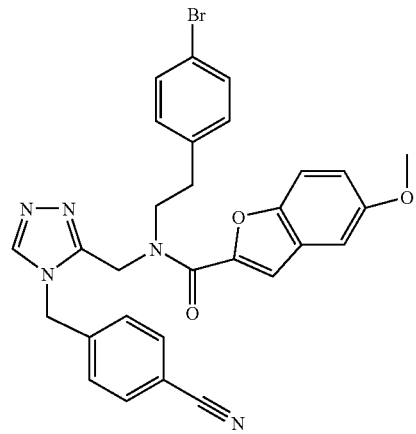
Trifluoroacetate (1:1) comp. 237
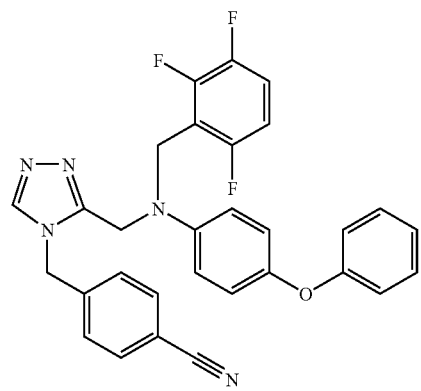
Trifluoroacetate (1:1) comp. 238
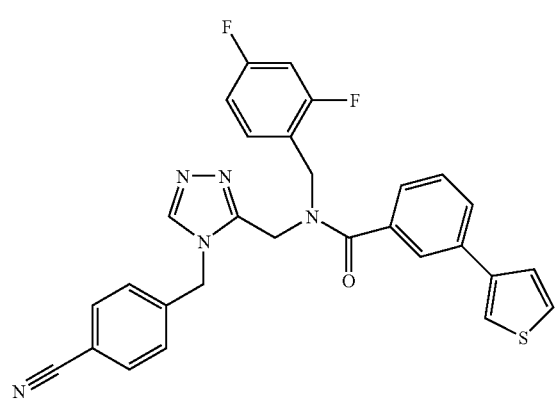
Trifluoroacetate (1:1) comp. 239
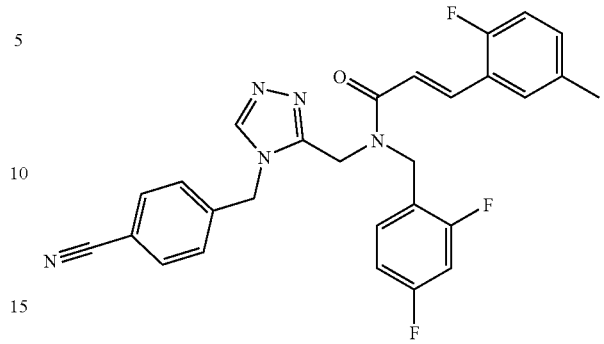
Trifluoroacetate (1:1) comp. 240
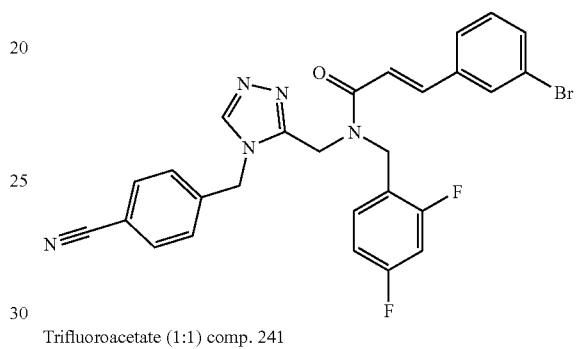
Trifluoroacetate (1:1) comp. 241
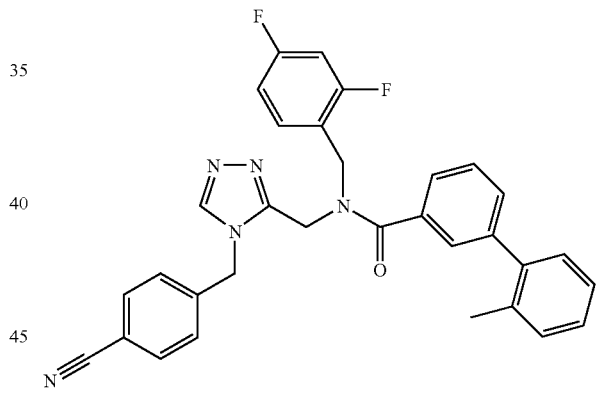
Trifluoroacetate (1:1) comp. 242
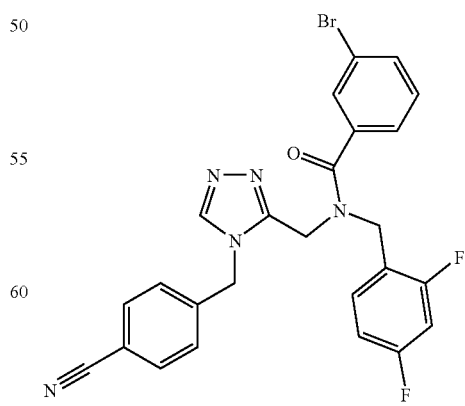
Trifluoroacetate (1:1) comp. 243

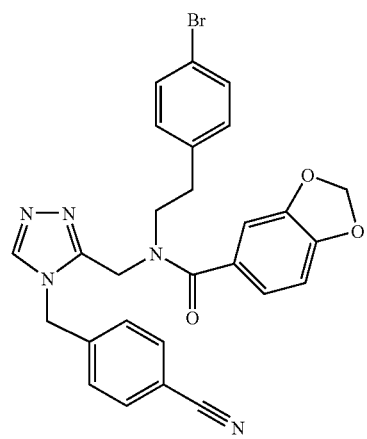
Trifluoroacetate (1:1) comp. 244
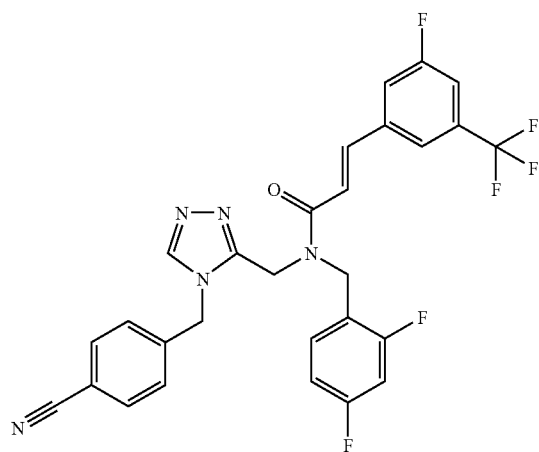
Trifluoroacetate (1:1) comp. 245
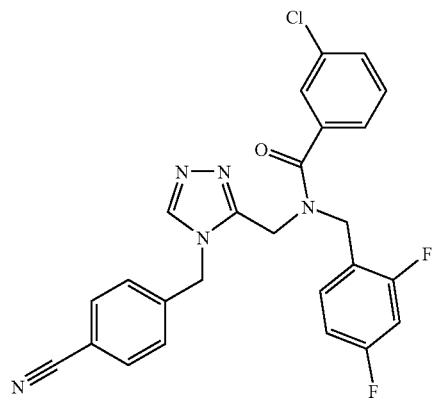
Trifluoroacetate (1:1) comp. 246
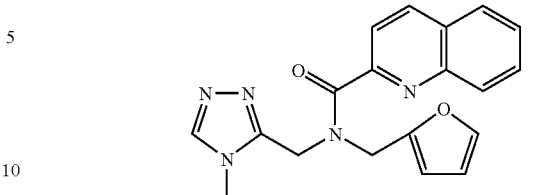
Trifluoroacetate (1:1) comp. 247
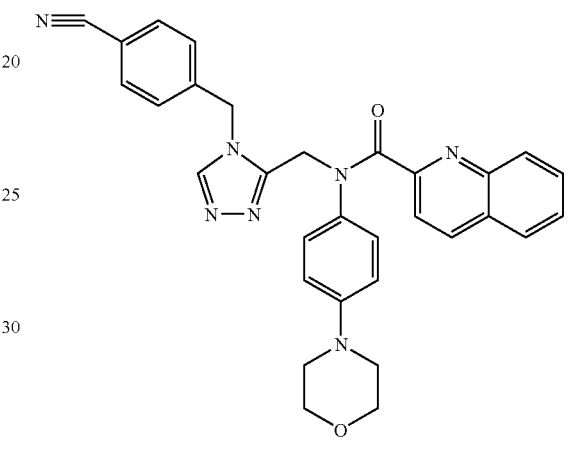
Trifluoroacetate (1:1) comp. 248
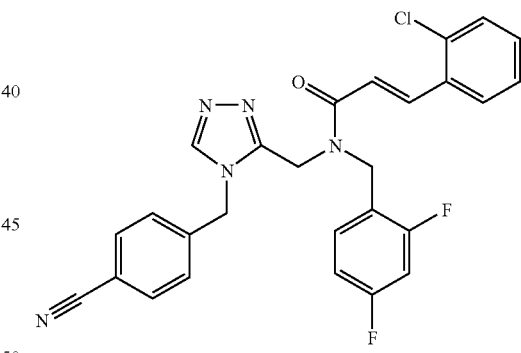
Trifluoroacetate (1:1) comp. 249
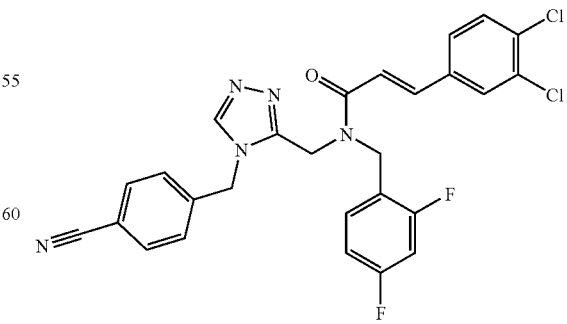
Trifluoroacetate (1:1) comp. 250

-continued
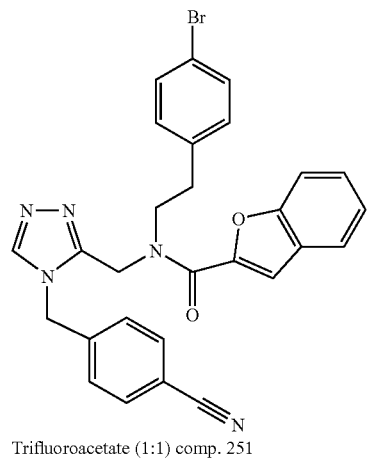
Trifluoroacetate (1:1) comp. 251
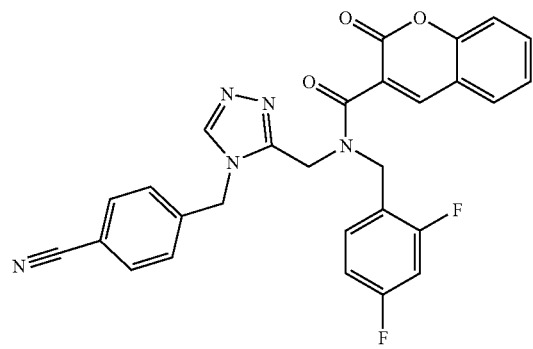
Trifluoroacetate (1:1) comp. 252
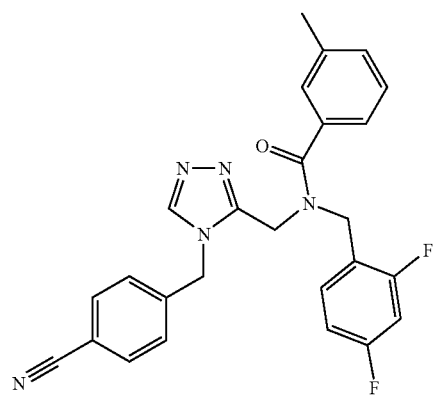
Trifluoroacetate (1:1) comp. 253
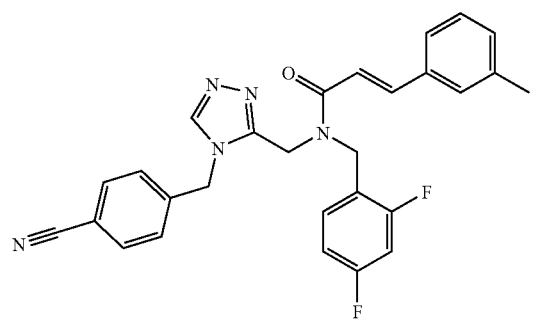
Trifluoroacetate (1:1) comp. 254
-continued
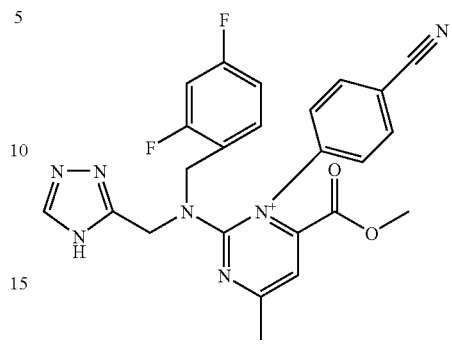
Trifluoroacetate (1:1) comp. 255
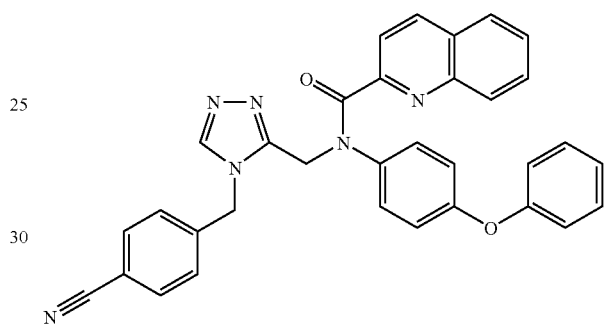
Trifluoroacetate (1:1) comp. 256
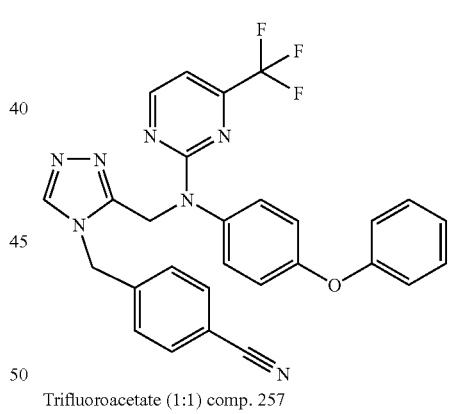
Trifluoroacetate (1:1) comp. 257
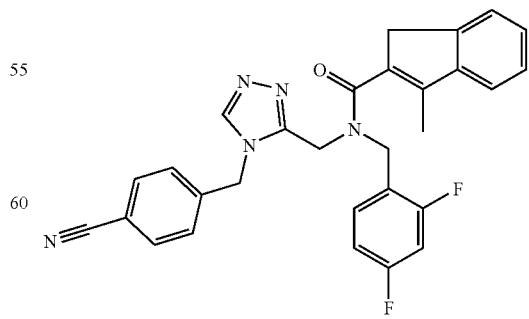
Trifluoroacetate (1:1) comp. 258

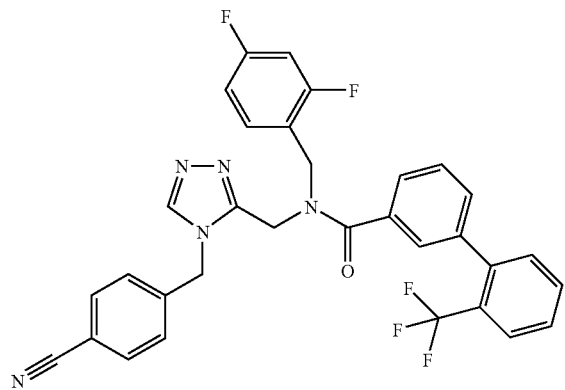
Trifluoroacetate (1:1) comp. 259
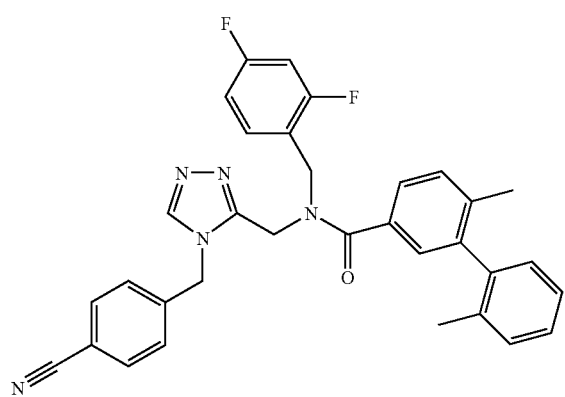
Trifluoroacetate (1:1) comp. 260
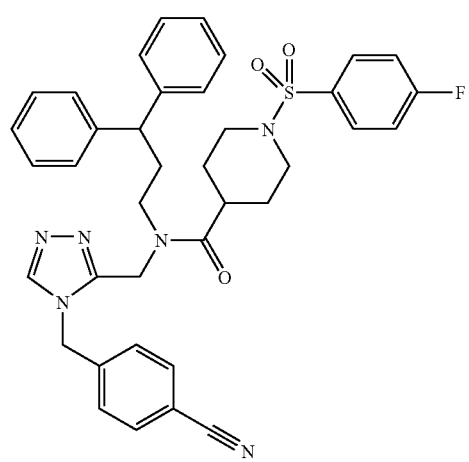
Trifluoroacetate (1:1) comp. 261
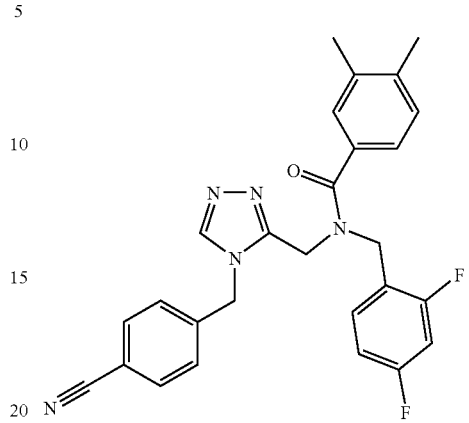
Trifluoroacetate (1:1) comp. 262
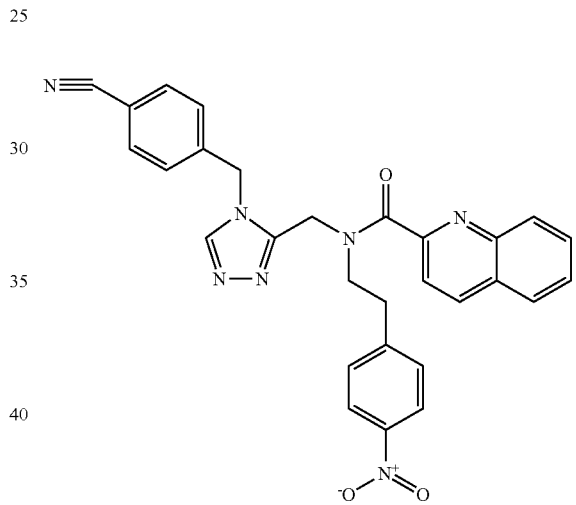
Trifluoroacetate (1:1) comp. 263
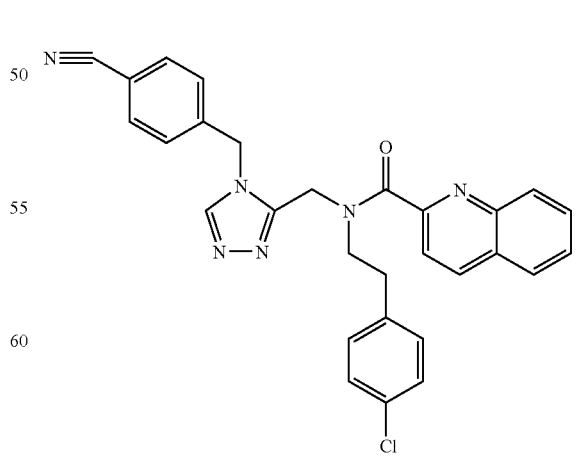
Trifluoroacetate (1:1) comp. 264

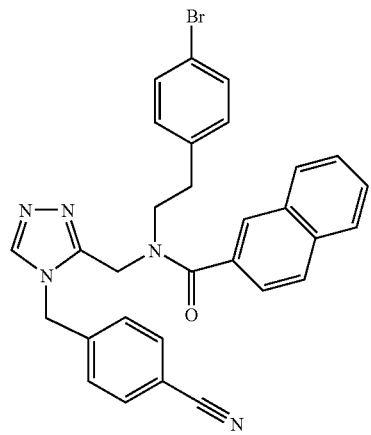
Trifluoroacetate (1:1) comp. 265
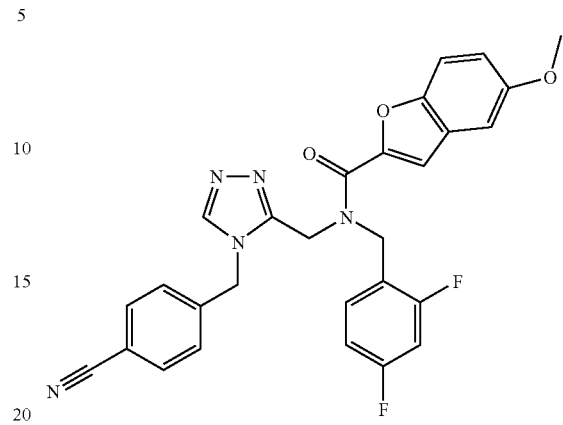
Trifluoroacetate (1:1) comp. 268
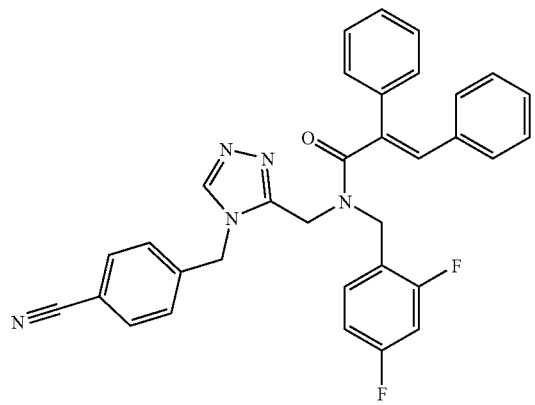
Trifluoroacetate (1:1) comp. 266
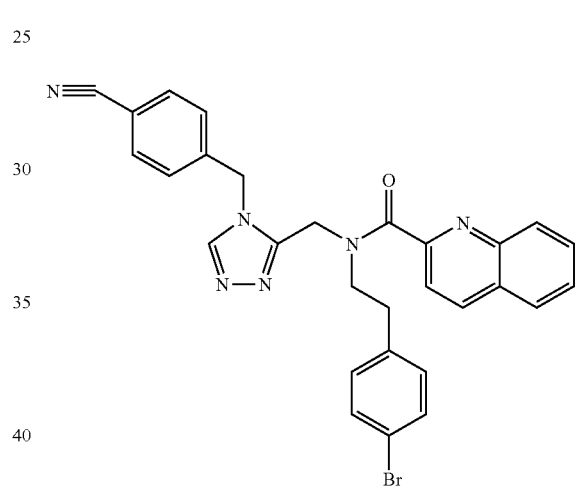
Trifluoroacetate (1:1) comp. 269
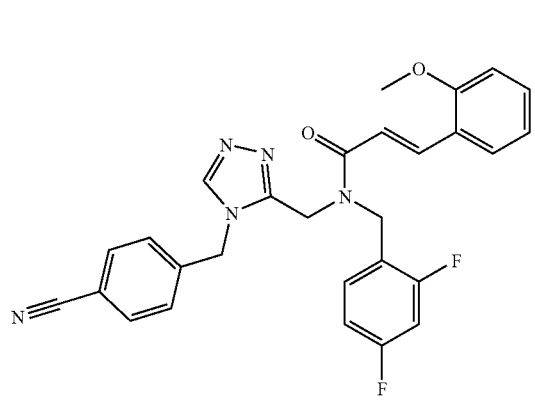
Trifluoroacetate (1:1) comp. 267
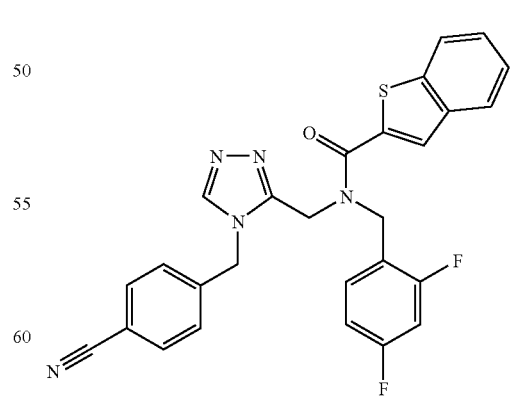
Trifluoroacetate (1:1) comp. 270

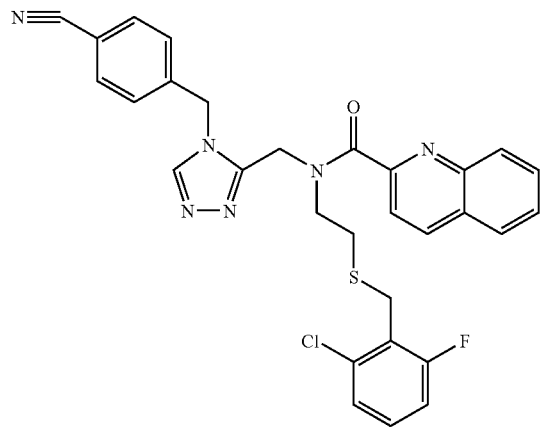
Trifluoroacetate (1:1) comp. 271
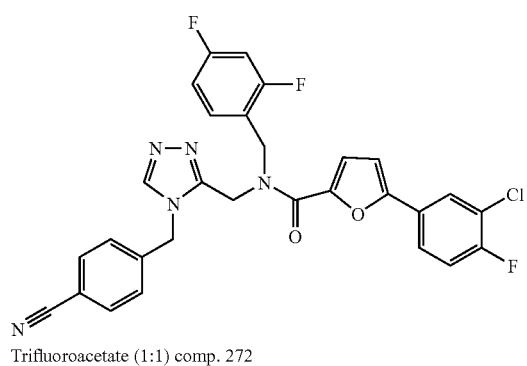
Trifluoroacetate (1:1) comp. 272
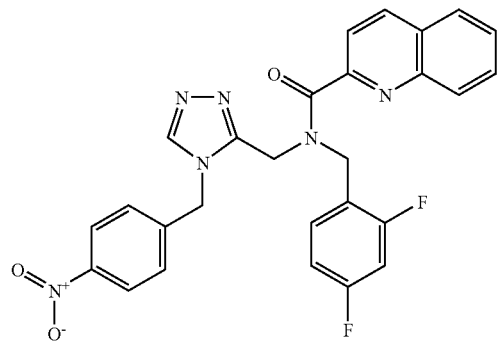
Trifluoroacetate (1:1) comp. 273
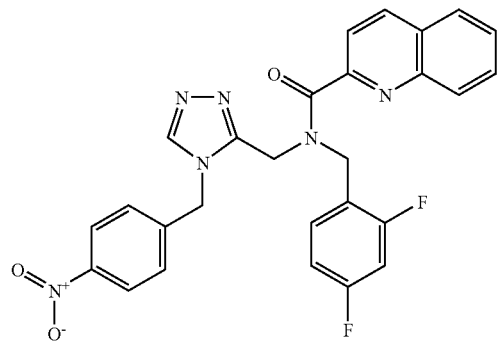
Trifluoroacetate (1:1) comp. 274
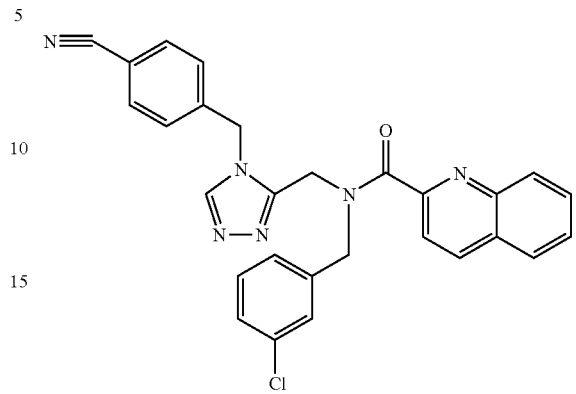
Trifluoroacetate (1:1) comp. 275
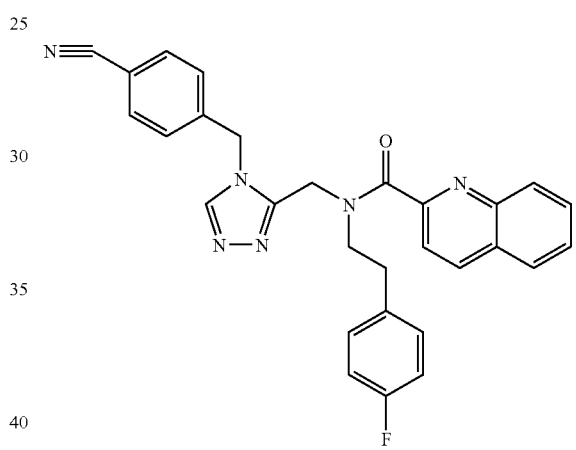
Trifluoroacetate (1:1) comp. 276
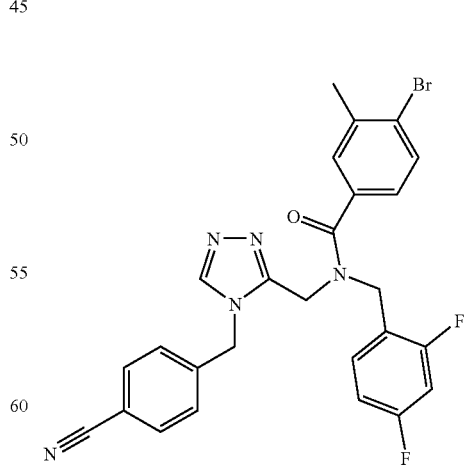
Trifluoroacetate (1:1) comp. 277

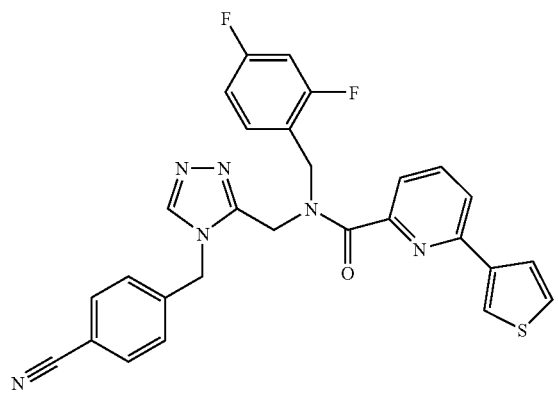
Trifluoroacetate (1:1) comp. 278
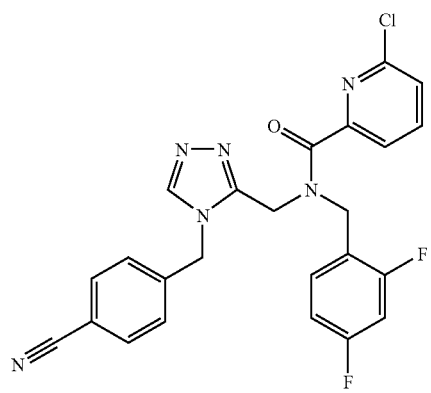
Trifluoroacetate (1:1) comp. 279
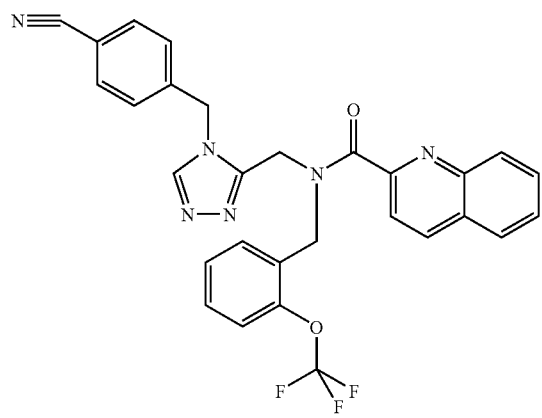
Trifluoroacetate (1:1) comp. 280
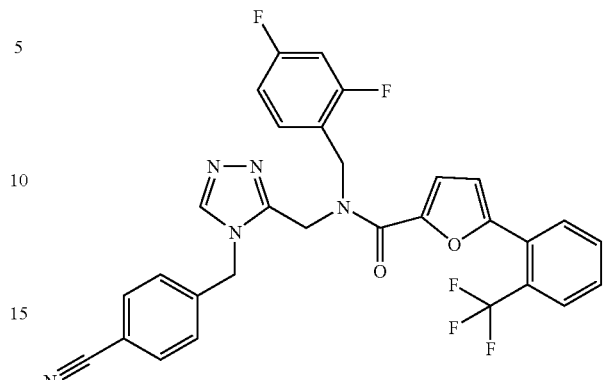
Trifluoroacetate (1:1) comp. 281
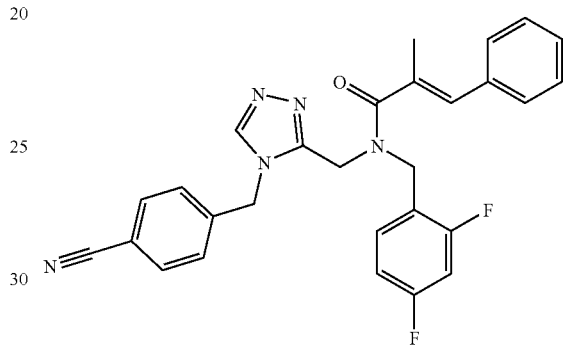
Trifluoroacetate (1:1) comp. 282
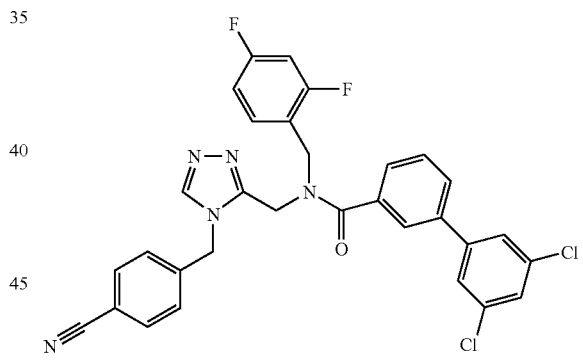
Trifluoroacetate (1:1) comp. 283
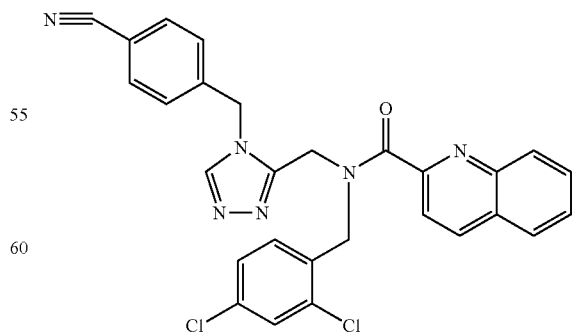
Trifluoroacetate (1:1) comp. 284

-continued
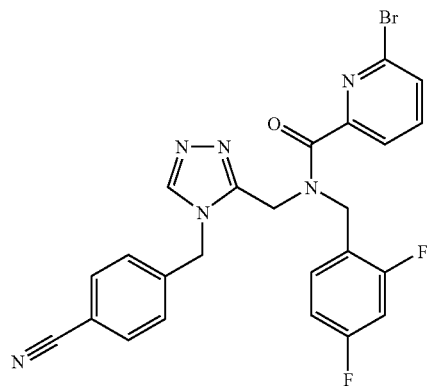
Trifluoroacetate (1:1) comp. 285
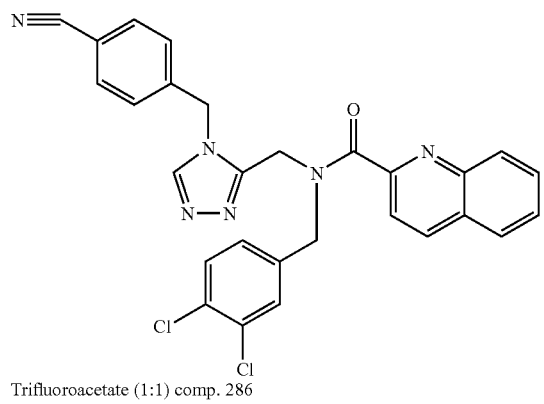
Trifluoroacetate (1:1) comp. 286
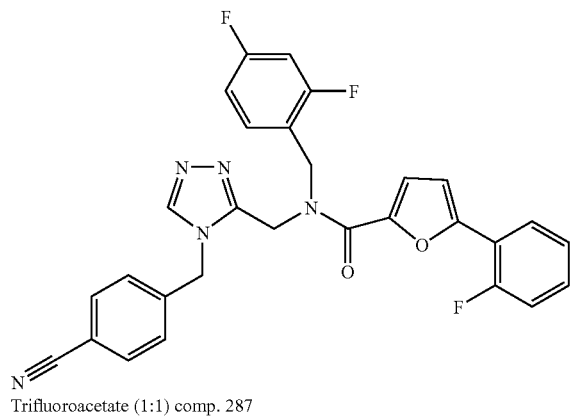
Trifluoroacetate (1:1) comp. 287
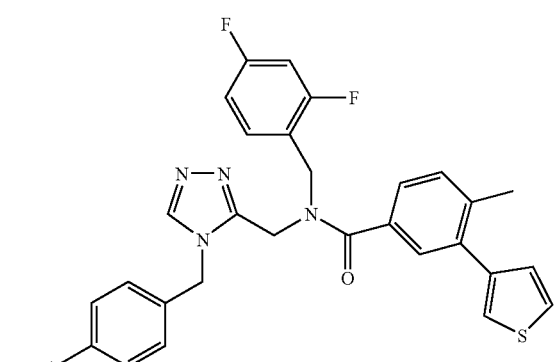
Trifluoroacetate (1:1) comp. 288
-continued
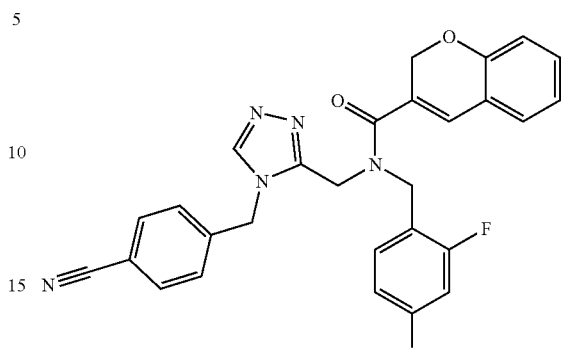
Trifluoroacetate (1:1) comp. 289
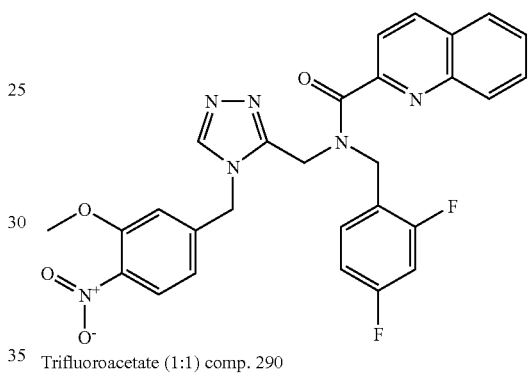
Trifluoroacetate (1:1) comp. 290
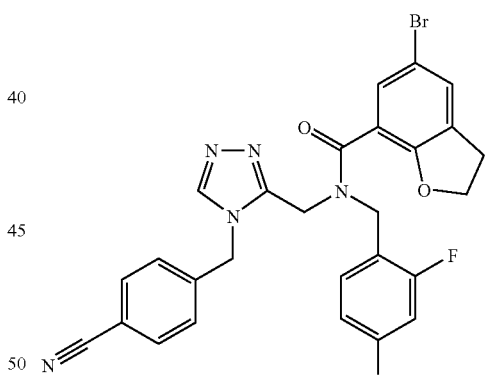
Trifluoroacetate (1:1) comp. 291
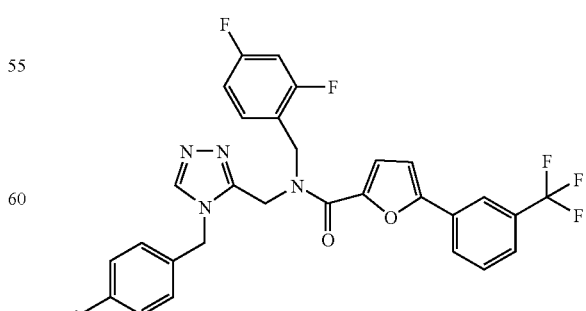
Trifluoroacetate (1:1) comp. 292

-continued
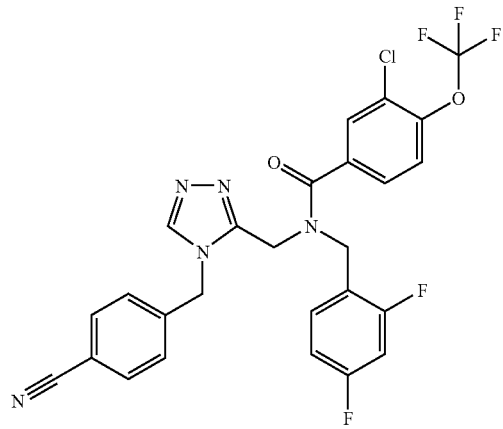
Trifluoroacetate (1:1) comp. 293
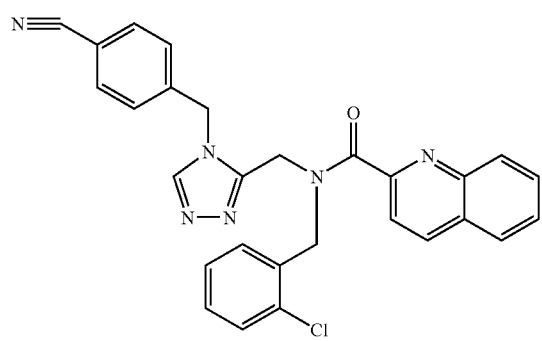
Trifluoroacetate (1:1) comp. 294
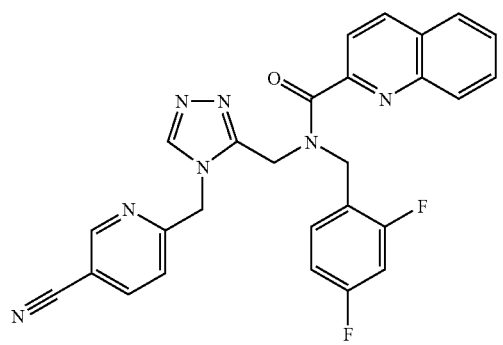
Trifluoroacetate (1:1) comp. 295
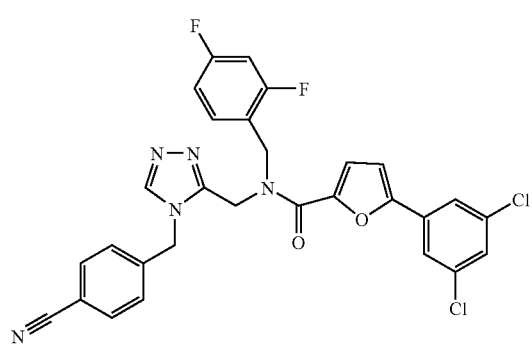
Trifluoroacetate (1:1) comp. 296
-continued
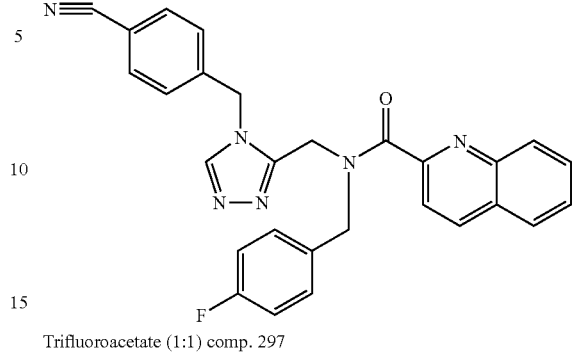
Trifluoroacetate (1:1) comp. 297
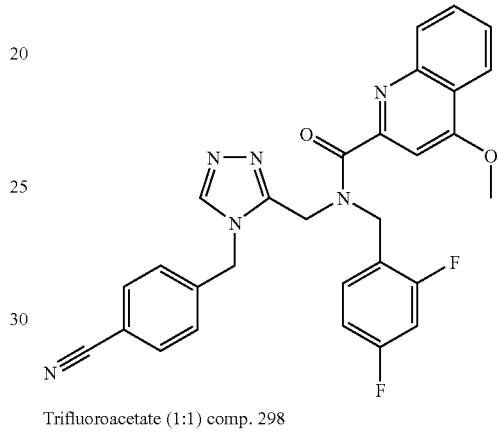
Trifluoroacetate (1:1) comp. 298
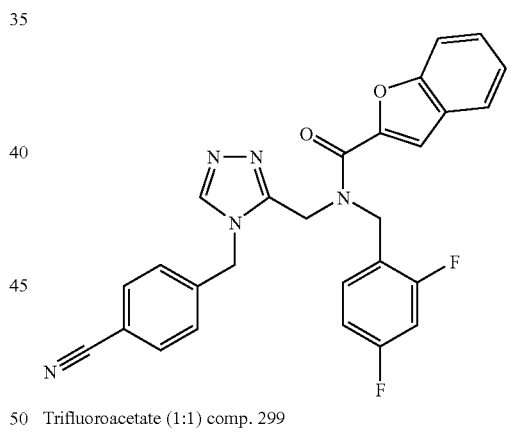
Trifluoroacetate (1:1) comp. 299
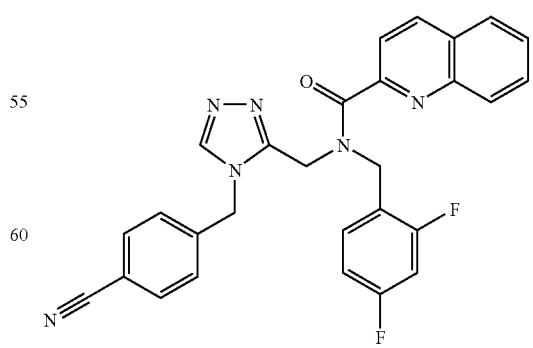
Trifluoroacetate (1:1) comp. 300

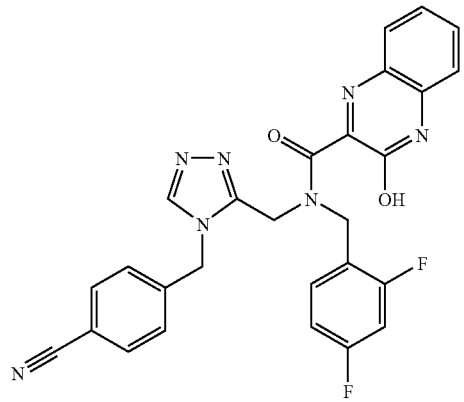
Trifluoroacetate (1:1) comp. 301
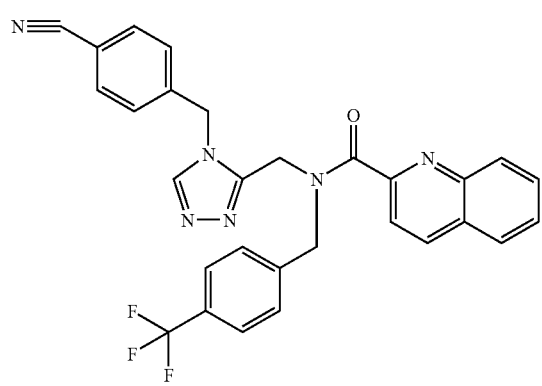
Trifluoroacetate (1:1) comp. 302
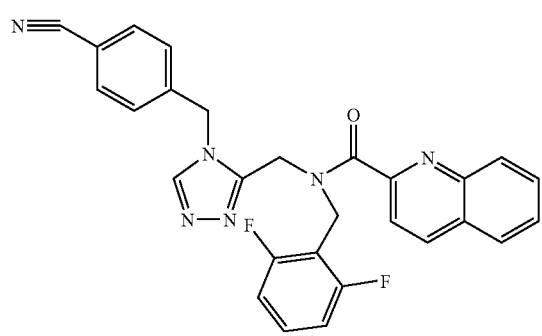
Trifluoroacetate (1:1) comp. 303
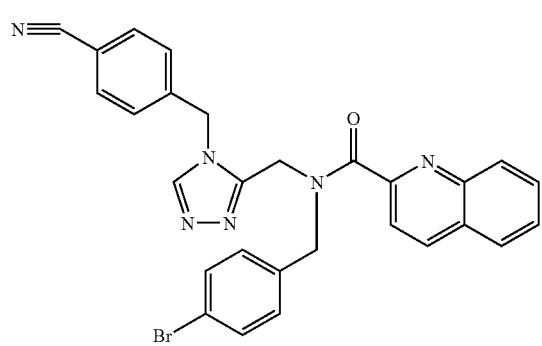
Trifluoroacetate (1:1) comp. 304
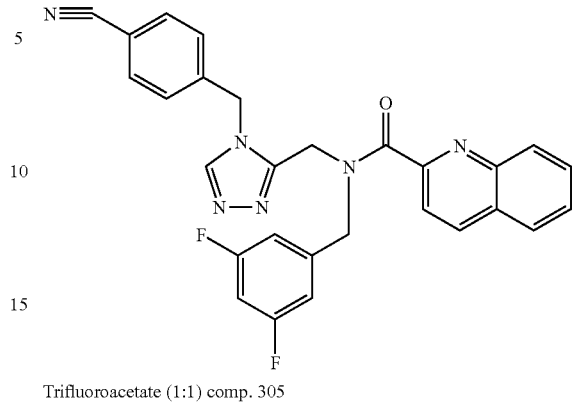
Trifluoroacetate (1:1) comp. 305
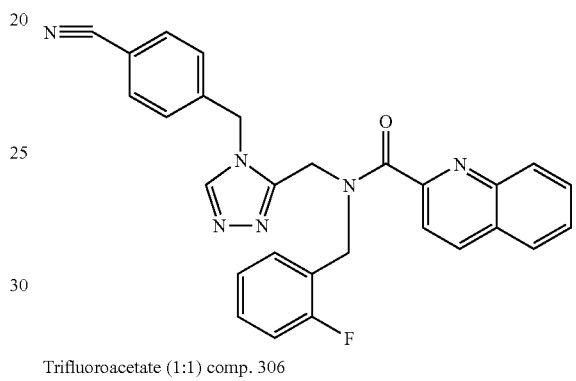
Trifluoroacetate (1:1) comp. 306
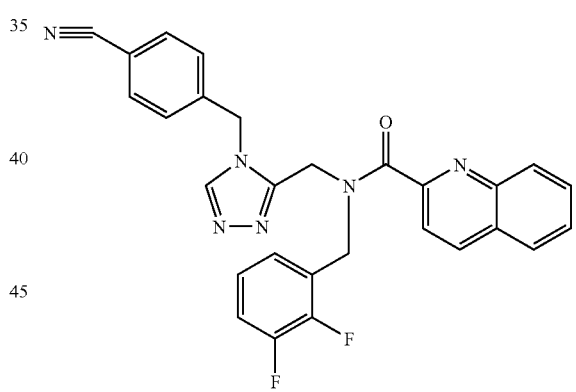
Trifluoroacetate (1:1) comp. 307
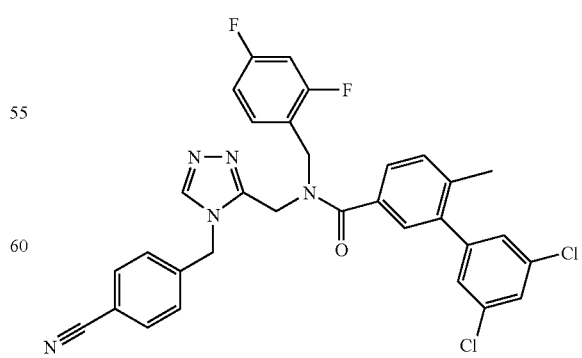
Trifluoroacetate (1:1) comp. 308

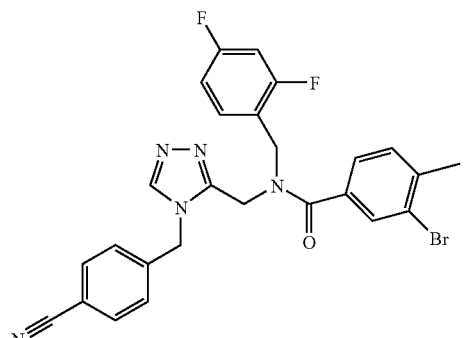

Trifluoroacetate (1:1) comp. 309

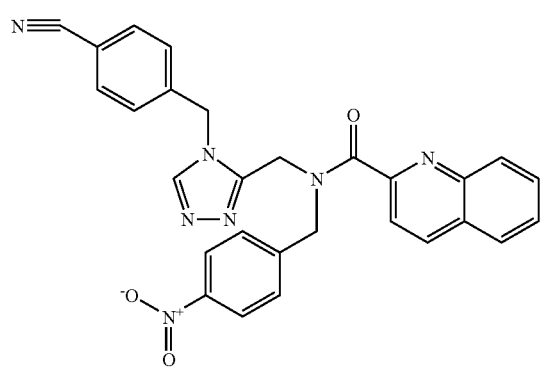

Trifluoroacetate (1:1) comp. 310

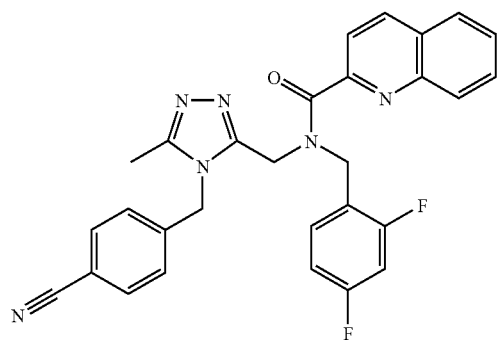

Trifluoroacetate (1:1) comp. 311

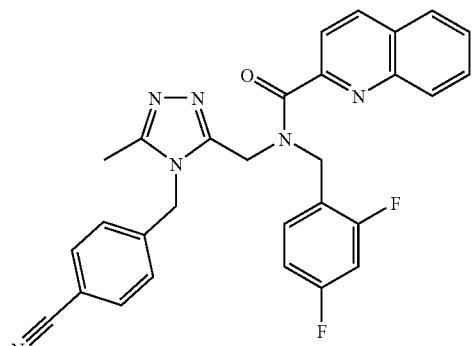

Trifluoroacetate (1:1) comp. 312

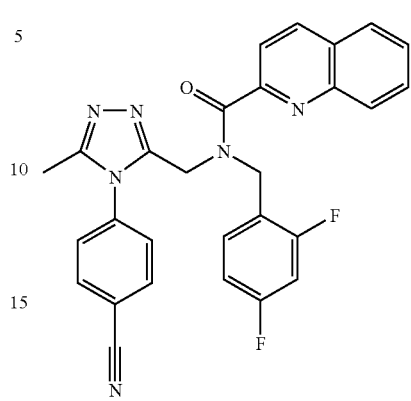

Trifluoroacetate (1:1) comp. 313

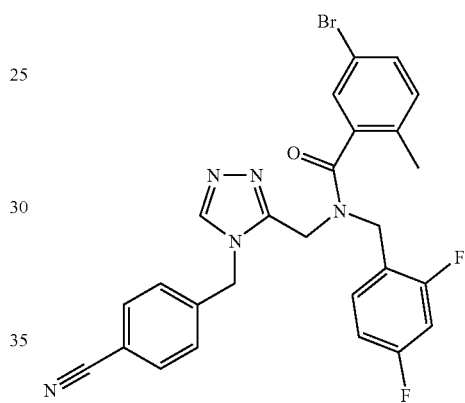

Trifluoroacetate (1:1) comp. 314

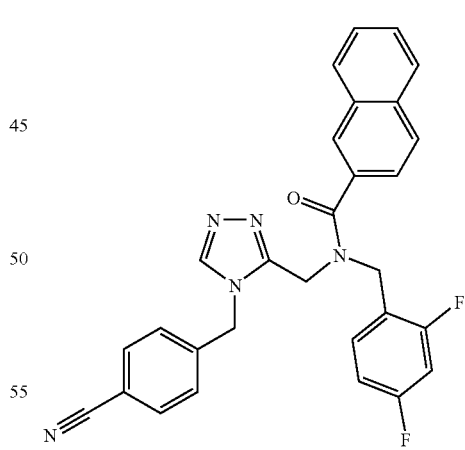

Trifluoroacetate (1:1) comp. 315

By way of illustration, the following table lists some physical data of the above exemplified compounds. The column "Rt LC" shows the retention time in minutes of the compound after liquid chromatography on a Supelco AZB Plus 4.6 mm 33 mm, 3 micron column using the method: 0.1% trifluoroacetic acid in $CH_3CN$ to 0.1% trifluoroacetic acid in water, 10 min.

| Comp No | Rt LC (min) | Purity | MH+ | Synthesis scheme |
|---|---|---|---|---|
| 1 | 6.23 | 98.3 | 467 | |
| 3 | 5.27 | 100 | 578/580 | |
| 4 | 6.02 | 96.8 | 566 | |
| 62 | 10.03 | 100 | 526 | |
| 85 | 5.32 | 97.82 | 506 | |
| 141 | 9.56 | 100 | 551/553 | |
| 164 | 5.33 | 100 | 502/504 | |
| 192 | 10.66 | 99.3 | 654 | |
| 218 | 5.11 | 100.0 | 529.38 | A |
| 219 | 5.22 | 100.0 | 570.27 | A |
| 220 | 5.00 | 100.0 | 582.48 | A |
| 221 | 10.72 | 98.3 | 603.47 | F |
| 222 | 5.50 | 100.0 | 580.31 | A |
| 223 | 5.61 | 100.0 | 557.49 | A |
| 224 | 10.40 | 99.2 | 587.02 | F |
| 225 | 9.84 | 94.3 | 498.55 | A |
| 226 | 10.27 | 100.0 | 595.52 | A |
| 227 | 10.24 | 98.5 | 588.55 | F |
| 228 | 10.67 | 94.9 | 641.13 | F |
| 229 | 4.67 | 100.0 | 513.32 | A |
| 230 | 10.48 | 100.0 | 760.30 | F |
| 231 | 9.78 | 93.7 | 538.49 | A |
| 232 | 8.77 | 100.0 | 459.52 | A |
| 233 | 5.49 | 92.1 | 529.46 | A |
| 234 | 9.97 | 98.0 | 508.54 | A |
| 235 | 10.43 | 93.5 | 602.58 | F |
| 236 | 4.72 | 96.3 | 503.58 | A |
| 237 | 5.45 | 100.0 | 571.45 | A |
| 238 | 10.03 | 100.0 | 526.53 | A |
| 239 | 9.57 | 100.0 | 526.58 | F |
| 240 | 9.83 | 100.0 | 567.39 | A |
| 241 | 9.76 | 100.0 | 549.40 | A |
| 242 | 10.05 | 100.0 | 534.58 | F |
| 243 | 9.30 | 95.3 | 523.36 | A |
| 244 | 4.96 | 100.0 | 545.41 | A |
| 245 | 9.95 | 89.5 | 556.48 | A |
| 246 | 9.18 | 97.8 | 478.90 | A |
| 247 | 4.23 | 96.5 | 449.49 | A |
| 248 | 8.08 | 100.0 | 530.60 | A |
| 249 | 9.52 | 98.8 | 504.94 | A |
| 250 | 10.12 | 91.7 | 539.38 | A |
| 251 | 5.45 | 100.0 | 541.43 | A |
| 252 | 8758.00 | 98.9 | 512.49 | A |
| 253 | 9.07 | 100.0 | 458.48 | A |
| 254 | 9.54 | 100.0 | 484.52 | A |
| 255 | 4.96 | 100.0 | 604.51 | A |
| 256 | 9.33 | 100.0 | 537.59 | A |
| 257 | 9.72 | 93.2 | 528.51 | A |
| 258 | 9.48 | 100.0 | 496.53 | A |
| 259 | 10.12 | 100.0 | 588.55 | F |
| 260 | 10.29 | 100.0 | 548.61 | F |
| 261 | 9.84 | 92.4 | 677.81 | H |
| 262 | 9.29 | 97.4 | 472.51 | A |
| 263 | 9.13 | 100.0 | 518.55 | A |
| 264 | 9.59 | 96.1 | 508.00 | A |
| 265 | 5.56 | 97.5 | 551.46 | A |
| 266 | 9.98 | 93.1 | 546.59 | A |
| 267 | 9.31 | 100.0 | 500.52 | A |
| 268 | 4.97 | 97.6 | 514.50 | A |
| 269 | 9.56 | 100.0 | 552.45 | A |
| 270 | 5.17 | 98.7 | 500.54 | A |
| 271 | 9.71 | 97.1 | 572.08 | A |
| 272 | 9.90 | 92.4 | 562.95 | F |
| 273 | 5.08 | 100.0 | 515.49 | A |
| 274 | 9.54 | 100.0 | 528.51 | F |
| 275 | 9.41 | 100.0 | 493.97 | A |
| 276 | 9.21 | 98.6 | 491.54 | A |
| 277 | 9.61 | 100.0 | 537.38 | A |
| 278 | 9.28 | 100.0 | 527.57 | F |
| 279 | 4.62 | 100.0 | 479.89 | A |
| 280 | 9.53 | 100.0 | 543.52 | A |
| 281 | 9.85 | 100.0 | 578.51 | F |
| 282 | 9.39 | 100.0 | 484.52 | A |
| 283 | 10.66 | 98.4 | 589.44 | F |
| 284 | 9.77 | 100.0 | 528.41 | A |
| 285 | 4.70 | 100.0 | 524.35 | A |
| 286 | 5.45 | 100.0 | 528.41 | A |
| 287 | 9.74 | 100.0 | 524.54 | F |
| 288 | 9.88 | 99.1 | 540.61 | F |
| 289 | 9.33 | 100.0 | 498.50 | A |
| 290 | 5.10 | 100.0 | 545.52 | A |
| 291 | 9.35 | 100.0 | 565.39 | A |
| 292 | 9.96 | 100.0 | 578.51 | F |
| 293 | 9.92 | 88.6 | 562.90 | A |
| 294 | 9.18 | 89.2 | 493.97 | A |
| 295 | 4.54 | 100.0 | 496.49 | A |
| 296 | 10.39 | 97.0 | 579.41 | F |
| 297 | 9.06 | 100.0 | 477.51 | A |
| 298 | 4.55 | 97.7 | 525.53 | A |
| 299 | 4.96 | 100.0 | 484.48 | A |
| 300 | 8.97 | 100.0 | 495.50 | A |
| 301 | 4.14 | 91.0 | 512.49 | A |
| 302 | 9.68 | 96.0 | 527.52 | A |
| 303 | 8.81 | 98.0 | 495.50 | A |
| 304 | 9.58 | 93.1 | 538.43 | A |
| 305 | 9.30 | 100.0 | 495.50 | A |
| 306 | 8.94 | 93.4 | 477.51 | A |
| 307 | 9.05 | 100.0 | 495.50 | A |
| 308 | 10.84 | 98.7 | 603.47 | F |
| 309 | 9.57 | 100.0 | 537.38 | A |
| 310 | 9.04 | 100.0 | 504.52 | A |
| 311 | 8.86 | 97.0 | 509.53 | A |
| 312 | 9.10 | 100.0 | 523.00 | J |
| 313 | 9.11 | 100.0 | 495.00 | J |

B. PHARMACOLOGICAL EXAMPLE

EXAMPLE B1

"In Vitro Assay for Inhibition of Farnesyl Protein Transferase"

An in vitro assay for inhibition of farnesyl transferase was performed essentially as described in WO 98/40383, pages 33-34.

The compound Nos. 4, 10, 11, 12, 13, 16, 23, 24, 25, 26, 29, 45, 48, 49, 50, 51, 52, 53, 54, 55, 56, 57, 58, 59, 60, 61, 62, 63, 64, 68, 69, 75, 79, 80, 83, 85, 108, 126, 129, 140, 141, 145, 146, 149, 153, 154, 156, 159, 160, 161, 162, 163, 170, 176, 180 and 182 had an inhibition of FPTase activity of at least 5% at a test dose of $10^{-5}$ M or lower.

The compound Nos. 218 to 315 had an inhibition of FPTase activity of at least 10% at a test dose of $10^{-7}$ M.

EXAMPLE B2

"In Vitro Screening for Activity Against Respiratory Syncytial Virus"

The percent protection against cytopathology caused by viruses (antiviral activity or $IC_{50}$) achieved by tested compounds and their cytotoxicity ($CC_{50}$) were both calculated from dose-response curves. The selectivity of the antiviral effect is represented by the selectivity index (SI), calculated by dividing the $CC_{50}$ (cytotoxic dose for 50% of the cells) by the $IC_{50}$ (antiviral activity for 50% of the cells).

Automated tetrazolium-based calorimetric assays were used for determination of $IC_{50}$ and $CC_{50}$ of test compounds. Flat-bottom, 96-well plastic microtiter trays were filled with 180 μl of Eagle's Basal Medium, supplemented with 5% FCS (0% for FLU) and 20 mM Hepes buffer. Subsequently, stock solutions (7.8× final test concentration) of compounds were added in 45 μl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 TCID$_{50}$ of Respiratory Syncytial Virus was added to two of the three rows in a volume of 50 μl. The same volume of medium was added to the third row to measure the cytotoxicity of the compounds at the same concentrations as those used to measure the antiviral activity. After two hours of incubation, a suspension (4×10$^5$ cells/ml) of HeLa cells was added to all wells in a volume of 50 μl. The cultures were incubated at 37° C. in a 5% CO$_2$ atmosphere. Seven days after infection the cytotoxicity and the antiviral activity was examined spectrophotometrically. To each well of the microtiter tray, 25 μl of a solution of MTT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 μl 2-propanol. Complete dissolution of the formazan crystals were obtained after the trays have been placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, so as to eliminate the effects of non-specific absorption.

Particular IC$_{50}$, CC$_{50}$ and SI values are listed in the Table hereinbelow.

| Co. No. | IC$_{50}$ (μM) | CC$_{50}$ (μM) | SI |
| --- | --- | --- | --- |
| 90 | 0.0259 | 7.59 | 1988 |
| 97 | 0.0800 | 7.10 | 322 |
| 102 | 0.0824 | 7.08 | 793 |
| 46 | 0.0881 | 7.06 | 758 |
| 157 | 0.0931 | 7.03 | 272 |
| 114 | 0.1183 | 6.93 | 337 |
| 101 | 0.1279 | 6.89 | 196 |
| 92 | 0.1503 | 6.82 | 147 |
| 155 | 0.1600 | 6.80 | 99 |

The invention claimed is:

1. A compound of formula

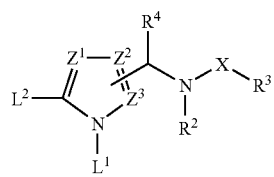

(I)

a prodrug, N-oxide, addition salt, quaternary amine, or stereochemically isomeric form thereof, wherein L$^1$ and L$^2$ are R$^1$—Y— wherein each (R$^1$—Y)— substituent is defined independently of the other;

Y is C$_{1-4}$alkanediyl, C$_{2-4}$alkenediyl, C$_{2-4}$alkynediyl, C(=O), or a direct bond;

R$^1$ is hydrogen, cyano, aryl or a substituted or unsubstituted C$_{1-14}$heterocycle; =Z$^1$-Z$^2$=Z$^3$- is a radical of formula =N—N=CH— (a-1), =N—CH=N— (a-2), or =CH—N=N— (a-3);

X is SO$_2$, (CH$_2$)$_n$ wherein n is 1 to 4, C(=O), C(=S), or a direct bond;

R$^2$ is a substituted or unsubstituted C$_{1-14}$heterocycle, or C$_{1-12}$alkyl substituted with one or more substituents independently selected from a substituted or unsubstituted C$_{1-14}$heterocycle;

R$^3$ is aryl, —NR$^5$R$^6$, a substituted or unsubstituted C$_{1-14}$heterocycle, or C$_{2-4}$alkenediyl substituted with a substituted or unsubstituted C$_{1-14}$heterocycle or aryl;

R$^4$ is hydrogen, aryl, C$_{3-7}$cycloalkyl, C$_{1-6}$alkyl or C$_{1-6}$alkyl substituted with C$_{3-7}$cycloalkyl, hydroxycarbonyl, C$_{1-4}$alkyloxycarbonyl or aryl; and R$^5$ and R$^6$ are each independently selected from hydrogen, a substituted or unsubstituted C$_{1-14}$heterocycle, aryl, C$_{1-12}$alkyl and C$_{1-12}$alkyl substituted with one or more substituents selected from hydroxy, aryl, aryloxy or a substituted or unsubstituted C$_{1-14}$heterocycle.

2. A compound of claim 1 in which the hetereocycle is 1H-pyrazolo[3,4-d]pyrimidinyl, benzimidazolyl, benzodioxolanyl, benzodioxolyl, benzofuranyl, benzopyranyl, benzopyridinyl, benzothiazolyl, benzothienyl, benzoxazolyl, cinnolinyl, dihydrobenzofuranyl, dihydropyrimidinyl, dioxanyl, dioxolanyl, dithianyl, furanyl, imidazo[2,1-b]thiazolyl, imidazolinyl, imidazolyl, indanyl, indolinyl, indolyl, isobenzofuranyl, isobenzothienyl, isoindolyl, isoquinolinyl, isoquinolyl, isothiazolyl, isoxazolyl, morpholinyl, oxadiazolyl, oxazolidinyl, oxazolinyl, oxazolopyridinyl, oxazolyl, phtalazinyl, piperazinyl, piperidinyl, purinyl, pyranyl, pyrazinyl, pyrazolinyl, pyrazolyl, pyridazinyl, pyridinyl, pyrimidinyl, pyrrolidinyl, pyrrolinyl, pyrrolyl, quinazolinyl, quinolinyl, quinoxalinyl, tetrahydrofuranyl, tetrahydropyranyl;, tetrahydropyridinyl, tetrazolyl, thiadazolyl, thiazolinyl, thiazolopyridinyl, thiazolyl, thienyl, thiolanyl, thiomorpholinyl, triazinyl, triazolyl, triazospirodecanyl or trithianyl.

3. A compound of claim 1 in which the heterocycle is triazolyl, thienyl, quinolinyl, benzothiazolyl, quinoxalinyl, imidazolyl, benzimidazolyl, pyridinyl, pyrimidinyl, pyridazinyl, furanyl, benzofuranyl, furanyl, dihydrobenzofuranyl, benzopyranyl, benzothienyl, pyrrolidinyl, indanyl, benzodioxolanyl, morpholinyl, pyrazinyl and triazinyl.

4. A compound of claim 1 in which the C$_{1-14}$heterocycle may be substituted with one or more substituents selected from substituted or unsubstituted phenyl, trifluoromethyl, trifluoromethyloxy, halo, hydroxy, cyano, nitro, C$_{1-12}$alkyl, C$_{1-12}$alkyloxy, hydroxycarbonyl, C$_{1-6}$alkyloxycarbonyl, amino, aminocarbonyl, furanyl, mono- or di(C$_{1-4}$alkyl)amino, thienyl, pyridinyl, mono- or di(C$_{1-4}$alkyl)aminocarbonyl, C$_{1-6}$alkylcarbonylamino, substituted or unsubstituted phenylsulfonyl, substituted or unsubstituted phenylcarbonyl and C$_{1-12}$alkyl substituted with one or more substituents selected from substituted or unsubstituted phenyl, pyrazinyl, furanyl and thienyl.

5. A compound of claim 1 wherein;
a) Y is C$_{1-4}$alkanediyl or a direct bond; or
b) R$^1$ is hydrogen, cyano, aryl, or a substituted or unsubstituted C$_{1-14}$heterocycle; or
c) =Z$^1$-Z$^2$=Z$^3$- is a radical of formula (a-1) or (a-2), in particular (a-1); or
d) R$^2$ is a substituted or unsubstituted C$_{1-14}$heterocycle; or
e) R$^3$ is aryl, —NR$^5$R$^6$, substituted or unsubstituted C$_{1-14}$heterocycle, or C$_{2-4}$alkenediyl substituted with one or more substituents selected from aryl, and a substituted or unsubstituted $C_{1-14}$heterocycle; or
f) $R^4$ is hydrogen or $C_{1-6}$alkyl; or
g) $R^5$, $R^6$ or X are defined as above.

6. A compound of claim 1 wherein;
a) $L^1$ is $R^1$—Y— wherein $R^1$ is hydrogen, substituted or unsubstituted phenyl, benzodioxolyl, pyridinyl or pyridinyl substituted with one or more substituents selected from $C_{1-6}$alkyl, hydroxy, halo, cyano, and $C_{1-6}$alkyloxycarbonyl and wherein Y is $C_{1-4}$alkanediyl or a direct bond; or
b) $L^2$ is $R^1$—Y— wherein $R^1$ is hydrogen, cyano, substituted or unsubstituted phenyl and wherein Y is $C_{1-4}$alkanediyl or a direct bond; or
c) $=Z^1-Z^2=Z^3-$ is a radical of formula (a-1);
d) X is $SO_2$, C(=O) or a direct bond; or
e) $R^2$ is a substituted or unsubstituted $C_{1-14}$heterocycle; or
f) $R^3$ is aryl, a substituted or unsubstituted $C_{1-14}$heterocycle, or a $C_{2-4}$alkenediyl substituted with one or more aryl; or
g) $R^4$ is hydrogen; or
h) $R^5$ or $R^6$ are defined as above.

7. A compound of claim 1 wherein $L^1$ is $R^1$—Y— wherein $R^1$ is hydrogen, phenyl, pyridinyl, phenyl substituted with one or more substituents selected from halo, nitro, cyano, $C_{1-12}$alkyl, and $C_{1-12}$alkyloxy, or pyridinyl substituted with one or more substituents selected from $C_{1-6}$alkyl and cyano and wherein Y is $C_{1-4}$alkanediyl;
$L^2$ is $R^1$—Y— with $R^1$ is hydrogen or cyano and wherein Y is $C_{1-4}$alkanediyl or a direct bond;
$=Z^1-Z^2=Z^3-$ is a radical of formula (a-1);
$R^2$ is a substituted or unsubstituted $C_{1-14}$heterocycle;
$R^3$ is aryl, a substituted or unsubstituted $C_{1-14}$heterocycle selected from quinoline, quinoxaline, benzofuran, furan, dihydrobenzofuran, benzopyran, pyridine, benzothiophene, pyrrolidine, indene, benzodioxolane, and thiophene, or a $C_{2-4}$alkenediyl substituted with one or more substituents selected from naphthyl, phenyl, and phenyl substituted with one or more substituents selected from halo, cyano, nitro, substituted or unsubstituted phenyl, phenyloxy, trifluoromethyl, methoxy, thienyl, trifluoromethyloxy, morpholinyl, and $C_{1-12}$alkyl; and
$R^4$ is hydrogen.

8. A compound of claim 1 of formula (I-a)

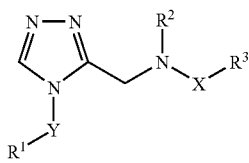

(I-a)

a prodrug, N-oxide, addition salt, quaternary amine, or stereochemically isomeric form thereof, wherein X is $SO_2$, $(CH_2)_n$, C(=O), or a direct bond;
Y is $C_{1-4}$alkanediyl, $C_{2-4}$alkenediyl, $C_{2-4}$alkynediyl, or C(=O);
$=Z^1-Z^2=Z^3-$ is a radical of formula =N—N=CH— (a-1), =N—CH=N— (a-2), or =CH—N=N— (a-3);

n is 1 to 4;
$R^1$ is aryl or a substituted or unsubstituted $C_{1-14}$heterocycle;
$R^2$ is triazolyl, thienyl, quinolinyl, benzothiazolyl, quinoxalinyl, imidazolyl, benzimidazolyl, pyridinyl, pyrimidinyl, pyridazinyl, furanyl, benzofuranyl, furanyl, dihydrobenzofuranyl, benzopyranyl, benzothienyl, pyrrolidinyl, indanyl, benzodioxolanyl, morpholinyl, pyrazinyl and triazinyl;
$R^3$ is aryl or substituted or unsubstituted $C_{1-14}$heterocycle;
$R^4$ is hydrogen, aryl, $C_{3-7}$cycloalkyl or $C_{1-6}$alkyl optionally substituted with $C_{3-7}$cycloalkyl, hydroxycarbonyl, $C_{1-4}$alkyloxycarbonyl, or aryl; and
aryl is naphthyl or phenyl each of which may optionally be substituted with one or more substituents selected from trifluoromethyl, trifluoromethyloxy, halo, cyano, nitro, $C_{1-12}$alkyl, $C_{1-12}$alkyloxy, phenyl$C_{1-6}$alkyl, phenyl$C_{1-6}$alkyloxy, phenyloxy, phenylcarbonyl, hydroxycarbonyl, $C_{1-6}$alkyloxycarbonyl, amino, mono- or di($C_{1-4}$alkyl)amino, $C_{1-6}$alkylcarbonylamino, substituted or unsubstituted phenyl, or a $C_{1-14}$heterocycle.

9. A compound of claim 8 wherein;
Y is $C_{1-4}$alkanediyl, $C_{1-4}$alkynediyl, or C(=O);
$=Z^1-Z^2=Z^3-$ is a radical of formula (a-1) or (a-2);
$R^1$ is phenyl, benzodioxolyl, or pyridinyl wherein said phenyl may optionally be substituted with one or more substituents selected from halo, nitro, cyano, $C_{1-12}$alkyl, $C_{1-12}$alkyloxy, $C_{1-6}$alkyloxycarbonyl, and trifluoromethyl; and wherein said pyridinyl may optionally be substituted with one or more substituents selected from $C_{1-6}$alkyl, hydroxy, halo, cyano, and $C_{1-6}$alkyloxycarbonyl;
$R^2$ is a substituted or unsubstituted $C_{1-14}$heterocycle;
$R^3$ is aryl or a substituted or unsubstituted $C_{1-14}$heterocycle selected from triazole, thiophene, quinoline, benzothiazole, quinoxaline, imidazole, benzimidazole, pyridine, pyrimidine and triazine; and
$R^4$ is hydrogen.

10. A compound of claim 9 wherein $=Z^1-Z^2=Z^3-$ is a radical of formula (a-1).

11. A pharmaceutical composition comprising a therapeutically effective amount of a compound of claim 1 and a pharmaceutically acceptable carrier therefor.

12. A pharmaceutical composition comprising a therapeutically effective amount of a compound of claim 8 and a pharmaceutically acceptable carrier therefor.

* * * * *